US011840523B2

(12) United States Patent
Papa et al.

(10) Patent No.: US 11,840,523 B2
(45) Date of Patent: Dec. 12, 2023

(54) IRE1α INHIBITORS AND USES THEREOF

(71) Applicants: The Regents of the University of California, Oakland, CA (US); University of Washington, Seattle, WA (US)

(72) Inventors: Feroz R. Papa, San Francisco, CA (US); Bradley J. Backes, San Francisco, CA (US); Dustin J. Maly, Seattle, WA (US)

(73) Assignees: The Regents of the University of California, Oakland, CA (US); University of Washington, Seattle, WA (US)

( * ) Notice: Subject to any disclaimer, the term of this patent is extended or adjusted under 35 U.S.C. 154(b) by 0 days.

(21) Appl. No.: 17/525,764

(22) Filed: Nov. 12, 2021

(65) Prior Publication Data

US 2022/0153720 A1 May 19, 2022

Related U.S. Application Data

(60) Provisional application No. 63/113,543, filed on Nov. 13, 2020.

(51) Int. Cl.
*C07D 239/84* (2006.01)
*C07D 401/10* (2006.01)

(52) U.S. Cl.
CPC .................................. *C07D 401/10* (2013.01)

(58) Field of Classification Search
CPC ............................ C07D 239/84; A61K 31/517
USPC ........................................ 544/292; 514/266.4
See application file for complete search history.

(56) References Cited

U.S. PATENT DOCUMENTS

| | | | |
|---|---|---|---|
| 9,382,230 | B2 | 7/2016 | Walter et al. |
| 2010/0075967 | A1 | 3/2010 | Dixon et al. |
| 2018/0265497 | A1 | 9/2018 | Braun et al. |

FOREIGN PATENT DOCUMENTS

| | | | | |
|---|---|---|---|---|
| WO | WO2006039718 | * | 4/2006 | |
| WO | WO-2019/094641 A1 | | 5/2019 | |
| WO | WO-2020/047518 A1 | | 3/2020 | |
| WO | WO2020232401 | * | 11/2020 | C07D 239/84 |
| WO | WO2020232403 | * | 11/2020 | C07D 239/84 |
| WO | WO2020252165 | * | 12/2020 | C07D 401/12 |
| WO | WO-2022/104148 A1 | | 5/2022 | |

OTHER PUBLICATIONS

Calfon, M. et al. (Jan. 3, 2002). "IRE1 couples endoplasmic reticulum load to secretory capacity by processing the XBP-1 mRNA," *Nature* 415(6867):92-96.

Chan, C-P. et al. (Sep. 2006). "Modulation of the unfolded protein response by the severe acute respiratory syndrome coronavirus spike protein," *J Virol* 80(18):9279-9287.

Cox, J.S. et al. (Nov. 1, 1996). "A novel mechanism for regulating activity of a transcription factor that controls the unfolded protein response," *Cell* 87(3):391-404.

Feldman, H.C. et al. (Nov. 2021). "ATP-competitive partial antagonists of the IRE1α RNase segregate outputs of the UPR," *Nat Chem Biol* 17(11):1148-1156.

Feldman, H.C. et al. (Aug. 19, 2016). "Structural and Functional Analysis of the Allosteric Inhibition of IRE1α with ATP-Competitive Ligands," *ACS Chem Biol* 11(8):2195-2205.

Feldman, H.C et al. (Dec. 20, 2019). "Development of a Chemical Toolset for Studying the Paralog-Specific Function of IRE1," *ACS Chem Biol* 14(12):2595-2605.

Ghosh, R. et al. (Jul. 31, 2014). "Allosteric inhibition of the IRE1α RNase preserves cell viability and function during endoplasmic reticulum stress," *Cell* 158(3):534-548.

Gordon, D.E. et al. (Jul. 2020). "A SARS-COV-2 Protein Interaction Map Reveals Targets for Drug Repurposing," *Nature* 583(7816):459-468.

Han, D. et al. (Aug. 7, 2009). "IRE1α kinase activation modes control alternate endoribonuclease outputs to determine divergent cell fates," *Cell* 138(3):562-575.

Han, D. et al. (Jan. 25, 2008). "A kinase inhibitor activates the IRE1alpha RNase to confer cytoprotection against ER stress," *Biochem Biophys Res Commun* 365(4):777-783.

Hetz, C. et al. (Jan. 18, 2018). "The Unfolded Protein Response and Cell Fate Control," *Mol Cell* 69(2):169-181.

Hollien, J. et al. (Aug. 10, 2009). "Regulated Ire1-dependent decay of messenger RNAs in mammalian cells," *J Cell Biol* 186(3):323-331.

International Search Report dated Feb. 3, 2022, for PCT Application No. PCT/US2021/059255, filed Nov. 12, 2021, 3 pages.

Jan, C.H. et al. (Nov. 2014). "Principles of ER cotranslational translocation revealed by proximity-specific ribosome profiling," *Science* 346(6210):1257521.

Kawahara, T. et al. (Oct. 1997). "Endoplasmic reticulum stress-induced mRNA splicing permits synthesis of transcription factor Hac1 p/Ern4p that activates the unfolded protein response," *Mol Biol Cell* 8(10):1845-1862.

Kimmig, P. et al. (Oct. 15, 2012). "The unfolded protein response in fission yeast modulates stability of select mRNAs to maintain protein homeostasis," *eLife* 1:e00048.

Morita, S. et al. (Apr. 4, 2017). "Targeting ABL-IRE1α Signaling Spares ER-Stressed Pancreatic β Cells to Reverse Autoimmune Diabetes," *Cell Metabolism* 25(4):883-897.e8.

Papa, F.R. et al. (Nov. 28, 2003). "Bypassing a kinase activity with an ATP-competitive drug," *Science* 302(5650):1533-1537.

Plumb, R. et al. (May 20, 2015). "A functional link between the co-translational protein translocation pathway and the UPR," *eLife* 4:e07426.

Reimold, A.M. et al. (Jul. 19, 2001). "Plasma cell differentiation requires the transcription factor XBP-1," *Nature* 412(6844):300-307.

Sicari, D. et al. (Sep. 7, 2020). "Role of the early secretory pathway in SARS-COV-2 infection," *J Cell Biol* 219(9):e202006005.

(Continued)

*Primary Examiner* — Jeffrey H Murray

(74) *Attorney, Agent, or Firm* — Mintz, Levin, Cohn, Ferris, Glovsky and Popeo, P.C.

(57) ABSTRACT

Disclosed herein, inter alia, are substituted quinazolin-2-amines and isoquinolin-3-amines for inhibiting IRE1α and uses thereof.

17 Claims, 15 Drawing Sheets

Specification includes a Sequence Listing.

(56) References Cited

OTHER PUBLICATIONS

Thamsen, M. et al. (Jan. 9, 2019). "Small molecule inhibition of IRE1α kinase/RNase has anti-fibrotic effects in the lung," *PLoS One* 14(1):e0209824.
Walter, P. et al. (Nov. 2011). "The unfolded protein response: from stress pathway to homeostatic regulation," *Science* 334(6059):1081-1086.
Wang, L. et al. (Dec. 2012). "Divergent allosteric control of the IRE1α endoribonuclease using kinase inhibitors," *Nat Chem Biol* 8(12):982-989.
Written Opinion dated Feb. 3, 2022, for PCT Application No. PCT/US2021/059255, filed Nov. 12, 2021, 4 pages.
Yamashita, Y. et al. (Aug. 31, 2020). "Targeting Adaptive IRE1α Signaling and PLK2 in Multiple Myeloma: Possible Anti-Tumor Mechanisms of KIRA8 and Nilotinib," *Int J Mol Sci* 21(17):6314.

* cited by examiner

LBC-405 IRE1α $IC_{50}$ = 5.1 nM
Acts like a KIRA

Target-37

LBC-407 IRE1α $IC_{50}$ = 7.4 nM
Acts like a PAIR

Target-3

LBC-406 IRE1α $IC_{50}$ = 7.5 nM
Acts like a KIRA

Target-2

LBC-408 IRE1α $IC_{50}$ = 9.5 nM
Acts like a PAIR

Target-4

KIRA8 (potent KIRA)

KIRA 8

IRE1α $IC_{50}$= 14 nM

```
                    SEQUENCE LISTING

<160> NUMBER OF SEQ ID NOS: 20

<210> SEQ ID NO 1
```

```
<211> LENGTH: 17
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5-Alexa Fluor 647-labeled
<220> FEATURE:
<221> NAME/KEY: misc_feature
<222> LOCATION: (17)..(17)
<223> OTHER INFORMATION: 3-Iowa BlackFQ

<400> SEQUENCE: 1

cauguccgca gcgcaug                                                17

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 2

aaacagagta gcacagactg c                                           21

<210> SEQ ID NO 3
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 3

ggatctctaa gactagaggc ttggtg                                      26

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4

gcaaatgctt ctaggcggac                                             20

<210> SEQ ID NO 5
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 5

aagaaagggt gtaaaacgca gc                                          22

<210> SEQ ID NO 6
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 6

gtcctctggg agcccaag                                               18
```

-continued

<210> SEQ ID NO 7
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 7
acagagcctc caccagg 17

<210> SEQ ID NO 8
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 8
atcctctggg agccccgc 18

<210> SEQ ID NO 9
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 9
agagagcttc caccaag 17

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
caaggagctg caggagaaga 20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
gcctggttga agttctccac 20

<210> SEQ ID NO 12
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 12
tgaaaaacag agtagcagca caga 24

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
aagggaggct ggtaaggaac 20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
agttcaacgg cacagtcaag 20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
tactcagcac cagcatcacc 20

<210> SEQ ID NO 16
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 16
cgtctcgccc tgattcgt 18

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
ggaagttcag cccggtgatt 20

<210> SEQ ID NO 18
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 18
tggattggca tggtggaaaa c 21

<210> SEQ ID NO 19
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 19
tgtccagttc gatgctccg 19

<210> SEQ ID NO 20
<211> LENGTH: 8

-continued

<212> TYPE: PRT
<213> ORGANISM: Artificial Sequence
<220> FEATURE:
<223> OTHER INFORMATION: Synthetic polypeptide

<400> SEQUENCE: 20

Asp Tyr Lys Asp Asp Asp Asp Lys
1               5

IRE1α INHIBITORS AND USES THEREOF

CROSS-REFERENCES TO RELATED APPLICATIONS

This application claims the benefit of U.S. Provisional Application No. 63/113,543, filed Nov. 13, 2020, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant nos. U01 DK123609 and R01 DK100623 awarded by The National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-699001US_Sequence_Listing_ST25.TXT, created Nov. 9, 2021, 4,439 bytes, machine format IBM-PC, MS Windows operating system, is hereby incorporated by reference.

BACKGROUND

During mammalian cell growth and differentiation, the unfolded protein response (UPR) homeostatically adjusts endoplasmic reticulum (ER) protein-folding capacity to match changing cellular secretory demands. However, under high/chronic ER stress conditions the UPR triggers apoptosis. This dichotomy is promoted by differential activation levels of the ER transmembrane kinase/endoribonuclease (RNase) IRE1α. IRE1α kinase auto-phosphorylation operates as a rheostat to control downstream RNase-induced outputs that either sustain adaptive ER protein-folding or cause apoptosis. The IRE1α RNase can be controlled allosterically by kinase inhibitors that at maximal occupancy either fully inactivate or activate the RNAse. Overwhelming of protein folding and structural maturation in the early secretory pathway leads to accumulation of misfolded and immature secretory proteins in the endoplasmic reticulum (ER) (PMIDs: 22116877). Eukaryotic cells evolved intracellular signaling pathways to respond to such "ER stress". These "Unfolded Protein Response" (UPR) pathways maintain cellular secretory function and physiological healthR in the face of remediable ER stress (PMIDs: 29107536). First discovered in unicellular eukaryotes, UPR pathways promote homeostatic/adaptive outputs through transcriptional upregulation of ER protein-folding and quality-control factors that extract terminally misfolded proteins back to the cytosol for degradation. However, in mammalian cells experiencing ER stress levels that cannot be mitigated by these adaptive arms, the UPR triggers programmed cell death (PCD), typically through mitochondrial apoptosis (PMIDs: 29107536). Multi-cellular organisms may benefit from culling irreversibly ER-stressed cells because the protein cargo that surviving cells continue to secrete is more likely to be pristine. However, in chronic states of such "terminal" UPR activation, the large-scale decrement of cells through unchecked PCD may actively promote cell degenerative diseases, such as diabetes mellitus (PMCID 5568783). One critical life-death switch in the UPR is governed by the ER transmembrane multi-domain sensor protein, IRE1α. IRE1α is activated upon ER stress elevation, causing this sensor to self-associate in the ER membrane. This event causes IRE1α's cytosolic Ser/Thr kinase to trans auto-phosphorylate, which results in subsequent activation of its C-terminal endoribonuclease (RNase) catalytic domain. The range of available IRE1α RNase activation states runs a gamut from the inactive, the active, to the hyperactive, with the level of activity controlled rheostatically by the upstream kinase module. From its inactive monomeric state, low-level kinase/RNase activation (caused by dimerization) initiates (adaptive) XBP1 mRNA transcription factor frame-shift splicing, while high-level kinase/RNase hyperactivation (due to homo-oligomerization) expands the RNase substrate repertoire to myriad ER-localized mRNAs that become endonucleolytically cleaved (in a process termed RIDD), (PMCIDs: 2762408, 4244221), thus initiating apoptosis. Thus, for maintaining cellular homeostasis, apriori, the "sweet spot" for IRE1α RNase activation may lie at a level wherein XBP1 mRNA splicing remains permissible, but without the initiation of RIDD. The cellular effects of such a meta-stable activation state have even been demonstrated with IRE1α mutants (some found naturally as somatic mutations in cancers that act as RNase hypomorphs) and chemical-genetic ("bumped inhibitor/holed kinase") systems (PMIDs: 25018104 and 19665977). But while it has been established that ATP-competitive inhibitors can control endogenous IRE1α's RNase activity through the kinase domain, these allosteric modulators have largely been shown to enforce opposite extremes of activation states (PMID 23086298). Therefore, an optimal mode of engaging endogenous IRE1α's ATP-binding site has hitherto been unachievable. Disclosed herein, inter alia, are solutions to these and other problems known in the art.

BRIEF SUMMARY

In an aspect is provided a compound having the formula:

(I)

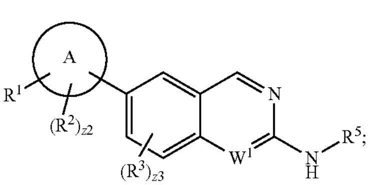

wherein, Ring A is cycloalkyl, heterocycloalkyl, aryl, or heteroaryl; $R^1$ is $-NR^{1A}SO_2R^{1B}$, $-NR^{1A}SOR^{1B}$, $-SOR^{1B}$, $-SO_2R^{1B}$, $-SONR^{1A}R^{1B}$, $-SO_2NR^{1A}R^{1B}$, $-NHC(O)NR_{1A}R^{1B}$, $-NR^{1A}R^{1B}$, $-C(O)R^{1B}$, $-OC(O)R^{1B}$, $-C(O)OR^{1B}$, $-C(O)NR^{1A}R^{1B}$, $-OR^{1B}$, $-NR^{1A}C(O)R^{1B}$, $-NR^{1A}C(O)OR^{1B}$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl; $R^{1A}$ and $R^{1B}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$ substituents bonded to the same nitrogen atom may optionally be joined to form a substituted or unsubstituted heterocycloalkyl; $R^2$ is independently oxo, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl; z2 is an integer from 0 to 4; $R^3$ is independently halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NR^{3C}NR^{3A}R^{3B}$, $—ONR^{3A}R^{3B}$, $—NHC(O)NR^{3A}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl; z3 is independently an integer from 0 to 4; $W^1$ is —N═, —CH═, or $—CR^3═$; $R^5$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$, $R^{2B}$, $R^{2C}$, $R^{2D}$, $R^{3A}$, $R^{3B}$, $R^{3C}$, and $R^{3D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $X^2$ and $X^3$ are independently —F, —Cl, —Br, or —I; n2 and n3 are independently an integer from 0 to 4; and m2, m3, v2, and v3 are independently 1 or 2; or a salt thereof.

In an aspect is provided a pharmaceutical composition including a compound described herein, or a salt thereof, and a pharmaceutically acceptable excipient.

In an aspect is provided a method of treating a cell degenerative disease in a subject in need thereof, the method including administering to the subject in need thereof an effective amount of a compound described herein, or a salt thereof.

In an aspect is provided a method of inhibiting cancer growth in a subject in need thereof, the method including administering to the subject in need thereof an effective amount of a compound described herein, or a salt (e.g., pharmaceutically acceptable salt) thereof.

In an aspect is provided a method of treating a cancer in a subject in need thereof, the method including administering to the subject in need thereof an effective amount of a compound described herein, or a salt (e.g., pharmaceutically acceptable salt) thereof.

BRIEF DESCRIPTION OF THE DRAWINGS

FIG. 1A: Cartoon model of predicted monomer-dimer equilibriums of different phosphorylation states of IRE1α in the presence of different ATP-competitive inhibitors treatment conditions. FIG. 1B: Top: Recombinant constructs of IRE1α*, residues 547-977 of IRE1α, include the cytosolic kinase and RNase domains. Dephosphorylated IRE1α*, dpIRE1α*, is generated from IRE1α* via treatment with lambda phosphatase. Bottom: Schematic of the in vitro XBP1-mini substrate cleavage assay. FIG. 1C: Dimerization affinity (Kaimer) curves for apo IRE1α* (black squares) and apo dpIRE1α* (gray circles). Data points shown are the mean±SEM, n=3. FIG. 1D: Kaimer curve for the dpIRE1α*-AT9283 complex (top curve). Data points shown are the mean±SEM, n=3. The $K_{dimer}$ curve of apo dpIRE1α* (bottom curve) from FIG. 1C is shown for comparison. FIG. 1E: Kaimer curves for the IRE1α*-AT9283 and IRE1α*-KIRA8 complexes. Data points shown are shown as the mean±SEM, n=3. The Kaimer curve of apo IRE1α* (dark gray) from FIG. 1C is shown for comparison.

FIG. 6A: Quantification of spliced XBP1 in untreated INS-1 cells and INS-1 cells treated with brefeldin A (BFA) or BFA and KIRA8. Values shown are mean±SEM, n=3. FIG. 6B: Representative example of an EtBr-stained agarose gel of XBP1 cDNA amplicons from INS-1 cells subjected to the conditions described in FIG. 6A. FIG. 6C: Quantification of spliced XBP1 in untreated INS-1 cells and INS-1 cells treated with thapsigargin (Tg) or Tg and KIRA8. Values shown are mean±SEM, n=3. FIG. 6D: Representative example of an EtBr-stained agarose gel of XBP1 cDNA amplicons from INS-1 cells subjected to the conditions described in FIG. 6C.

DETAILED DESCRIPTION

I. Definitions

Figure 1A:
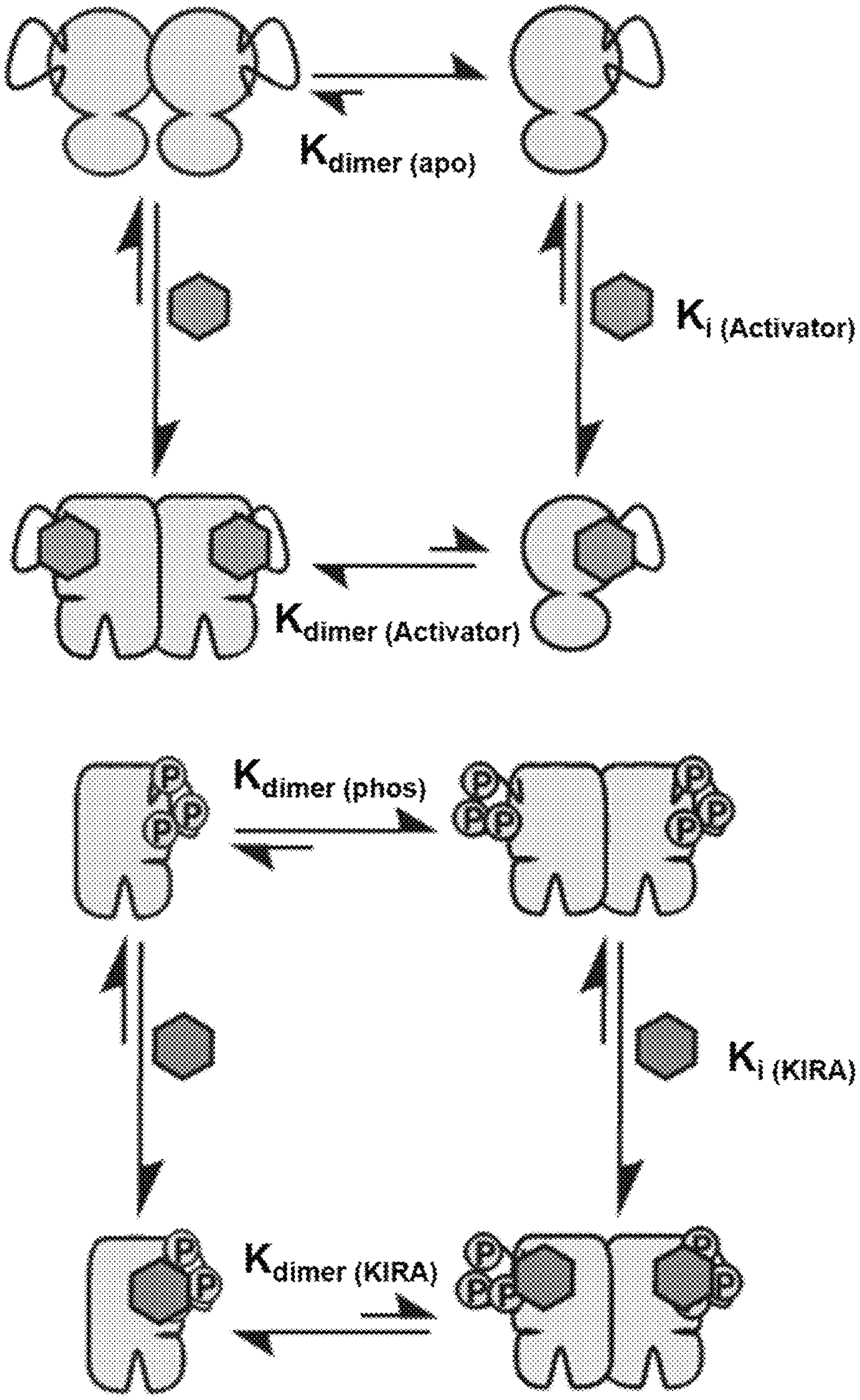
FIGS. 1A-1E. IRE1α dimerization is controlled by phosphorylation and ATP-binding site occupancy.
Figure 1B:
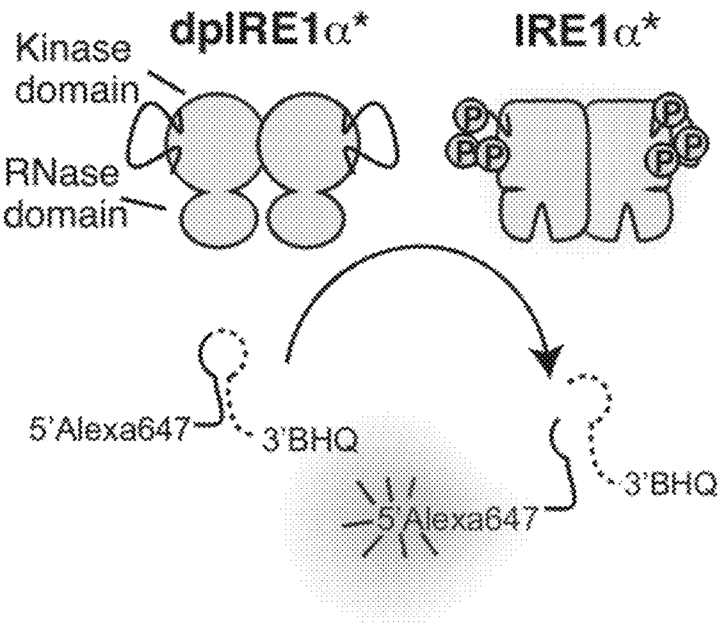

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain.

Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker ($-O-$). An alkyl moiety may be an alkenyl moiety. An alkyl moiety may be an alkynyl moiety. An alkenyl includes one or more double bonds. An alkynyl includes one or more triple bonds.

The term "alkylene," by itself or as part of another substituent, means, unless otherwise stated, a divalent radical derived from an alkyl, as exemplified, but not limited by, $-CH_2CH_2CH_2CH_2-$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-S-CH_2$, $-S(O)-CH_3$, $-CH_2-CH_2-S(O)_2-CH_3$, $-CH=CHO-CH_3$, $-Si(CH_3)_3$, $-CH_2-CH=N-OCH_3$, $-CH=CH-N(CH_3)-CH_3$, $-O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$.

A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term “heteroalkenylene,” by itself or as part of another substituent, means, unless otherwise stated, a divalent radical derived from a heteroalkene. The term “heteroalkynylene” by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms “cycloalkyl” and “heterocycloalkyl,” by themselves or in combination with other terms, mean, unless otherwise stated, cyclic versions of “alkyl” and “heteroalkyl,” respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A “cycloalkylene” and a “heterocycloalkylene,” alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term “cycloalkyl” means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. A bicyclic or multicyclic cycloalkyl ring system refers to multiple rings fused together or multiple spirocyclic rings wherein at least one of the fused or spirocyclic rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term “cycloalkenyl” is used in accordance with its plain ordinary meaning. In embodiments, a cycloalkenyl is a monocyclic, bicyclic, or a multicyclic cycloalkenyl ring system. A bicyclic or multicyclic cycloalkenyl ring system refers to multiple rings fused together or multiple spirocyclic rings wherein at least one of the fused or spirocyclic rings is a cycloalkenyl ring and wherein the multiple rings are attached to the parent molecular moiety through any carbon atom contained within a cycloalkenyl ring of the multiple rings.

In embodiments, the term “heterocycloalkyl” means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together or multiple spirocyclic rings wherein at least one of the fused or spirocyclic rings is a heterocycloalkyl ring and wherein the multiple rings are attached to the parent molecular moiety through any atom contained within a heterocycloalkyl ring of the multiple rings.

The terms “halo” or “halogen,” by themselves or as part of another substituent, mean, unless otherwise stated, a fluorine, chlorine, bromine, or iodine atom. Additionally, terms such as “haloalkyl” are meant to include monohaloalkyl and polyhaloalkyl. For example, the term “halo($C_1$-$C_4$) alkyl” includes, but is not limited to, fluoromethyl, difluoromethyl, trifluoromethyl, 2,2,2-trifluoroethyl, 4-chlorobutyl, 3-bromopropyl, and the like.

The term “acyl” means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term “aryl” means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term “heteroaryl” refers to aryl groups (or rings) that contain at least one heteroatom such as N, O, or S, wherein the nitrogen and sulfur atoms are optionally oxidized, and the nitrogen atom(s) are optionally quaternized. Thus, the term “heteroaryl” includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An “arylene” and a “heteroarylene,” alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〰" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula $—S(O_2)—R'$, where R' is a substituted or unsubstituted alkyl group as defined above. R' may have a specified number of carbons (e.g., "$C_1$-$C_4$ alkylsulfonyl").

The term "alkylarylene" as an arylene moiety covalently bonded to an alkylene moiety (also referred to herein as an alkylene linker). In embodiments, the alkylarylene group has the formula:

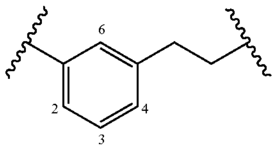

or

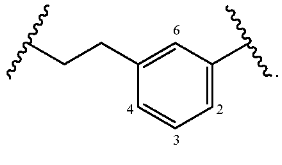

.

An alkylarylene moiety may be substituted (e.g. with a substituent group) on the alkylene moiety or the arylene linker (e.g., at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3$, $—SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', -halogen, —SiR'R"R"', —OC(O)R', —C(O)R', $—CO_2R'$, —CONR'R", —OC(O)NR'R", —NR"C(O)R', —NR'—C(O)NR"R"', $—NR"C(O)_2R'$, —NR—C(NR'R"R"')═NR"", —NR—C(NR'R")═NR"', —S(O)R', $—S(O)_2R'$, $—S(O)_2NR'R"$, $—NRSO_2R'$, —NR'NR"R"', —ONR'R", —NR'C(O)NR"NR"'R"", —CN, $—NO_2$, $—NR'SO_2R"$, —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', $—CO_2R'$, —CONR'R", —OC(O)NR'R", —NR"C(O)R', —NR'—C(O)NR"R"', $—NR"C(O)_2R'$, —NR—C(NR'R"R"')═NR"", —NR—C(NR'R")═NR"', —S(O)R', $—S(O)_2R'$, $—S(O)_2NR'R"$, $—NRSO_2R'$, —NR'NR"R"', —ONR'R", —NR'C(O)NR"NR"'R"", —CN, $—NO_2$, —R', $—N_3$, $—CH(Ph)_2$, fluoro($C_1$-$C_4$)alkoxy, and fluoro($C_1$-$C_4$)alkyl, $—NR'SO_2R"$, —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)-(CRR')_q-U-$, wherein T and U are independently $-NR-$, $-O-$, $-CRR'-$, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently $-CRR'-$, $-O-$, $-NR-$, $-S-$, $-S(O)-$, $-S(O)_2-$, $-S(O)_2NR'-$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s-X'-(C''R''R''')_d-$, where s and d are independently integers of from 0 to 3, and X is $-O-$, $-NR'-$, $-S-$, $-S(O)-$, $-S(O)_2-$, or $-S(O)_2NR'-$. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L.1.1}$, $L^2$ may be substituted with one or more first substituent groups denoted by $R^{L2.1}$, $L^3$ may be substituted with one or more first substituent groups denoted by $R^{L3.1}$, $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ . . . $R^{100.1}$; $R^{1A.1}$, $R^{2A.1}$, $R^{3A.1}$, $R^{4A.1}$, $R^{5A.1}$ . . . $R^{100A.1}$; $R^{L1.1}$, $R^{L2.1}$, $R^{L3.1}$, $R^{L4.1}$, $R^{L5.1}$ . . . $R^{L100.1}$) may be further substituted with one or more second substituent groups (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$) may be further substituted with one or more third substituent groups (e.g., $R^{1.3}$, $R^{2.3}$, $R^{3.3}$, $R^{4.3}$, $R^{5.3}$ . . . $R^{100.3}$; $R^{1A.3}$, $R^{2A.3}$, $R^{3A.3}$, $R^{4A.3}$, $R^{5A.3}$ . . . $R^{100A.3}$; $R^{L1.3}$, $R^{L2.3}$, $R^{L3.3}$, $R^{L4.3}$, $R^{L5.3}$ . . . $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

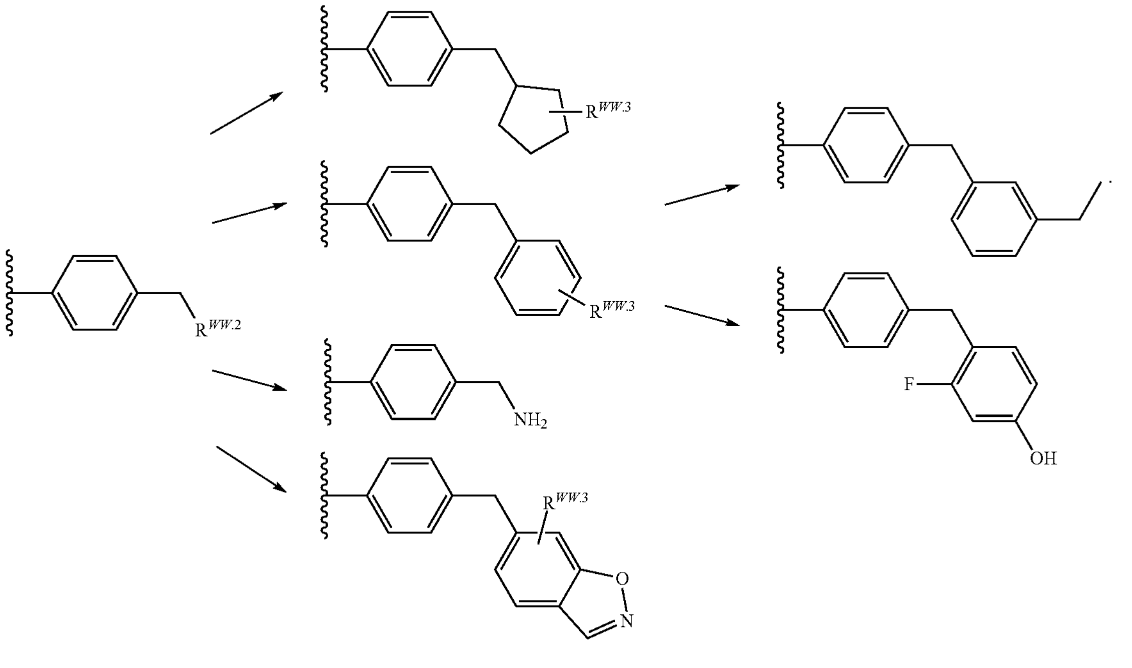

$R^{WW.1}$ is independently oxo, halogen, —$CX^{WW.1}_3$, —$CHX^{WW.1}_2$, —$CH_2X^{WW.1}$, —$OCX^{WW.1}_3$, —$OCH_2X^{WW.1}$, —$OCHX^{WW.1}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, —$CX^{WW.1}_3$, —$CHX^{WW.1}_2$, —$CH_2X^{WW.1}$, —$OCX^{WW.1}_3$, —$OCH_2X^{WW.1}$, —$OCHX^{WW.1}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, —$CX^{WW.2}_3$, —$CHX^{WW.2}_2$, —$CH_2X^{WW2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, —$CX^{WW.3}_3$, —$CHX^{WW.3}_2$, —$CH_2X^{WW.3}$, —$OCX^{WW.3}_3$, —$OCH_2X^{WW.3}$, —$OCHX^{WW.3}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g., substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R10^{0B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2XL^{WW.1}$, —$OCHX^{LWW.1}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, —$CX^{LWW.1}_3$, —$CHX^{LWW.1}_2$, $—CH_2X^{LWW.1}$, $—OCX^{LWW.1}{}_3$, $—OCH_2XL^{WW.1}$, $—OCHX^{LWW.1}{}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, $—CX^{LWW.2}{}_3$, $—CHX^{LWW.2}{}_2$, $—CH_2XL^{WW2}$, $—OCX^{LWW.2}{}_3$, $—OCH_2XL^{WW.2}$, $—OCHX^{LWW.2}{}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, $—CX^{LWW.2}{}_3$, $—CHX^{LWW.2}{}_2$, $—CH_2X^{LWW.2}$, $—OCX^{LWW.2}{}_3$, $—OCH_2XL^{WW.2}$, $—OCHX^{LWW.2}{}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, $—CX^{LWW.3}{}_3$, $—CHX^{LWW.3}{}_2$, $—CH_2X^{LWW.3}$, $—OCX^{LWW.3}{}_3$, $—OCH_2XL^{WW.3}$, $—OCHX^{LWW.3}{}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, $—CX^{WW3}$, $—CHX^{WWZ}$, $—CH_2X_{WW}$, $—OCX^{WW}{}_3$, $—OCH_2X^{WW}$, $—OCHX^{WW}{}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, —O—, —NH—, —C(O)—, —C(O)NH—, —NHC(O)—, —NHC(O)NH—, —NHC(NH)NH—, —C(O)O—, —OC(O)—, —S—, $—SO_2—$, $—SO_2NH—$, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refers to the resulting association between atoms or molecules of "bioconjugate reactive groups" or "bioconjugate reactive moieties". The association can be direct or indirect. For example, a conjugate between a first bioconjugate reactive group (e.g., —$NH_2$, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido or maleimide groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold, or react with maleimides;
(h) amine or sulfhydryl groups (e.g., present in cysteine), which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding;
(m) metal bonding to reactive phosphorus groups (e.g. phosphines) to form, for example, phosphate diester bonds;
(n) azides coupled to alkynes using copper catalyzed cycloaddition click chemistry; and
(o) biotin conjugate can react with avidin or streptavidin to form an avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13.A}$, $R^{13.B}$, $R^{13.C}$, $R^{13.D}$, etc., wherein each of $R^{13.A}$, $R^{13.B}$, $R^{13.C}$, $R^{13D}$, etc. is defined within the scope of the definition of $R^{13}$ and optionally differently.

A "detectable agent" or "detectable moiety" is a composition, substance, element, or compound; or moiety thereof; detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Ph$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, and $^{225}Ac$. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or $—CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The terms "bind" and "bound" as used herein is used in accordance with its plain and ordinary meaning and refers to the association between atoms or molecules. The association can be direct or indirect. For example, bound atoms or molecules may be bound, e.g., by covalent bond, linker (e.g., a first linker or second linker), or non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like).

The term "capable of binding" as used herein refers to a moiety (e.g. a compound as described herein) that is able to measurably bind to a target. In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments, contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g., increasing) the activity or function of the protein relative to the activity or function of the protein in the absence of the activator. In embodiments activation means positively affecting (e.g., increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In embodiments inhibition means negatively affecting (e.g., decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease means that the disease (e.g., cancer, cell degeneration disease) is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g., proteins, nucleic acids, small molecules, ions, lipids) that conveys a change in one component to one or more other components, which in turn may convey a change to additional components, which is optionally propagated to other signaling pathway components.

In this disclosure, "comprises," "comprising," "containing" and "having" and the like can have the meaning ascribed to them in U.S. patent law and can mean "includes," "including," and the like. "Consisting essentially of or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The terms “disease” or “condition” refer to a state of being or health status of a patient or subject capable of being treated with the compounds or methods provided herein. The disease may be a cancer. In some further instances, “cancer” refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin’s lymphomas (e.g., Burkitt’s, Small Cell, and Large Cell lymphomas), Hodgkin’s lymphoma, leukemia (including AML, ALL, and CML), or multiple myeloma. In embodiments, the disease is a cell degeneration disease.

As used herein, the term “cancer” refers to all types of cancer, neoplasm or malignant tumors found in mammals (e.g., humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin’s Disease, and Non-Hodgkin’s Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term “leukemia” refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, acute lymphoblastic leukemia (ALL), chronic lymphocytic leukemia (CLL), acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, acute myeloid leukemia (AML), chronic myeloid leukemia (CML), leukemia cutis, embryonal leukemia, eosinophilic leukemia, Gross’ leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myelodysplastic syndrome (MDS), myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling’s leukemia, stem cell leukemia, subleukemic leukemia, or undifferentiated cell leukemia.

As used herein, the term “lymphoma” refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin’s disease. Hodgkin’s disease represents approximately 15% of all diagnosed lymphomas. This is a cancer associated with Reed-Sternberg malignant B lymphocytes. Non-Hodgkin’s lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma (MCL), follicular lymphoma, marginal zone B-cell lymphoma (MZL), mucosa-associated lymphatic tissue lymphoma (MALT), extranodal lymphoma, nodal (monocytoid B-cell) lymphoma, splenic lymphoma, diffuse large cell B-lymphoma (DLBCL), activated B-cell subtype diffuse large B-cell lymphoma (ABC-DBLCL), germinal center B-cell like diffuse large B-cell lymphoma, Burkitt’s lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungocides, and precursor T-lymphoblastic lymphoma.

The term “sarcoma” generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy’s sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms’ tumor sarcoma, endometrial sarcoma, stromal sarcoma, Ewing’s sarcoma, fascial sarcoma, fibroblastic sarcoma, giant cell sarcoma, granulocytic sarcoma, Hodgkin’s sarcoma, idiopathic multiple pigmented hemorrhagic sarcoma, immunoblastic sarcoma of B cells, lymphoma, immunoblastic sarcoma of T-cells, Jensen’s sarcoma, Kaposi’s sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment (e.g., the patient has a disease, the patient suffers from a disease).

The term "prevent" refers to a decrease in the occurrence of disease symptoms or disease in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g., to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "Ire1" or "Ire1α" or "ERN1" refers to the protein "Serine/threonine-protein kinase/endoribonuclease IRE1" also known as "Endoplasmic reticulum to nucleus signaling 1". In embodiments, "Ire1" or "Ire1α" or "ERN1" refers to the human protein. Included in the term "Ire1" or "Ire1α" or "ERN1" are the wildtype and mutant forms of the protein. In embodiments, "Ire1" or "Ire1α" or "ERN1" refers to the protein associated with Entrez Gene 2081, OMIM 604033, UniProt O75460, and/or RefSeq (protein) NM_001433. In embodiments, the reference numbers immediately above refer to the protein, and associated nucleic acids, known as of the date of filing of this application. In embodiments, "Ire1" or "Ire1α" or "ERN1" refers to the wildtype human protein. In embodiments, "Ire1" or "Ire1α" or "ERN1" refers to the wildtype human nucleic acid.

The compounds described herein can be used in combination with one another, with other active agents known to be useful in treating a disease associated with cells expressing a disease associated cellular component, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with anti-cancer agents or conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin, etc.), and the like.

In therapeutic use for the treatment of a disease, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer, or with adjunctive agents that may not be effective alone, but may contribute to the efficacy of the active agent.

"Anti-cancer agent" is used in accordance with its plain ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. In embodiments, an anti-cancer agent is an agent with antineoplastic properties that has not (e.g., yet) been approved by the FDA or similar regulatory agency of a country other than the USA, for treating cancer. In embodiments, an anti-cancer agent is an inhibitor of K-Ras, RAF, MEK, Erk, PI3K, Akt, RTK, or mTOR. In embodiments, an anti-cancer agent is an MDM2 inhibitor or a genotoxic anti-cancer agent. In embodiments, an anti-cancer agent is nutlin-1, nutlin-2, nutlin-3, nutlin-3a, nutlin-3b, YH239-EE, MI-219, MI-773, MI-77301, MI-888, MX69, RG7112, RG7388, RITA, idasanutlin, DS-3032b, or AMG232. In embodiments, an anti-cancer agent is an alkylating agent, intercalating agent, or DNA replication inhibitor. Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g., U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRATL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-S—azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g., Taxol™ (i.e. paclitaxel), Taxotere™, compounds comprising the taxane skeleton, Erbulozole (i.e., R-55104), Dolastatin 10 (i.e., DLS-10 and NSC-376128), Mivobulin isethionate (i.e., as CI-980), Vincristine, NSC-639829, Discodermolide (i.e., as NVP-XX-A-296), ABT-751 (Abbott, i.e., E-7010), Altorhyrtins (e.g., Altorhyrtin A and Altorhyrtin C), Spongistatins (e.g., Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e., LU-103793 and NSC-D-669356), Epothilones (e.g., Epothilone A, Epothilone B, Epothilone C (i.e., desoxyepothilone A or dEpoA), Epothilone D (i.e., KOS-862, dEpoB, and desoxyepothilone B), Epothilone E, Epothilone F, Epothilone B N-oxide, Epothilone A N-oxide, 16-aza-epothilone B, 21-aminoepothilone B (i.e., BMS-310705), 21-hydroxyepothilone D (i.e., Desoxyepothilone F and dEpoF), 26-fluoroepothilone, Auristatin PE (i.e., NSC-654663), Soblidotin (i.e., TZT-1027), LS-4559-P (Pharmacia, i.e., LS-4577), LS-4578 (Pharmacia, i.e., LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e., ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e., LY-355703), AC-7739 (Ajinomoto, i.e., AVE-8063A and CS-39.HCl), AC-7700 (Ajinomoto, i.e., AVE-8062, AVE-8062A, CS-39-L-Ser·HCl, and RPR-258062A), Vitilevuamide, Tubulysin A, Canadensol, Centaureidin (i.e., NSC-106969), T-138067 (Tularik, i.e., T-67, TL-138067 and TI-138067), COBRA-1 (Parker Hughes Institute, i.e., DDE-261 and WHI-261), H10 (Kansas State University), H16 (Kansas State University), Oncocidin A1 (i.e., BTO-956 and DIME), DDE-313 (Parker Hughes Institute), Fijianolide B, Laulimalide, SPA-2 (Parker Hughes Institute), SPA-1 (Parker Hughes Institute, i.e., SPIKET-P), 3-IAABU (Cytoskeleton/Mt. Sinai School of Medicine, i.e., MF-569), Narcosine (also known as NSC-5366), Nascapine, D-24851 (*Asta Medica*), A-105972 (Abbott), Hemiasterlin, 3-BAABU (Cytoskeleton/Mt. Sinai School of Medicine, i.e., MF-191), TMPN (Arizona State University), Vanadocene acetylacetonate, T-138026 (Tularik), Monsatrol, lnanocine (i.e., NSC-698666), 3-IAABE (Cytoskeleton/Mt. Sinai School of Medicine), A-204197 (Abbott), T-607 (Tuiarik, i.e., T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (*Asta Medica*), D-68144 (*Asta Medica*), Diazonamide A, A-293620 (Abbott), NPI-2350 (Nereus), Taccalonolide A, TUB-245 (Aventis), A-259754 (Abbott), Diozostatin, (−)-Phenylahistin (i.e., NSCL-96F037), D-68838 (Asta *Medica*), D-68836 (*Asta Medica*), Myoseverin B, D-43411 (Zentaris, i.e., D-81862), A-289099 (Abbott), A-318315 (Abbott), HTI-286 (i.e., SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to mIn, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. A moiety of an anti-cancer agent is a monovalent anti-cancer agent (e.g., a monovalent form of an agent listed above).

"Chemotherapeutic" or "chemotherapeutic agent" is used in accordance with its plain ordinary meaning and refers to a chemical composition or compound having antineoplastic properties or the ability to inhibit the growth or proliferation of cells.

"Anti-diabetic agent" or "antidiabetic agent" is used in accordance with its plain ordinary meaning and refers to a composition (e.g., compound, drug, antagonist, inhibitor, modulator) having the ability to lower blood glucose levels in a subject. In some embodiments, an anti-diabetic agent is an agent identified herein having utility in methods of treating diabetes.

In some embodiments, an anti-diabetic agent is an agent approved by the FDA or similar regulatory agency of a country other than the USA, for treating diabetes. Examples of anti-diabetic agents include, but are not limited to, insulin, insulin sensitizers (e.g., biguanides (e.g., metformin, phenformin, or buformin), thiazolidinediones (e.g., rosiglitazone, pioglitazone, troglitazone)), secretagogues (e.g., sulfonylureas (e.g., tolbutamide, acetohexamide, tolazamide, chlorpropamide, glipizide, glyburide, glibenclamide, glimepiride, gliclazide, glycopyramide, gliquidone), meglitinides (e.g., repaglinide, nateglinide)), alpha-glucosidase inhibitors (e.g., miglitol, acarbose, voglibose), peptide analog antidiabetic agents (e.g., incretins (glucagon-like peptide-1, gastric inhibitory peptide), glucagon-like peptide agonists (e.g., exenatide, liraglutide, taspoglutide), gastric inhibitoty peptide analogs, or dipeptidyl peptidase-4 inhibitors (e.g., vildagliptin, sitagliptin, saxagliptin, linagliptin, allogliptin, septagliptin), amylin agonist analogues (e.g., pramlintide).

As used herein, the term "neurodegenerative disorder" or "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes *dorsalis*.

As used herein, the term "cell degenerative disorder" or "cell degenerative disease" refers to a disease or condition wherein cells (e.g., specific sub-type of cells) of a subject became impaired (e.g., a function of the cell becomes impaired or aberrant) or the cells die in greater numbers or at an increased rate or are reduced in number at a greater rate or to a lower amount compared to a subject that does not possess the cell degenerative disorder or disease. Examples of a cell degenerative disease or disorder include, but are not limited to, neurodegenerative diseases, diabetes (type I or type II), retinal degeneration, or pulmonary fibrosis.

II. Compounds

In an aspect is provided a compound having the formula:

(I)

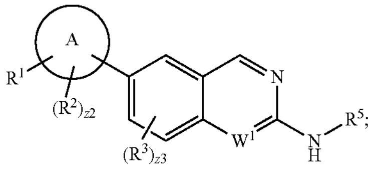

wherein, Ring A is cycloalkyl, heterocycloalkyl, aryl, or heteroaryl; $R^1$ is —$NR^{1A}SO_2R^{1B}$, —$NR^{1A}SOR^{1B}$, —$SOR^{1B}$, —$SO_2R^{1B}$, —$SONR^{1A}R^{1B}$, 13 $SO_2NR^{1A}R^{1B}$, —$NHC(O)NR^{1A}R^{1B}$, —$NR^{1A}R^{1B}$, —$C(O)R^{1B}$, —$OC(O)R^{1B}$, —$C(O)OR^{1B}$, —$C(O)NR^{1A}R^{1B}$, —$OR^{1B}$, —$NR^{1A}C(O)R^{1B}$, —$NR^{1A}C(O)OR^{1B}$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$ substituents bonded to the same nitrogen atom may optionally be joined to form a substituted or unsubstituted heterocycloalkyl; $R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, $NR^{2C}NR^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —C(O)—$OR^{2C}$, —$C(O)NR^{2A}R^{2B}$, —$OR^{2D}$, —$NR_{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl; z2 is an integer from 0 to 4; $R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, $SO_{v3}NR^{3A}R^{3B}$, —$NR^{3C}NR^{3A}R^{3B}$, —$ONR^{3A}R^{3B}$, —$NHC(O)NR^{3C}NR^{3A}R^{3B}$, —$NHC(O)NR^{3A}R^{3B}$, —$N(O)_{m3}$, —$NR^{3A}R^{3B}$, —$C(O)R^{3C}$, —C(O)—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl; z3 is an integer from 0 to 4; $W^1$ is —N═, —CH═, or —$CR^3$═; $R^5$ is —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$, $R^{2B}$, $R^{2C}$, $R^{2D}$, $R^{3A}$, $R^{3B}$, $R^{3C}$, and $R^{3D}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $X^2$ and $X^3$ are independently —F, —Cl, —Br, or —I; n2 and n3 are independently an integer from 0 to 4; and m2, m3, v2, and v3 are independently 1 or 2; or a salt thereof.

In embodiments, the compound has the formula:

(I)

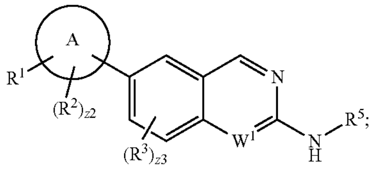

wherein, Ring A is cycloalkyl, heterocycloalkyl, aryl, or heteroaryl; $R^1$ is —$NR^{1A}SO_2R^{1B}$, —$NR^{1A}SOR^{1B}$, —$SOR^{1B}$, —$SO_2R^{1B}$, —$SONR^{1A}R^{1B}$, —$SO_2NR^{1A}R^{1B}$, —$NHC(O)NR^{1A}R^{1B}$, —$NR^{1A}R^{1B}$, —$C(O)R^{1B}$, —$OC(O)R^{1B}$, —$C(O)OR^{1B}$, —$C(O)NR^{1A}R^{1B}$, —$OR^{1B}$, —$NR^{1A}C(O)R^{1B}$, —$NR^{1A}C(O)OR^{1B}$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$ substituents bonded to the same nitrogen atom may optionally be joined to form a substituted or unsubstituted heterocycloalkyl; $R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, $NR^{2C}NR^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —C(O)—$OR^{2C}$, —$C(O)NR^{2A}R^{2B}$, —$OR^{2D}$, —$NR_{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl; z2 is an integer from 0 to 4; $R^3$ is independently halogen, $-CX^3_3$, $-CHX^3_2$, $-CH_2X^3$, $-OCX^3_3$, $-OCH_2X^3$, $-OCHX^3_2$, —CN, $-SO_{n3}R^{3D}$, $SO_{v3}NR^{3A}R^{3B}$, $-NR^{3C}NR^{3A}R^{3B}$, $-ONR^{3A}R^{3B}$, $-NHC(O)NR^{3C}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl; z3 is an integer from 0 to 4; $W^1$ is —N═, —CH═, or $-CR^3═$; $R^5$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$, $R^{2B}$, $R^{2C}$, $R^{2D}$, $R^{3A}$, $R^{3B}$, $R^{3C}$, and $R^{3D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, $-NH_2$, —COOH, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $X^2$ and $X^3$ are independently —F, —Cl, —Br, or —I; n2 and n3 are independently an integer from 0 to 4; and m2, m3, v2, and v3 are independently 1 or 2; or a salt thereof.

In an aspect is provided a compound having the formula:

(I)

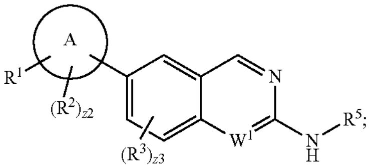

wherein, Ring A is cycloalkyl, heterocycloalkyl, aryl, or heteroaryl; $R^1$ is $-NR^{1A}SO_2R^{1B}$, $-NR^{1A}SOR^{1B}$, $-SOR^{1B}$, $-SO_2R^{1B}$, $-SONR^{1A}R^{1B}$, $-SO_2NR^{1A}R^{1B}$, $-NHC(O)NR^{1A}R^{1B}$, $-NR^{1A}R^{1B}$, $-C(O)R^{1B}$, $-OC(O)R^{1B}$, $-C(O)OR^{1B}$, $-C(O)NR^{1A}R^{1B}$, $-OR^{1B}$, $-NR^{1A}C(O)R^{1B}$, $-NR^{1A}C(O)OR^{1B}$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl; $R^{1A}$ and $R^{1B}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, $-NH_2$, —COOH, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$ substituents bonded to the same nitrogen atom may optionally be joined to form a substituted or unsubstituted heterocycloalkyl; $R^2$ is independently oxo, halogen, $-CX^2_3$, $-CHX^2_2$, $-CH_2X^2$, $-OCX^2_3$, $-OCH_2X^2$, $-OCHX^2_2$, —CN, $-SO_{n2}R^{2D}$, $SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl; z2 is an integer from 0 to 4; $R^3$ is independently halogen, $-CX^3_3$, $-CHX^3_2$, $-CH_2X^3$, $-OCX^3_3$, $-OCH_2X^3$, $-OCHX^3_2$, —CN, $-SO_{n3}R^{3D}$, $SO_{v3}NR^{3A}R^{3B}$, $-NR^{3C}NR^{3A}R^{3B}$, $-ONR^{3A}R^{3B}$, $-NHC(O)NR^{3C}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl; z3 is an integer from 0 to 4; $W^1$ is —N═, —CH═, or $-CR^3═$; $R^5$ is $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$, $R^{2B}$, $R^{2C}$, $R^{2D}$, $R^{3A}$, $R^{3B}$, $R^{3C}$, and $R^{3D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, $-NH_2$, —COOH, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $X^2$ and $X^3$ are independently —F, —Cl, —Br, or —I; n2 and n3 are independently an integer from 0 to 4; and m2, m3, v2, and v3 are independently 1 or 2; or a salt thereof.

In embodiments, the compound has the formula:

(I)

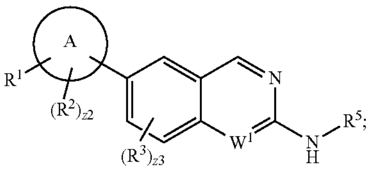

wherein, Ring A is cycloalkyl, heterocycloalkyl, aryl, or heteroaryl; $R^1$ is $—NR^{1A}SO_2R^{1B}$, $—NR^{1A}SOR^{1B}$, $—SOR^{1B}$, $—SO_2R^{1B}$, $—SONR^{1A}R^{1B}$, $—SO_2NR^{1A}R^{1B}$, $—NHC(O)NR^{1A}R^{1B}$, $—NR^{1A}R^{1B}$, $—C(O)R^{1B}$, $—OC(O)R^{1B}$, $—C(O)OR^{1B}$, $—C(O)NR^{1A}R^{1B}$, $—OR^{1B}$, $—NR^{1A}C(O)R^{1B}$, $—NR^{1A}C(O)OR^{1B}$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl; $R^{1A}$ and $R^{1B}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$ substituents bonded to the same nitrogen atom may optionally be joined to form a substituted or unsubstituted heterocycloalkyl; $R^2$ is independently oxo, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl; z2 is an integer from 0 to 4; $R^3$ is independently halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $SO_{v3}NR^{3A}R^{3B}$, $—NR^{3C}NR^{3A}R^{3B}$, $—ONR^{3A}R^{3B}$, $—NHC(O)NR^{3C}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl; z3 is an integer from 0 to 4; $W^1$ is —N=, —CH=, or $—CR^3=$; $R^5$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$, $R^{2B}$, $R^{2C}$, $R^{2D}$, $R^{3A}$, $R^{3B}$, $R^{3C}$, and $R^{3D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $X^2$ and $X^3$ are independently —F, —Cl, —Br, or —I; n2 and n3 are independently an integer from 0 to 4; and m2, m3, v2, and v3 are independently 1 or 2; or a salt thereof.

In embodiments, the compound has the formula:

(Ia)

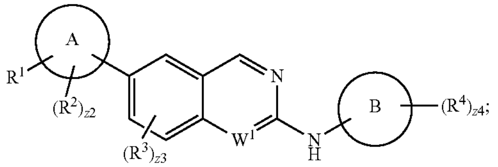

wherein, Ring B is cycloalkyl, heterocycloalkyl, aryl, or heteroaryl; $R^4$ is independently oxo, halogen, $—CX^4_3$, $—CHX^4_2$, $—CH_2X^4$, $—OCX^4_3$, $—OCH_2X^4$, $—OCHX^4_2$, —CN, $—SO_{n4}R^{4D}$, $SO_{v4}NR^{4A}R^{4B}$, $—NR^{4C}NR^{4A}R^{4B}$, $—ONR^{4A}R^{4B}$, $—NHC(O)NR^{4C}NR^{4A}R^{4B}$, $—NHC(O)NR^{4A}R^{4B}$, $N(O)_{m4}$, $—NR^{4A}R^{4B}$, $—C(O)R^{4C}$, $—OC(O)R^{4C}$, $—C(O)—OR^{4C}$, $—OC(O)—OR^{4C}$, $—C(O)NR^{4A}R^{4B}$, $—OC(O)NR^{4A}R^{4B}$, $—OR^{4D}$, $—NR^{4A}SO_2R^{4D}$, $—NR^{4A}C(O)R^{4C}$, $—NR^{4A}C(O)OR^{4C}$, $—NR^{4A}OR^{4C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^4$ substituents may optionally be joined to form a substituted or unsubstituted cycloalkyl, substituted or unsubstituted heterocycloalkyl, substituted or unsubstituted aryl, or substituted or unsubstituted heteroaryl; z4 is independently an integer from 0 to 5; $R^{4A}$, $R^{4B}$, $R^{4C}$, and $R^{4D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $X^4$ is independently —F, —Cl, —Br, or —I; n4 is an integer from 0 to 4; and m4 and v4 are independently 1 or 2; and or a salt thereof.

In embodiments, the compound has the formula:

(II)

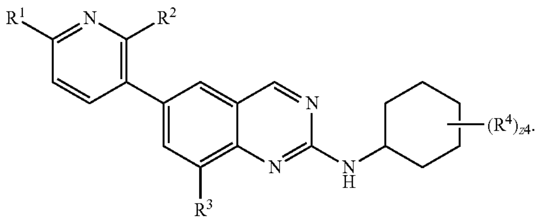

$R^1$, $R^2$, $R^3$, $R^4$, and z4 are as described herein including in embodiments.

In embodiments, the compound has the formula:

(III)

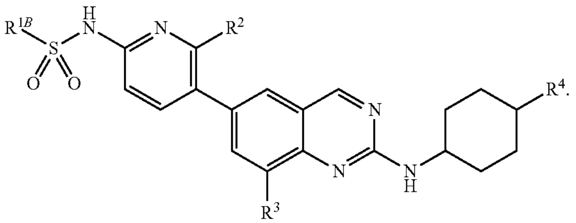

$R^{1B}$, $R^2$, $R^3$, and $R^4$ are as described herein, including in embodiments.

In embodiments, the compound has the formula:

(IIa)

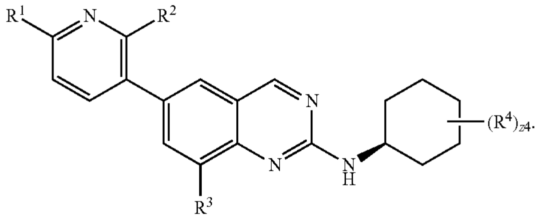

$R^1$, $R^2$, $R^3$, $R^4$, and z4 are as described herein, including in embodiments.

In embodiments, the compound has the formula:

(IIIa)

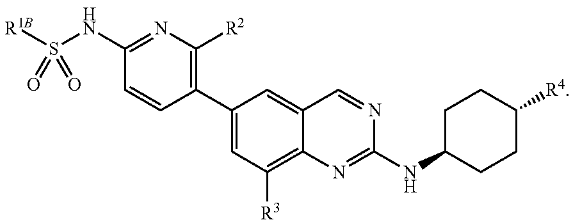

$R^{1B}$, $R^2$, $R^3$, and $R^4$ are as described herein, including in embodiments.

In embodiments, the compound has the formula (IV)

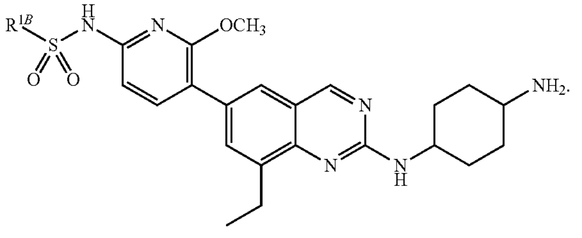

$R^{1B}$ is as described herein, including in embodiments.

In embodiments, the compound has the formula (IVa)

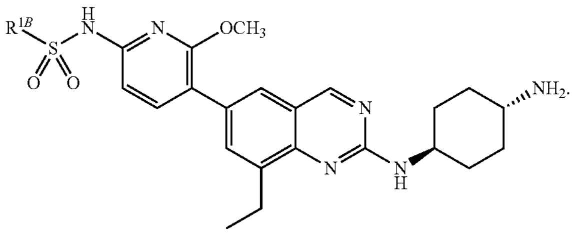

$R^{1B}$ is as described herein, including in embodiments.

In embodiments, $W^1$ is —N=. In embodiments, $W^1$ is —CH=. In embodiments, $W^1$ is —$CR^3$=.

In embodiments, $R^1$ is —$NR^{1A}SO_2R^{1B}$, —$NR^{1A}SOR^{1B}$, —$NHC(O)NR^{1A}R^{1B}$, or —$NR^{1A}C(O)R^{1B}$; $R^{1A}$ is hydrogen or unsubstituted $C_1$-$C_4$ alkyl; and $R^{1B}$ is hydrogen, halo-substituted or unsubstituted $C_1$-$C_2$ alkyl, or halo-substituted or unsubstituted $C_3$-$C_4$ cycloalkyl.

In embodiments, $R^1$ is —$NR^{1A}SO_2R^{1B}$, —$NR^{1A}SOR^{1B}$, or —$NR^{1A}C(O)R^{1B}$; $R^{1A}$ is hydrogen or unsubstituted $C_1$-$C_4$ alkyl; and $R^{1B}$ is hydrogen, halo-substituted or unsubstituted $C_1$-$C_2$ alkyl, or halo-substituted or unsubstituted $C_3$-$C_4$ cycloalkyl.

In embodiments, $R^1$ is —$NR^{1A}SO_2R^{1B}$, —$NR^{1A}SOR^{1B}$, —$NHC(O)NR^{1A}R^{1B}$, or —$NR^{1A}C(O)R^{1B}$. In embodiments, $R^1$ is —$NR^{1A}SO_2R^{1B}$, —$NR^{1A}SOR^{1B}$, or —$NR^{1A}C(O)R^{1B}$. In embodiments, $R^1$ is —$NR^{1A}SO_2R^{1B}$. In embodiments, $R^1$ is —$NR^{1A}SOR^{1B}$. In embodiments, $R^1$ is —$NHC(O)NR^{1A}R^{1B}$. In embodiments, $R^1$ is —$NR^{1A}C(O)R^{1B}$, In embodiments, $R^{1A}$ is hydrogen; and $R^{1B}$ is hydrogen, halo-substituted or unsubstituted $C_1$-$C_2$ alkyl, or halo-substituted or unsubstituted $C_3$-$C_4$ cycloalkyl.

In embodiments, $R^{1A}$ is hydrogen; and R" is halo-substituted or unsubstituted $C_1$-$C_2$ alkyl, or halo-substituted or unsubstituted $C_3$-$C_4$ cycloalkyl.

In embodiments, $R^{1B}$ is halo-substituted $C_1$-$C_2$ alkyl, or unsubstituted $C_3$-$C_4$ cycloalkyl.

In embodiments, $R^{1B}$ is fluoro-substituted $C_1$-$C_2$ alkyl, or unsubstituted $C_3$-$C_4$ cycloalkyl.

In embodiments, $R^{1B}$ is —$CH_2CF_3$.

In embodiments, $R^{1B}$ is unsubstituted cyclopropyl.

In embodiments, $R^1$ is —$NR^{1A}SO_2R^{1B}$, —$NR^{1A}SOR^{1B}$, —$SOR^{1B}$, —$SO_2R^{1B}$, —$SONR^{1A}R^{1B}$, —$SO_2NR^{1A}R^{1B}$, —$NHC(O)NR^{1A}R^{1B}$, —$NR^{1A}R^{1B}$, —$C(O)R^{1B}$, —$OC(O)R^{1B}$, —$C(O)OR^{1B}$, —$C(O)NR^{1A}R^{1B}$, —$OR^{1B}$, —$NR^{1A}C(O)R^{1B}$, —$NR^{1A}C(O)OR^{1B}$, substituted or unsubstituted alkyl (e.g., $C_1$-$C_8$, $C_1$-$C_6$, $C_1$-$C_2$, $C_1$-$C_3$, or $C_1$-$C_4$), substituted or unsubstituted heteroalkyl (e.g., 2 to 8 membered, 2 to 6 membered, 2 to 3 membered, or 2 to 4 membered), substituted or unsubstituted cycloalkyl (e.g., $C_3$-$C_6$, $C_3$-$C_4$, $C_4$-$C_6$, or $C_5$-$C_6$), or substituted or unsubstituted heterocycloalkyl (e.g., 3 to 6 membered, 4 to 6 membered, or 5 to 6 membered, or 3 to 4 membered). In embodiments, $R^1$ is —$NR^{1A}SO_2R^{1B}$, —$NR^{1A}SOR^{1B}$, —$SOR^{1B}$, —$SO_2R^{1B}$, —$SONR^{1A}R^{1B}$, —$SO_2NR^{1A}R^{1B}$, —NHC(O)$NR^{1A}R^{1B}$, —$NR^{1A}R^{1B}$, —C(O)$R^{1B}$, —OC(O)$R^{1B}$, —C(O)$OR^{1B}$, —C(O)$NR^{1A}R^{1B}$, —$OR^{1B}$, —$NR^{1A}$C(O)$R^{1B}$, —$NR^{1A}$C(O)$OR^{1B}$, substituted or unsubstituted $C_1$-$C_4$ alkyl (e.g., $C_1$-$C_2$, $C_1$-$C_3$, or $C_1$-$C_4$), substituted or unsubstituted 2 to 4 membered heteroalkyl (e.g., 2 to 3 membered, or 2 to 4 membered), substituted or unsubstituted $C_3$-$C_6$ cycloalkyl (e.g., $C_3$-$C_4$, $C_4$-$C_6$, or $C_5$-$C_6$), or substituted or unsubstituted 3 to 6 membered heterocycloalkyl (e.g., 4 to 6 membered, or 5 to 6 membered, or 3 to 4 membered).

In embodiments, $R_1$ is —$NHSO_2R^{1B}$, —$NHSOR^{1B}$, —$SOR^{1B}$, —$SO_2R^{1B}$, —$SONR^{1A}R^{1B}$, —$SO_2NR^{1A}R^{1B}$, —NHC(O)$NR^{1A}R^{1B}$, —$NR^{1A}R^{1B}$, —C(O)$R^{1B}$, —OC(O)$R^{1B}$, —C(O)$OR^{1B}$, —C(O)$NR^{1A}R^{1B}$, —$OR^{1B}$, —NHC(O)$R^{1B}$, —NHC(O)$OR^{1B}$, substituted or unsubstituted $C_1$-$C_4$ alkyl (e.g., $C_1$-$C_2$, $C_1$-$C_3$, or $C_1$-$C_4$), substituted or unsubstituted 2 to 4 membered heteroalkyl (e.g., 2 to 3 membered, or 2 to 4 membered), substituted or unsubstituted $C_3$-$C_6$ cycloalkyl (e.g., $C_3$-$C_4$, $C_4$-$C_6$, or $C_5$-$C_6$), or substituted or unsubstituted 3 to 6 membered heterocycloalkyl (e.g., 4 to 6 membered, or 5 to 6 membered, or 3 to 4 membered).

In embodiments, $R_1$ is —$NR^{1A}SO_2R^{1B}$. In embodiments, $R^1$ is —$NR^{1A}SOR^{1B}$. In embodiments, $R^1$ is —$SOR^{1B}$. In embodiments, $R^1$ is —$SO_2R^{1B}$. In embodiments, $R^1$ is —$SONR^{1A}R^{1B}$. In embodiments, $R^1$ is —$SO_2NR^{1A}R^{1B}$. In embodiments, $R^1$ is —NHC(O)$NR^{1A}R^{1B}$. In embodiments, $R^1$ is —$NR^{1A}R^{1B}$. In embodiments, $R^1$ is —C(O)$R^{1B}$. In embodiments, $R^1$ is —OC(O)$R^{1B}$. In embodiments, $R^1$ is —C(O)$OR^{1B}$. In embodiments, $R^1$ is —C(O)$NR^{1A}R^{1B}$. In embodiments, $R^1$ is —$OR^{1B}$. In embodiments, $R^1$ is —NR $1^{A}$C(O)$R^{1B}$. In embodiments, $R^1$ is —$NR^{1A}$C(O)$OR^{1B}$. In embodiments, $R^1$ is substituted or unsubstituted $C_1$-$C_4$ alkyl (e.g., $C_1$-$C_2$, $C_1$-$C_3$, or $C_1$-$C_4$). In embodiments, $R^1$ is substituted or unsubstituted 2 to 4 membered heteroalkyl (e.g., 2 to 3 membered, or 2 to 4 membered). In embodiments, $R^1$ is substituted or unsubstituted $C_3$-$C_6$ cycloalkyl (e.g., $C_3$-$C_4$, $C_4$-$C_6$, or $C_5$-$C_6$). In embodiments, $R^1$ is substituted or unsubstituted 3 to 6 membered heterocycloalkyl (e.g., 4 to 6 membered, or 5 to 6 membered, or 3 to 4 membered). In embodiments, $R^1$ is substituted $C_1$-$C_4$ alkyl (e.g., $C_1$-$C_2$, $C_1$-$C_3$, or $C_1$-$C_4$). In embodiments, $R^1$ is substituted 2 to 4 membered heteroalkyl (e.g., 2 to 3 membered, or 2 to 4 membered). In embodiments, $R^1$ is substituted $C_3$-$C_6$ cycloalkyl (e.g., $C_3$-$C_4$, $C_4$-$C_6$, or $C_5$-$C_6$). In embodiments, $R^1$ is substituted 3 to 6 membered heterocycloalkyl (e.g., 4 to 6 membered, or 5 to 6 membered, or 3 to 4 membered). In embodiments, $R^1$ is unsubstituted $C_1$-$C_4$ alkyl (e.g., $C_1$-$C_2$, $C_1$-$C_3$, or $C_1$-$C_4$). In embodiments, $R^1$ is unsubstituted 2 to 4 membered heteroalkyl (e.g., 2 to 3 membered, or 2 to 4 membered). In embodiments, $R^1$ is unsubstituted $C_3$-$C_6$ cycloalkyl (e.g., $C_3$-$C_4$, $C_4$-$C_6$, or $C_5$-$C_6$). In embodiments, $R^1$ is unsubstituted 3 to 6 membered heterocycloalkyl (e.g., 4 to 6 membered, or 5 to 6 membered, or 3 to 4 membered). In embodiments, $R^1$ is —$NHSO_2R^{1B}$. In embodiments, $R^1$ is —$NHSOR^{1B}$. In embodiments, $R^1$ is —NHC(O)$R^{1B}$.

In embodiments, $R^1$ is $R^{10}$-substituted or unsubstituted alkyl (e.g., $C_1$-$C_6$, $C_1$-$C_8$, $C_1$-$C_2$, $C_1$-$C_3$, or $C_1$-$C_4$). In embodiments, $R^1$ is $R^{10}$-substituted or unsubstituted heteroalkyl (e.g., 2 to 8 membered, 2 to 6 membered, 2 to 3 membered, or 2 to 4 membered). In embodiments, $R^1$ is $R^{10}$-substituted or unsubstituted cycloalkyl (e.g., $C_3$-$C_6$, $C_3$-$C_4$, $C_4$-$C_6$, or $C_5$-$C_6$). In embodiments, $R^1$ is $R^{10}$-substituted or unsubstituted heterocycloalkyl (e.g., 3 to 6 membered, 4 to 6 membered, or 5 to 6 membered, or 3 to 4 membered). In embodiments, $R^1$ is $R^{10}$-substituted or unsubstituted $C_1$-$C_4$ alkyl (e.g., $C_1$-$C_2$, $C_1$-$C_3$, or $C_1$-$C_4$). In embodiments, $R^1$ is $R^{10}$-substituted or unsubstituted 2 to 4 membered heteroalkyl (e.g., 2 to 3 membered, or 2 to 4 membered). In embodiments, $R^1$ is $R^{10}$-substituted or unsubstituted $C_3$-$C_6$ cycloalkyl (e.g., $C_3$-$C_4$, $C_4$-$C_6$, or $C_5$-$C_6$). In embodiments, $R^1$ is $R^{10}$-substituted or unsubstituted 3 to 6 membered heterocycloalkyl (e.g., 4 to 6 membered, or 5 to 6 membered, or 3 to 4 membered).

In embodiments, $R^1$ is $R^{10}$-substituted $C_1$-$C_4$ alkyl (e.g., $C_1$-$C_2$, $C_1$-$C_3$, or $C_1$-$C_4$). In embodiments, $R^1$ is $R^{10}$-substituted 2 to 4 membered heteroalkyl (e.g., 2 to 3 membered, or 2 to 4 membered). In embodiments, $R^1$ is $R^{10}$-substituted $C_3$-$C_6$ cycloalkyl (e.g., $C_3$-$C_4$, $C_4$-$C_6$, or $C_5$-$C_6$). In embodiments, $R^1$ is $R^{10}$-substituted 3 to 6 membered heterocycloalkyl (e.g., 4 to 6 membered, or 5 to 6 membered, or 3 to 4 membered).

In embodiments, $R^{1A}$ and $R^{1B}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_2$, $C_1$-$C_3$, or $C_1$-$C_4$), substituted or unsubstituted heteroalkyl (e.g., 2 to 8 membered, 2 to 6 membered, 2 to 3 membered, or 2 to 4 membered), substituted or unsubstituted cycloalkyl (e.g., $C_3$-$C_6$, $C_3$-$C_4$, $C_4$-$C_6$, or $C_5$-$C_6$), or substituted or unsubstituted heterocycloalkyl (e.g., 3 to 6 membered, 4 to 6 membered, or 5 to 6 membered, or 3 to 4 membered); $R^{1A}$ and $R^{1B}$ substituents bonded to the same nitrogen atom may optionally be joined to form a substituted or unsubstituted heterocycloalkyl (e.g., 3 to 6 membered, 4 to 6 membered, or 5 to 6 membered, or 3 to 4 membered).

In embodiments, $R^{1A}$ and $R^{1B}$ are independently hydrogen, substituted or unsubstituted alkyl (e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), or substituted or unsubstituted heterocycloalkyl (e.g., 3 to 8 membered, 3 to 6 membered, or 5 to 6 membered).

In embodiments, $R^{1A}$ is hydrogen. In embodiments, $R^{1A}$ is —$CCl_3$. In embodiments, $R^{1A}$ is —$CBr_3$. In embodiments, $R^{1A}$ is —$CF_3$. In embodiments, $R^{1A}$ is —$CI_3$. In embodiments, $R^{1A}$ is —$CHCl_2$. In embodiments, $R^{1A}$ is —$CHBr_2$. In embodiments, $R^{1A}$ is —$CHF_2$. In embodiments, $R^{1A}$ is —$CHI_2$. In embodiments, $R^{1A}$ is —$CH_2Cl$. In embodiments, $R^{1A}$ is —$CH_2Br$. In embodiments, $R^{1A}$ is —$CH_2F$. In embodiments, $R^{1A}$ is —$CH_2I$. In embodiments, $R^{1A}$ is —CN. In embodiments, $R^{1A}$ is —OH. In embodiments, $R^{1A}$ is —$NH_2$. In embodiments, $R^{1A}$ is —COOH. In embodiments, $R^{1A}$ is —$CONH_2$. In embodiments, $R^{1A}$ is —$OCCl_3$. In embodiments, $R^{1A}$ is —$OCF_3$. In embodiments, $R^{1A}$ is —$OCBr_3$. In embodiments, $R^{1A}$ is —$OCI_3$. In embodiments, $R^{1A}$ is —$OCHCl_2$. In embodiments, $R^{1A}$ is —$OCHBr_2$. In embodiments, $R^{1A}$ is —$OCHI_2$. In embodiments, $R^{1A}$ is —$OCHF_2$. In embodiments, $R^{1A}$ is —$OCH_2Cl$. In embodiments, $R^{1A}$ is —$OCH_2Br$. In embodiments, $R^{1A}$ is —$OCH_2I$. In embodiments, $R^{1A}$ is —$OCH_2F$. In embodiments, $R^{1A}$ is halogen. In embodiments, $R^{1A}$ is —$NO_2$. In embodiments, $R^{1A}$ is —$OCH_3$. In embodiments, $R^{1A}$ is —$OCH_2CH_3$. In embodiments, $R^{1A}$ is —$OCH(CH_3)_2$. In embodiments, $R^{1A}$ is —$OC(CH_3)_3$. In embodiments, $R^{1A}$ is —$CH_3$. In embodiments, $R^{1A}$ is —$CH_2CH_3$. In embodiments, $R^{1A}$ is —$CH(CH_3)_2$. In embodiments, $R^{1A}$ is —$C(CH_3)_3$. In embodiments, $R^{1A}$ is unsubstituted cyclopropyl. In embodiments, $R^{1A}$ is unsubstituted cyclobutyl. In embodiments, $R^{1A}$ is unsubstituted cyclopentyl. In embodiments, $R^{1A}$ is unsubstituted cyclohexyl. In embodiments, $R^{1A}$ is substituted or unsubstituted alkyl (e.g., $C_1$-$C_8$, $C_1$-$C_6$, or $C_1$-$C_4$). In embodiments, $R^{1A}$ is substituted or unsubstituted heteroalkyl (e.g., 2 to 8 membered, 2 to 6 membered, or 2 to 4 membered). In embodiments, $R^{1A}$ is substituted or unsubstituted cycloalkyl (e.g., $C_3$-$C_8$, $C_3$-$C_6$, or $C_5$-$C_6$). In embodiments, $R^{1A}$ is substituted or unsubstituted heterocycloalkyl (e.g., 3 to 8 membered, 3 to 6 membered, or 5 to 6 membered).

In embodiments, $R^{1A}$ is hydrogen, unsubstituted $C_1$-$C_4$ alkyl, or unsubstituted cyclopropyl.

In embodiments, $R^{1B}$ is hydrogen. In embodiments, $R^{1B}$ is —$CCl_3$. In embodiments, $R^{1B}$, is —$CBr_3$. In embodiments, $R^{1B}$ is —$CF_3$. In embodiments, $R^{1B}$ is —$CI_3$. In embodiments, $R^{1B}$ is —$CHCl_2$. In embodiments, $R^{1B}$ is —$CHBr_2$. In embodiments, $R^{1B}$ is —$CHF_2$. In embodiments, $R^{1B}$, is —$CHI_2$. In embodiments, $R^{1B}$ is —$CH_2Cl$. In embodiments, $R^{1B}$ is —$CH_2Br$. In embodiments, $R^{1B}$ is —$CH_2F$. In embodiments, $R^{1B}$ is —$CH_2I$. In embodiments, $R^{1B}$ is —CN. In embodiments, $R^{1B}$ is —OH. In embodiments, $R^{1B}$ is —$NH_2$. In embodiments, $R^{1B}$ is —COOH. In embodiments, $R^{1B}$ is —$CONH_2$. In embodiments, $R^{1B}$ is —$OCCl_3$. In embodiments, $R^{1B}$ is —$OCF_3$. In embodiments, $R^{1B}$ is —$OCBr_3$. In embodiments, $R^{1B}$ is —$OCI_3$. In embodiments, $R^{1B}$ is —$OCHCl_2$. In embodiments, $R^{1B}$ is —$OCHBr_2$. In embodiments, $R^{1B}$ is —$OCHI_2$. In embodiments, $R^{1B}$, is —$OCHF_2$. In embodiments, $R^{1B}$ is —$OCH_2Cl$. In embodiments, $R^{1B}$ is —$OCH_2Br$. In embodiments, $R^{1B}$ is —$OCH_2I$. In embodiments, $R^{1B}$ is —$OCH_2F$. In embodiments, $R^{1B}$ is halogen. In embodiments, $R^{1B}$ is —$NO_2$. In embodiments, $R^{1B}$ is —$OCH_3$. In embodiments, $R^{1B}$, is —$OCH_2CH_3$. In embodiments, $R^{1B}$ is —$OCH(CH_3)_2$. In embodiments, $R^{1B}$ is —$OC(CH_3)_3$. In embodiments, $R_{1B}$ is —$CH_3$. In embodiments, $R^{1B}$ is —$CH_2CH_3$. In embodiments, $R^{1B}$ is —$CH(CH_3)_2$. In embodiments, $R^{1B}$ is —$C(CH_3)_3$. In embodiments, $R^{1B}$ is unsubstituted cyclopropyl. In embodiments, $R^{1B}$ is unsubstituted cyclobutyl. In embodiments, $R^{1B}$ is unsubstituted cyclopentyl. In embodiments, $R^{1B}$ is unsubstituted cyclohexyl. In embodiments, $R^{1B}$ is substituted or unsubstituted alkyl (e.g., $C_1$-$C_8$, $C_1$-$C_6$, or $C_1$-$C_4$). In embodiments, $R^{1B}$ is substituted or unsubstituted heteroalkyl (e.g., 2 to 8 membered, 2 to 6 membered, or 2 to 4 membered). In embodiments, $R^{1B}$ is substituted or unsubstituted cycloalkyl (e.g., $C_3$-$C_8$, $C_3$-$C_6$, or $C_5$-$C_6$). In embodiments, $R^{1B}$ is substituted or unsubstituted heterocycloalkyl (e.g., 3 to 8 membered, 3 to 6 membered, or 5 to 6 membered). In embodiments, $R^{1B}$ is substituted or unsubstituted phenyl. In embodiments, $R^{1B}$ is halo-substituted or unsubstituted phenyl. In embodiments, $R^{1B}$ is halo-substituted phenyl. In embodiments, $R^{1B}$ is F-substituted phenyl. In embodiments, $R^{1B}$ is Cl-substituted phenyl. In embodiments, $R^{1B}$ is Br-substituted phenyl. In embodiments, $R^{1B}$ is I-substituted phenyl.

In embodiments, $R^{1B}$ is —$CH_2CCl_3$. In embodiments, $R^{1B}$ is —$CH_2CBr_3$. In embodiments, $R^{1B}$ is —$CH_2CF_3$. In embodiments, $R^{1B}$ is —$CH_2CI_3$. In embodiments, $R^{1B}$ is —$CH_2CHCl_2$. In embodiments, $R^{1B}$ is —$CH_2CHBr_2$. In embodiments, $R^{1B}$ is —$CH_2CHF_2$. In embodiments, $R^{1B}$ is —$CH_2CHI_2$. In embodiments, $R^{1B}$ is —$CH_2CH_2Cl$. In embodiments, $R^{1B}$, is —$CH_2CH_2Br$. In embodiments, $R^{1B}$ is —$CH_2CH_2F$. In embodiments, $R^{1B}$ is —$CH_2CH_2I$. In embodiments, $R^{1B}$ is —$CH_2CH_2CF_3$.

In embodiments, $R^{1B}$ is hydrogen, unsubstituted $C_1$-$C_4$ alkyl, or unsubstituted cyclopropyl.

$R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted alkyl (e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered); two $R^2$ substituents may optionally be joined to form a substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered).

In embodiments, $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted alkyl (e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered).

In embodiments, $R^{10}$ is independently halogen. In embodiments, $R^{10}$ is independently —F. In embodiments, $R^{10}$ is independently —Cl. In embodiments, $R^{10}$ is independently —Br. In embodiments, $R^{10}$ is independently —I. In embodiments, $R^{10}$ is independently —$CH_2OCH_3$. In embodiments, $R^{10}$ is independently —$SO_2CH_3$. In embodiments, $R^{10}$ is independently —$SCH_3$. In embodiments, $R^{10}$ is independently —$OCH_3$. In embodiments, $R^{10}$ is independently unsubstituted $C_1$-$C_4$ alkyl. In embodiments, $R^{10}$ is independently unsubstituted cyclopropyl. In embodiments, $R^{10}$ is independently unsubstituted phenyl. In embodiments, $R^{10}$ is independently hydrogen. In embodiments, $R^{10}$ is independently —$CCl_3$. In embodiments, $R^{10}$ is independently —$CBr_3$. In embodiments, $R^{10}$ is independently —$CF_3$. In embodiments, $R^{10}$ is independently —$CI_3$. In embodiments, $R^{10}$ is independently —$CHCl_2$. In embodiments, $R^{10}$ is independently —$CHBr_2$. In embodiments, $R^{10}$ is independently —$CHF_2$. In embodiments, $R^{10}$ is independently —$CHI_2$. In embodiments, $R^{10}$ is independently —$CH_2Cl$. In embodiments, $R^{10}$ is independently —$CH_2Br$. In embodiments, $R^{10}$ is independently —$CH_2F$. In embodiments, $R^{10}$ is independently —$CH_2I$. In embodiments, $R^{10}$ is independently —CN. In embodiments, $R^{10}$ is independently —OH. In embodiments, $R^{10}$ is independently —$NH_2$. In embodiments, $R^{10}$ is independently —COOH. In embodiments, $R^{10}$ is independently —$CONH_2$. In embodiments, $R^{10}$ is independently —$OCCl_3$. In embodiments, $R^{10}$ is independently —$OCF_3$. In embodiments, $R^{10}$ is independently —$OCBr_3$. In embodiments, $R^{10}$ is independently —$OCI_3$. In embodiments, $R^{10}$ is independently —$OCHCl_2$. In embodiments, $R^{10}$ is independently —$OCHBr_2$. In embodiments, $R^{10}$ is independently —$OCHI_2$. In embodiments, $R^{10}$ is independently —$OCHF_2$. In embodiments, $R^{10}$ is independently —$OCH_2Cl$. In embodiments, $R^{10}$ is independently —$OCH_2Br$. In embodiments, $R^{10}$ is independently —$OCH_2I$. In embodiments, $R^{10}$ is independently —$OCH_2F$. In embodiments, $R^{10}$ is independently halogen. In embodiments, $R^{10}$ is independently —$NO_2$. In embodiments, $R^{10}$ is independently —$OCH_3$. In embodiments, $R^{10}$ is independently —$OCH_2CH_3$. In embodiments, $R^{10}$ is independently —$OCH(CH_3)_2$. In embodiments, $R^{10}$ is independently —$OC(CH_3)_3$. In embodiments, $R^{10}$ is independently —$CH_3$. In embodiments, $R^{10}$ is independently —$CH_2CH_3$. In embodiments, $R^{10}$ is independently —$CH(CH_3)_2$. In embodiments, $R^{10}$ is independently —$C(CH_3)_3$. In embodiments, $R^{10}$ is independently unsubstituted cyclopropyl. In embodiments, $R^{10}$ is independently unsubstituted cyclobutyl. In embodiments, $R^{10}$ is independently unsubstituted cyclopentyl. In embodiments, $R^{10}$ is independently unsubstituted cyclohexyl. In embodiments, $R^{10}$ is independently substituted or unsubstituted alkyl (e.g., $C_1$-$C_8$, $C_1$-$C_6$, or $C_1$-$C_4$). In embodiments, $R^{10}$ is independently substituted or unsubstituted heteroalkyl (e.g., 2 to 8 membered, 2 to 6 membered, or 2 to 4 membered). In embodiments, $R^{10}$ is independently substituted or unsubstituted cycloalkyl (e.g., $C_3$-$C_8$, $C_3$-$C_6$, or $C_5$-$C_6$). In embodiments, $R^{10}$ is independently substituted or unsubstituted heterocycloalkyl (e.g., 3 to 8 membered, 3 to 6 membered, or 5 to 6 membered). In embodiments, $R^{10}$ is independently substituted or unsubstituted aryl (e.g., $C_6$-$C_{10}$, $C_{10}$, or phenyl). In embodiments, $R^{10}$ is independently substituted or unsubstituted heteroaryl (e.g., 5 to 10 membered, 5 to 9 membered, or 5 to 6 membered). In embodiments, $R^{10}$ is independently unsubstituted alkyl (e.g., $C_1$-$C_8$, $C_1$-$C_6$, or $C_1$-$C_4$). In embodiments, $R^{10}$ is independently unsubstituted heteroalkyl (e.g., 2 to 8 membered, 2 to 6 membered, or 2 to 4 membered). In embodiments, $R^{10}$ is independently unsubstituted cycloalkyl (e.g., $C_3$-$C_8$, $C_3$-$C_6$, or $C_5$-$C_6$). In embodiments, $R^{10}$ is independently unsubstituted heterocycloalkyl (e.g., 3 to 8 membered, 3 to 6 membered, or 5 to 6 membered). In embodiments, $R^{10}$ is independently unsubstituted aryl (e.g., $C_6$-$C_{10}$, $C_{10}$, or phenyl). In embodiments, $R^{10}$ is independently unsubstituted heteroaryl (e.g., 5 to 10 membered, 5 to 9 membered, or 5 to 6 membered).

In embodiments, $R^2$ is independently —$OCX^2_3$, —$OCH_2X^2$, —$OCHX^2_2$, —$OR^{2D}$, or unsubstituted alkyl; and $R^{2D}$ is independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, or unsubstituted $C_1$-$C_4$ alkyl.

In embodiments, $R^2$ is independently —$OCX^2_3$, —$OCH_2X^2$, —$OCHX^2_2$, or —$OCH_3$.

In embodiments, $R^2$ is independently —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered).

In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently —$CH_2OCH_3$. In embodiments, $R^2$ is independently —$SCH_3$. In embodiments, $R^2$ is independently —$OCH_3$. In embodiments, $R^2$ is independently —$CH_2CH_2OCH_3$. In embodiments, $R^2$ is independently —$SCH_2CH_3$. In embodiments, $R^2$ is independently —$OCH_2CH_3$. In embodiments, $R^2$ is independently —$CH_2OCH_2CH_3$. In embodiments, $R^2$ is independently unsubstituted $C_1$-$C_4$ alkyl. In embodiments, $R^2$ is independently unsubstituted cyclopropyl. In embodiments, $R^2$ is independently hydrogen. In embodiments, $R^2$ is independently —$CCl_3$. In embodiments, $R^2$ is independently —$CBr_3$. In embodiments, $R^2$ is independently —$CF_3$. In embodiments, $R^2$ is independently —$CI_3$. In embodiments, $R^2$ is independently —$CHCl_2$. In embodiments, $R^2$ is independently —$CHBr_2$. In embodiments, $R^2$ is independently —$CHF_2$. In embodiments, $R^2$ is independently —$CHI_2$. In embodiments, $R^2$ is independently —$CH_2Cl$. In embodiments, $R^2$ is independently —$CH_2Br$. In embodiments, $R^2$ is independently —$CH_2F$. In embodiments, $R^2$ is independently —$CH_2I$. In embodiments, $R^2$ is independently —CN. In embodiments, $R^2$ is independently —OH. In embodiments, $R^2$ is independently —$NH_2$. In embodiments, $R^2$ is independently —COOH. In embodiments, $R^2$ is independently —$CONH_2$. In embodiments, $R^2$ is independently —$OCCl_3$. In embodiments, $R^2$ is independently —$OCF_3$. In embodiments, $R^2$ is independently —$OCBr_3$. In embodiments, $R^2$ is independently —$OCI_3$. In embodiments, $R^2$ is independently —$OCHCl_2$. In embodiments, $R^2$ is independently —$OCHBr_2$. In embodiments, $R^2$ is independently —$OCHI_2$. In embodiments, $R^2$ is independently —$OCHF_2$. In embodiments, $R^2$ is independently —$OCH_2Cl$. In embodiments, $R^2$ is independently —$OCH_2Br$. In embodiments, $R^2$ is independently —$OCH_2I$. In embodiments, $R^2$ is independently —$OCH_2F$. In embodiments, $R^2$ is independently —$OCH_3$. In embodiments, $R^2$ is independently —$OCH_2CH_3$. In embodiments, $R^2$ is independently —$OCH(CH_3)_2$. In embodiments, $R^2$ is independently —$OC(CH_3)_3$. In embodiments, $R^2$ is independently —$CH_3$. In embodiments, $R^2$ is independently —$CH_2CH_3$. In embodiments, $R^2$ is independently —$CH(CH_3)_2$. In embodiments, $R^2$ is independently —$C(CH_3)_3$. In embodiments, $R^2$ is independently unsubstituted cyclopropyl. In embodiments, $R^2$ is independently unsubstituted cyclobutyl. In embodiments, $R^2$ is independently unsubstituted cyclopentyl. In embodiments, $R^2$ is independently unsubstituted cyclohexyl. In embodiments, $R^2$ is independently substituted or unsubstituted alkyl (e.g., $C_1$-$C_8$, $C_1$-$C_6$, or $C_1$-$C_4$). In embodiments, $R^2$ is independently substituted or unsubstituted heteroalkyl (e.g., 2 to 8 membered, 2 to 6 membered, or 2 to 4 membered). In embodiments, $R^2$ is independently substituted or unsubstituted cycloalkyl (e.g., $C_3$-$C_8$, $C_3$-$C_6$, or $C_5$-$C_6$). In embodiments, $R^2$ is independently substituted or unsubstituted heterocycloalkyl (e.g., 3 to 8 membered, 3 to 6 membered, or 5 to 6 membered). In embodiments, $R^2$ is independently substituted or unsubstituted aryl (e.g., $C_6$-$C_{10}$, $C_{10}$, or phenyl). In embodiments, $R^2$ is independently substituted or unsubstituted heteroaryl (e.g., 5 to 10 membered, 5 to 9 membered, or 5 to 6 membered). In embodiments, $R^2$ is independently unsubstituted alkyl (e.g., $C_1$-$C_8$, $C_1$-$C_6$, or $C_1$-$C_4$). In embodiments, $R^2$ is independently unsubstituted heteroalkyl (e.g., 2 to 8 membered, 2 to 6 membered, or 2 to 4 membered). In embodiments, $R^2$ is independently unsubstituted cycloalkyl (e.g., $C_3$-$C_8$, $C_3$-$C_6$, or $C_5$-$C_6$). In embodiments, $R^2$ is independently unsubstituted heterocycloalkyl (e.g., 3 to 8 membered, 3 to 6 membered, or 5 to 6 membered). In embodiments, $R^2$ is independently unsubstituted aryl (e.g., $C_6$-$C_{10}$, $C_{10}$, or phenyl). In embodiments, $R^2$ is independently unsubstituted heteroaryl (e.g., 5 to 10 membered, 5 to 9 membered, or 5 to 6 membered).

In embodiments, z2 is 0. In embodiments, z2 is 1. In embodiments, z2 is 2. In embodiments, z2 is 3. In embodiments, z2 is 4. In embodiments, $X^2$ is independently —F. In embodiments, $X^2$ is independently —Cl. In embodiments, $X^2$ is independently —Br. In embodiments, $X^2$ is independently —I. In embodiments, n2 is 0. In embodiments, n2 is 1. In embodiments, n2 is 2. In embodiments, n2 is 3. In embodiments, n2 is 4. In embodiments, m2 is 1. In embodiments, m2 is 2. In embodiments, v2 is 1. In embodiments, v2 is 2.

In embodiments, $R^{2A}$, $R^{2B}$, $R^{2C}$, and $R^{2D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl(e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered); $R^{2A}$ and $R^{2B}$, substituents bonded to the same nitrogen atom may optionally be joined to form a substituted or unsubstituted heterocycloalkyl (e.g., 3 to 8 membered, 3 to 6 membered, or 5 to 6 membered) or substituted or unsubstituted heteroaryl (e.g., 5 to 10 membered, 5 to 9 membered, or 5 to 6 membered).

In embodiments, $R^{2A}$ is independently hydrogen. In embodiments, $R^{2A}$ is independently $—CH_3$. In embodiments, $R^{2A}$ is independently $—CH_2CH_3$. In embodiments, $R^{2A}$ is independently $—CH(CH_3)_2$. In embodiments, $R^{2A}$ is independently $—C(CH_3)_3$. In embodiments, $R^{2A}$ is independently unsubstituted cyclopropyl. In embodiments, $R^{2A}$ is independently unsubstituted cyclobutyl. In embodiments, $R^{2A}$ is independently unsubstituted cyclopentyl. In embodiments, $R^{2A}$ is independently unsubstituted cyclohexyl. In embodiments, $R^{2A}$ is independently substituted or unsubstituted alkyl (e.g., $C_1$-$C_8$, $C_1$-$C_6$, or $C_1$-$C_4$). In embodiments, $R^{2A}$ is independently substituted or unsubstituted heteroalkyl (e.g., 2 to 8 membered, 2 to 6 membered, or 2 to 4 membered). In embodiments, $R^{2A}$ is independently substituted or unsubstituted cycloalkyl (e.g., $C_3$-$C_8$, $C_3$-$C_6$, or $C_5$-$C_6$). In embodiments, $R^{2A}$ is independently substituted or unsubstituted heterocycloalkyl (e.g., 3 to 8 membered, 3 to 6 membered, or 5 to 6 membered). In embodiments, $R^{2A}$ is independently substituted or unsubstituted aryl (e.g., $C_6$-$C_{10}$, $C_{10}$, or phenyl). In embodiments, $R^{2A}$ is independently substituted or unsubstituted heteroaryl (e.g., 5 to 10 membered, 5 to 9 membered, or 5 to 6 membered). In embodiments, $R^{2A}$ is independently unsubstituted alkyl (e.g., $C_1$-$C_8$, $C_1$-$C_6$, or $C_1$-$C_4$). In embodiments, $R^{2A}$ is independently unsubstituted heteroalkyl (e.g., 2 to 8 membered, 2 to 6 membered, or 2 to 4 membered). In embodiments, $R^{2A}$ is independently unsubstituted cycloalkyl (e.g., $C_3$-$C_8$, $C_3$-$C_6$, or $C_5$-$C_6$). In embodiments, $R^{2A}$ is independently unsubstituted heterocycloalkyl (e.g., 3 to 8 membered, 3 to 6 membered, or 5 to 6 membered). In embodiments, $R^{2A}$ is independently unsubstituted aryl (e.g., $C_6$-$C_{10}$, $C_{10}$, or phenyl). In embodiments, $R^{2A}$ is independently unsubstituted heteroaryl (e.g., 5 to 10 membered, 5 to 9 membered, or 5 to 6 membered).

In embodiments, $R^{2B}$, is independently hydrogen. In embodiments, $R^{2B}$, is independently $—CH_3$. In embodiments, $R^{2B}$, is independently $—CH_2CH_3$. In embodiments, $R^{2B}$, is independently $—CH(CH_3)_2$. In embodiments, $R^{2B}$, is independently $—C(CH_3)_3$. In embodiments, $R^{2B}$, is independently unsubstituted cyclopropyl. In embodiments, $R^{2B}$, is independently unsubstituted cyclobutyl. In embodiments, $R^{2B}$, is independently unsubstituted cyclopentyl. In embodiments, $R^{2B}$, is independently unsubstituted cyclohexyl. In embodiments, $R^{2B}$, is independently substituted or unsubstituted alkyl (e.g., $C_1$-$C_8$, $C_1$-$C_6$, or $C_1$-$C_4$). In embodiments, $R^{2B}$, is independently substituted or unsubstituted heteroalkyl (e.g., 2 to 8 membered, 2 to 6 membered, or 2 to 4 membered). In embodiments, $R^{2B}$, is independently substituted or unsubstituted cycloalkyl (e.g., $C_3$-$C_8$, $C_3$-$C_6$, or $C_5$-$C_6$). In embodiments, $R^{2B}$, is independently substituted or unsubstituted heterocycloalkyl (e.g., 3 to 8 membered, 3 to 6 membered, or 5 to 6 membered). In embodiments, $R^{2B}$, is independently substituted or unsubstituted aryl (e.g., $C_6$-$C_{10}$, $C_{10}$, or phenyl). In embodiments, $R^{2B}$, is independently substituted or unsubstituted heteroaryl (e.g., 5 to 10 membered, 5 to 9 membered, or 5 to 6 membered). In embodiments, $R^{2B}$, is independently unsubstituted alkyl (e.g., $C_1$-$C_8$, $C_1$-$C_6$, or $C_1$-$C_4$). In embodiments, $R^{2B}$, is independently unsubstituted heteroalkyl (e.g., 2 to 8 membered, 2 to 6 membered, or 2 to 4 membered). In embodiments, $R^{2B}$, is independently unsubstituted cycloalkyl (e.g., $C_3$-$C_8$, $C_3$-$C_6$, or $C_5$-$C_6$). In embodiments, $R^{2B}$, is independently unsubstituted heterocycloalkyl (e.g., 3 to 8 membered, 3 to 6 membered, or 5 to 6 membered). In embodiments, $R^{2B}$, is independently unsubstituted aryl (e.g., $C_6$-$C_{10}$, $C_{10}$, or phenyl). In embodiments, $R^{2B}$, is independently unsubstituted heteroaryl (e.g., 5 to 10 membered, 5 to 9 membered, or 5 to 6 membered).

In embodiments, R" is independently hydrogen. In embodiments, $R^{2C}$ is independently $—CH_3$. In embodiments, $R^{2C}$ is independently $—CH_2CH_3$. In embodiments, $R^{2C}$ is independently $—CH(CH_3)_2$. In embodiments, $R^{2C}$ is independently $—C(CH_3)_3$. In embodiments, $R^{2C}$ is independently unsubstituted cyclopropyl. In embodiments, $R^{2C}$ is independently unsubstituted cyclobutyl. In embodiments, $R^{2C}$ is independently unsubstituted cyclopentyl. In embodiments, $R^{2C}$ is independently unsubstituted cyclohexyl. In embodiments, $R^{2C}$ is independently substituted or unsubstituted alkyl (e.g., $C_1$-$C_8$, $C_1$-$C_6$, or $C_1$-$C_4$). In embodiments, $R^{2C}$ is independently substituted or unsubstituted heteroalkyl (e.g., 2 to 8 membered, 2 to 6 membered, or 2 to 4 membered). In embodiments, $R^{2C}$ is independently substituted or unsubstituted cycloalkyl (e.g., $C_3$-$C_8$, $C_3$-$C_6$, or $C_5$-$C_6$). In embodiments, $R^{2C}$ is independently substituted or unsubstituted heterocycloalkyl (e.g., 3 to 8 membered, 3 to 6 membered, or 5 to 6 membered). In embodiments, $R^{2C}$ is independently substituted or unsubstituted aryl (e.g., $C_6$-$C_{10}$, $C_{10}$, or phenyl). In embodiments, $R^{2C}$ is independently substituted or unsubstituted heteroaryl (e.g., 5 to 10 membered, 5 to 9 membered, or 5 to 6 membered). In embodiments, $R^{2C}$ is independently unsubstituted alkyl (e.g., $C_1$-$C_8$, $C_1$-$C_6$, or $C_1$-$C_4$). In embodiments, $R^{2C}$ is independently unsubstituted heteroalkyl (e.g., 2 to 8 membered, 2 to 6 membered, or 2 to 4 membered). In embodiments, $R^{2C}$ is independently unsubstituted cycloalkyl (e.g., $C_3$-$C_8$, $C_3$-$C_6$, or $C_5$-$C_6$). In embodiments, $R^{2C}$ is independently unsubstituted heterocycloalkyl (e.g., 3 to 8 membered, 3 to 6 membered, or 5 to 6 membered). In embodiments, $R^{2C}$ is independently unsubstituted aryl (e.g., $C_6$-$C_{10}$, $C_{10}$, or phenyl). In embodiments, $R^{2C}$ is independently unsubstituted heteroaryl (e.g., 5 to 10 membered, 5 to 9 membered, or 5 to 6 membered).

In embodiments, $R^{2D}$ is independently hydrogen. In embodiments, $R^{2D}$ is independently —$CH_3$. In embodiments, $R^{2D}$ is independently —$CH_2CH_3$. In embodiments, $R^{2D}$ is independently —$CH(CH_3)_2$. In embodiments, $R^{2D}$ is independently —$C(CH_3)_3$. In embodiments, $R^{2D}$ is independently unsubstituted cyclopropyl. In embodiments, $R^{2'}$ is independently unsubstituted cyclobutyl. In embodiments, $R^{2D}$ is independently unsubstituted cyclopentyl. In embodiments, $R^{2D}$ is independently unsubstituted cyclohexyl. In embodiments, $R^{2D}$ is independently substituted or unsubstituted alkyl (e.g., $C_1$-$C_8$, $C_1$-$C_6$, or $C_1$-$C_4$). In embodiments, $R^{2D}$ is independently substituted or unsubstituted heteroalkyl (e.g., 2 to 8 membered, 2 to 6 membered, or 2 to 4 membered). In embodiments, $R^{2D}$ is independently substituted or unsubstituted cycloalkyl (e.g., $C_3$-$C_8$, $C_3$-$C_6$, or $C_5$-$C_6$). In embodiments, $R^{2.1}$ is independently substituted or unsubstituted heterocycloalkyl (e.g., 3 to 8 membered, 3 to 6 membered, or 5 to 6 membered). In embodiments, $R^{2D}$ is independently substituted or unsubstituted aryl (e.g., $C_6$-$C_{10}$, $C_{10}$, or phenyl). In embodiments, $R^{2D}$ is independently substituted or unsubstituted heteroaryl (e.g., 5 to 10 membered, 5 to 9 membered, or 5 to 6 membered). In embodiments, $R^{2D}$ is independently unsubstituted alkyl (e.g., $C_1$-$C_8$, $C_1$-$C_6$, or $C_1$-$C_4$). In embodiments, $R^{2D}$ is independently unsubstituted heteroalkyl (e.g., 2 to 8 membered, 2 to 6 membered, or 2 to 4 membered). In embodiments, $R^{2D}$ is independently unsubstituted cycloalkyl (e.g., $C_3$-$C_8$, $C_3$-$C_6$, or $C_5$-$C_6$). In embodiments, $R^{2D}$ is independently unsubstituted heterocycloalkyl (e.g., 3 to 8 membered, 3 to 6 membered, or 5 to 6 membered). In embodiments, $R^{2'}$ is independently unsubstituted aryl (e.g., $C_6$-$C_{10}$, $C_{10}$, or phenyl). In embodiments, $R^2$ is independently unsubstituted heteroaryl (e.g., 5 to 10 membered, 5 to 9 membered, or 5 to 6 membered).

In embodiments, $R^3$ is independently —$CX^3_3$, —$CHX^3_2$, —$CH_2X^3$, or unsubstituted $C_1$-$C_4$ alkyl.

In embodiments, $R^3$ is independently unsubstituted $C_1$-$C_3$ alkyl.

In embodiments, $R^3$ is independently halogen, oxo, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted alkyl (e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered); two adjacent $R^3$ substituents may optionally be joined to form a substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered).

In embodiments, z3 is an integer from 0 to 4. In embodiments, $X^3$ is independently —F. In embodiments, $X^3$ is independently —Cl. In embodiments, $X^3$ is independently —Br. In embodiments, $X^3$ is independently —I. In embodiments, n3 is 0. In embodiments, n3 is 1. In embodiments, n3 is 2. In embodiments, n3 is 3. In embodiments, n3 is 4. In embodiments, m3 is 1. In embodiments, m3 is 2. In embodiments, v3 is 1. In embodiments, v3 is 2.

In embodiments, $R^3$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —$NO_2$, —SH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$CH_3$, —$CH_2CH_3$, —$OCH_3$, or —$OCH_2CH_3$. In embodiments, $R^3$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, or —$CH_2I$. In embodiments, $R^3$ is independently oxo. In embodiments, $R^3$ is independently —$CF_3$. In embodiments, $R^3$ is independently halogen. In embodiments, $R^3$ is independently —$CCl_3$. In embodiments, $R^3$ is independently —$CBr_3$. In embodiments, $R^3$ is independently —$CF_3$. In embodiments, $R^3$ is independently —$CI_3$. In embodiments, $R^3$ is independently —$CHCl_2$. In embodiments, $R^3$ is independently —$CHBr_2$. In embodiments, $R^3$ is independently —$CHF_2$. In embodiments, $R^3$ is independently —$CHI_2$. In embodiments, $R^3$ is independently —$CH_2Cl$. In embodiments, $R^3$ is independently —$CH_2Br$. In embodiments, $R^3$ is independently —$CH_2F$. In embodiments, $R^3$ is independently —$CH_2I$. In embodiments, $R^3$ is independently —CN. In embodiments, $R^3$ is independently —OH. In embodiments, $R^3$ is independently —$NH_2$. In embodiments, $R^3$ is independently —COOH. In embodiments, $R^3$ is independently —$CONH_2$. In embodiments, $R^3$ is independently —$NO_2$. In embodiments, $R^3$ is independently —SH. In embodiments, $R^3$ is independently —$SO_3H$. In embodiments, $R^3$ is independently —$SO_4H$. In embodiments, $R^3$ is independently —$SO_2NH_2$. In embodiments, $R^3$ is independently —$NHNH_2$, —$ONH_2$. In embodiments, $R^3$ is independently —NHC(O)$NHNH_2$. In embodiments, $R^3$ is independently —NHC(O)$NH_2$. In embodiments, $R^3$ is independently —$NHSO_2H$. In embodiments, $R^3$ is independently —NHC(O)H. In embodiments, $R^3$ is independently —NHC(O)OH. In embodiments, $R^3$ is independently —NHOH. In embodiments, $R^3$ is independently —$OCCl_3$. In embodiments, $R^3$ is independently —$OCF_3$. In embodiments, $R^3$ is independently —$OCBr_3$. In embodiments, $R^3$ is independently —$OCI_3$. In embodiments, $R^3$ is independently —$OCHCl_2$. In embodiments, $R^3$ is independently —$OCHBr_2$. In embodiments, $R^3$ is independently —$OCHI_2$. In embodiments, $R^3$ is independently —$OCHF_2$. In embodiments, $R^3$ is independently —$OCH_2Cl$. In embodiments, $R^3$ is independently —$OCH_2Br$. In embodiments, $R^3$ is independently —$OCH_2I$.

In embodiments, $R^3$ is independently —$OCH_2F$. In embodiments, $R^3$ is independently —$SF_5$. In embodiments, $R^3$ is independently —$N_3$. In embodiments, $R^3$ is independently —F. In embodiments, $R^3$ is independently —Cl. In embodiments, $R^3$ is independently —Br. In embodiments, $R^3$ is independently —I. In embodiments, $R^3$ is independently —$CH_2OCH_3$. In embodiments, $R^3$ is independently —$SCH_3$. In embodiments, $R^3$ is independently —$OCH_3$. In embodiments, $R^3$ is independently —$CH_2CH_2OCH_3$. In embodiments, $R^3$ is independently —$SCH_2CH_3$. In embodiments, $R^3$ is independently —$OCH_2CH_3$. In embodiments, $R^3$ is independently —$CH_2OCH_2CH_3$. In embodiments, $R^3$ is independently unsubstituted $C_1$-$C_4$ alkyl. In embodiments, $R^3$ is independently unsubstituted cyclopropyl. In embodiments, $R^3$ is independently hydrogen. In embodiments, $R^3$ is independently —$OCH_3$. In embodiments, $R^3$ is independently —$OCH_2CH_3$. In embodiments, $R^3$ is independently —$OCH(CH_3)_2$. In embodiments, $R^3$ is independently —$OC(CH_3)_3$. In embodiments, $R^3$ is independently —$CH_3$. In embodiments, $R^3$ is independently —$CH_2CH_3$. In embodiments, $R^3$ is independently —$CH(CH_3)_2$. In embodiments, $R^3$ is independently —$C(CH_3)_3$. In embodiments, $R^3$ is independently unsubstituted cyclopropyl. In embodiments, $R^3$ is independently unsubstituted cyclobutyl. In embodiments, $R^3$ is independently unsubstituted cyclopentyl. In embodiments, $R^3$ is independently unsubstituted cyclohexyl. In embodiments, $R^3$ is independently substituted or unsubstituted alkyl (e.g., $C_1$-$C_8$, $C_1$-$C_6$, or $C_1$-$C_4$). In embodiments, $R^3$ is independently substituted or unsubstituted heteroalkyl (e.g., 2 to 8 membered, 2 to 6 membered, or 2 to 4 membered). In embodiments, $R^3$ is independently substituted or unsubstituted cycloalkyl (e.g., $C_3$-$C_8$, $C_3$-$C_6$, or $C_5$-$C_6$). In embodiments, $R^3$ is independently substituted or unsubstituted heterocycloalkyl (e.g., 3 to 8 membered, 3 to 6 membered, or 5 to 6 membered). In embodiments, $R^3$ is independently substituted or unsubstituted aryl (e.g., $C_6$-$C_{10}$, $C_{10}$, or phenyl). In embodiments, $R^3$ is independently substituted or unsubstituted heteroaryl (e.g., 5 to 10 membered, 5 to 9 membered, or 5 to 6 membered). In embodiments, $R^3$ is independently unsubstituted alkyl (e.g., $C_1$-$C_8$, $C_1$-$C_6$, or $C_1$-$C_4$). In embodiments, $R^3$ is independently unsubstituted heteroalkyl (e.g., 2 to 8 membered, 2 to 6 membered, or 2 to 4 membered). In embodiments, $R^3$ is independently unsubstituted cycloalkyl (e.g., $C_3$-$C_8$, $C_3$-$C_6$, or $C_5$-$C_6$). In embodiments, $R^3$ is independently unsubstituted heterocycloalkyl (e.g., 3 to 8 membered, 3 to 6 membered, or 5 to 6 membered). In embodiments, $R^3$ is independently unsubstituted aryl (e.g., $C_6$-$C_{10}$, $C_{10}$, or phenyl). In embodiments, $R^3$ is independently unsubstituted heteroaryl (e.g., 5 to 10 membered, 5 to 9 membered, or 5 to 6 membered).

In embodiments, z3 is 0. In embodiments, z3 is 1. In embodiments, z3 is 2. In embodiments, z3 is 3. In embodiments, z3 is 4.

In embodiments, $R^{3A}$, $R^{3B}$, $R^{3C}$, and $R^{3D}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl(e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered); $R^{3A}$ and $R^{3B}$ substituents bonded to the same nitrogen atom may optionally be joined to form a substituted or unsubstituted heterocycloalkyl (e.g., 3 to 8 membered, 3 to 6 membered, or 5 to 6 membered) or substituted or unsubstituted heteroaryl (e.g., 5 to 10 membered, 5 to 9 membered, or 5 to 6 membered).

In embodiments, $R^{3A}$ is independently hydrogen. In embodiments, $R^{3A}$ is independently —$CH_3$. In embodiments, $R^{3A}$ is independently —$CH_2CH_3$. In embodiments, $R^{3A}$ is independently —$CH(CH_3)_2$. In embodiments, $R^{3A}$ is independently —$C(CH_3)_3$. In embodiments, $R^{3A}$ is independently unsubstituted cyclopropyl. In embodiments, $R^{3A}$ is independently unsubstituted cyclobutyl. In embodiments, $R^{3A}$ is independently unsubstituted cyclopentyl. In embodiments, $R^{3A}$ is independently unsubstituted cyclohexyl. In embodiments, $R^{3A}$ is independently substituted or unsubstituted alkyl (e.g., $C_1$-$C_8$, $C_1$-$C_6$, or $C_1$-$C_4$). In embodiments, $R^{3A}$ is independently substituted or unsubstituted heteroalkyl (e.g., 2 to 8 membered, 2 to 6 membered, or 2 to 4 membered). In embodiments, $R^{3A}$ is independently substituted or unsubstituted cycloalkyl (e.g., $C_3$-$C_8$, $C_3$-$C_6$, or $C_5$-$C_6$). In embodiments, $R^{3A}$ is independently substituted or unsubstituted heterocycloalkyl (e.g., 3 to 8 membered, 3 to 6 membered, or 5 to 6 membered). In embodiments, $R^{3A}$ is independently substituted or unsubstituted aryl (e.g., $C_6$-$C_{10}$, $C_{10}$, or phenyl). In embodiments, $R^{3A}$ is independently substituted or unsubstituted heteroaryl (e.g., 5 to 10 membered, 5 to 9 membered, or 5 to 6 membered). In embodiments, $R^{3A}$ is independently unsubstituted alkyl (e.g., $C_1$-$C_8$, $C_1$-$C_6$, or $C_1$-$C_4$). In embodiments, $R^{3A}$ is independently unsubstituted heteroalkyl (e.g., 2 to 8 membered, 2 to 6 membered, or 2 to 4 membered). In embodiments, $R^{3A}$ is independently unsubstituted cycloalkyl (e.g., $C_3$-$C_8$, $C_3$-$C_6$, or $C_5$-$C_6$). In embodiments, $R^{3A}$ is independently unsubstituted heterocycloalkyl (e.g., 3 to 8 membered, 3 to 6 membered, or 5 to 6 membered). In embodiments, $R^{3A}$ is independently unsubstituted aryl (e.g., $C_6$-$C_{10}$, $C_{10}$, or phenyl). In embodiments, $R^{3A}$ is independently unsubstituted heteroaryl (e.g., 5 to 10 membered, 5 to 9 membered, or 5 to 6 membered).

In embodiments, $R^{3B}$ is independently hydrogen. In embodiments, $R^{3B}$ is independently —$CH_3$. In embodiments, $R^{3B}$ is independently —$CH_2CH_3$. In embodiments, $R^{3B}$ is independently —$CH(CH_3)_2$. In embodiments, $R^{3B}$ is independently —$C(CH_3)_3$. In embodiments, $R^{3B}$ is independently unsubstituted cyclopropyl. In embodiments, $R^{3B}$ is independently unsubstituted cyclobutyl. In embodiments, $R^{3B}$ is independently unsubstituted cyclopentyl. In embodiments, $R^{3B}$ is independently unsubstituted cyclohexyl. In embodiments, $R^{3B}$ is independently substituted or unsubstituted alkyl (e.g., $C_1$-$C_8$, $C_1$-$C_6$, or $C_1$-$C_4$). In embodiments, $R^{3B}$ is independently substituted or unsubstituted heteroalkyl (e.g., 2 to 8 membered, 2 to 6 membered, or 2 to 4 membered). In embodiments, $R^{3B}$ is independently substituted or unsubstituted cycloalkyl (e.g., $C_3$-$C_8$, $C_3$-$C_6$, or $C_5$-$C_6$). In embodiments, $R^{3B}$ is independently substituted or unsubstituted heterocycloalkyl (e.g., 3 to 8 membered, 3 to 6 membered, or 5 to 6 membered). In embodiments, $R^{3B}$ is independently substituted or unsubstituted aryl (e.g., $C_6$-$C_{10}$, $C_{10}$, or phenyl). In embodiments, $R^{3B}$ is independently substituted or unsubstituted heteroaryl (e.g., 5 to 10 membered, 5 to 9 membered, or 5 to 6 membered). In embodiments, $R^{3B}$ is independently unsubstituted alkyl (e.g., $C_1$-$C_8$, $C_1$-$C_6$, or $C_1$-$C_4$). In embodiments, $R^{3B}$ is independently unsubstituted heteroalkyl (e.g., 2 to 8 membered, 2 to 6 membered, or 2 to 4 membered). In embodiments, $R^{3B}$ is independently unsubstituted cycloalkyl (e.g., $C_3$-$C_8$, $C_3$-$C_6$, or $C_5$-$C_6$). In embodiments, $R^{3B}$ is independently unsubstituted heterocycloalkyl (e.g., 3 to 8 membered, 3 to 6 membered, or 5 to 6 membered). In embodiments, $R^{3B}$ is independently unsubstituted aryl (e.g., $C_6$-$C_{10}$, $C_{10}$, or phenyl). In embodiments, $R^{3B}$ is independently unsubstituted heteroaryl (e.g., 5 to 10 membered, 5 to 9 membered, or 5 to 6 membered).

In embodiments, $R^{3C}$ is independently hydrogen. In embodiments, $R^{3C}$ is independently —$CH_3$. In embodiments, $R^{3C}$ is independently —$CH_2CH_3$. In embodiments, $R^{3C}$ is independently —$CH(CH_3)_2$. In embodiments, $R^{3C}$ is independently —$C(CH_3)_3$. In embodiments, $R^{3C}$ is independently unsubstituted cyclopropyl. In embodiments, $R^{3C}$ is independently unsubstituted cyclobutyl. In embodiments, $R^{3C}$ is independently unsubstituted cyclopentyl. In embodiments, $R^{3C}$ is independently unsubstituted cyclohexyl. In embodiments, $R^{3C}$ is independently substituted or unsubstituted alkyl (e.g., $C_1$-$C_8$, $C_1$-$C_6$, or $C_1$-$C_4$). In embodiments, $R^{3C}$ is independently substituted or unsubstituted heteroalkyl (e.g., 2 to 8 membered, 2 to 6 membered, or 2 to 4 membered). In embodiments, $R^{3C}$ is independently substituted or unsubstituted cycloalkyl (e.g., $C_3$-$C_8$, $C_3$-$C_6$, or $C_5$-$C_6$). In embodiments, $R^{3C}$ is independently substituted or unsubstituted heterocycloalkyl (e.g., 3 to 8 membered, 3 to 6 membered, or 5 to 6 membered). In embodiments, $R^{3C}$ is independently substituted or unsubstituted aryl (e.g., $C_6$-$C_{10}$, $C_{10}$, or phenyl). In embodiments, $R^{3C}$ is independently substituted or unsubstituted heteroaryl (e.g., 5 to 10 membered, 5 to 9 membered, or 5 to 6 membered). In embodiments, $R^{3C}$ is independently unsubstituted alkyl (e.g., $C_1$-$C_8$, $C_1$-$C_6$, or $C_1$-$C_4$). In embodiments, $R^{3C}$ is independently unsubstituted heteroalkyl (e.g., 2 to 8 membered, 2 to 6 membered, or 2 to 4 membered). In embodiments, $R^{3C}$ is independently unsubstituted cycloalkyl (e.g., $C_3$-$C_8$, $C_3$-$C_6$, or $C_5$-$C_6$). In embodiments, $R^{3C}$ is independently unsubstituted heterocycloalkyl (e.g., 3 to 8 membered, 3 to 6 membered, or 5 to 6 membered). In embodiments, $R^{3C}$ is independently unsubstituted aryl (e.g., $C_6$-$C_{10}$, $C_{10}$, or phenyl). In embodiments, $R^{3C}$ is independently unsubstituted heteroaryl (e.g., 5 to 10 membered, 5 to 9 membered, or 5 to 6 membered).

In embodiments, $R^{3D}$ is independently hydrogen. In embodiments, $R^{3D}$ is independently —$CH_3$. In embodiments, $R^{3D}$ is independently —$CH_2CH_3$. In embodiments, $R^{3D}$ is independently —$CH(CH_3)_2$. In embodiments, $R^{3D}$ is independently —$C(CH_3)_3$. In embodiments, $R^{3D}$ is independently unsubstituted cyclopropyl. In embodiments, $R^{3.1}$ is independently unsubstituted cyclobutyl. In embodiments, $R^{3D}$ is independently unsubstituted cyclopentyl. In embodiments, $R^{3D}$ is independently unsubstituted cyclohexyl. In embodiments, $R^{3D}$ is independently substituted or unsubstituted alkyl (e.g., $C_1$-$C_8$, $C_1$-$C_6$, or $C_1$-$C_4$). In embodiments, $R^{3D}$ is independently substituted or unsubstituted heteroalkyl (e.g., 2 to 8 membered, 2 to 6 membered, or 2 to 4 membered). In embodiments, $R^{3D}$ is independently substituted or unsubstituted cycloalkyl (e.g., $C_3$-$C_8$, $C_3$-$C_6$, or $C_5$-$C_6$). In embodiments, $R^{3.1}$ is independently substituted or unsubstituted heterocycloalkyl (e.g., 3 to 8 membered, 3 to 6 membered, or 5 to 6 membered). In embodiments, $R^{3D}$ is independently substituted or unsubstituted aryl (e.g., $C_6$-$C_{10}$, $C_{10}$, or phenyl). In embodiments, $R^{3D}$ is independently substituted or unsubstituted heteroaryl (e.g., 5 to 10 membered, 5 to 9 membered, or 5 to 6 membered). In embodiments, $R^{3D}$ is independently unsubstituted alkyl (e.g., $C_1$-$C_8$, $C_1$-$C_6$, or $C_1$-$C_4$). In embodiments, $R^{3D}$ is independently unsubstituted heteroalkyl (e.g., 2 to 8 membered, 2 to 6 membered, or 2 to 4 membered). In embodiments, $R^{3D}$ is independently unsubstituted cycloalkyl (e.g., $C_3$-$C_8$, $C_3$-$C_6$, or $C_5$-$C_6$). In embodiments, $R^{3D}$ is independently unsubstituted heterocycloalkyl (e.g., 3 to 8 membered, 3 to 6 membered, or 5 to 6 membered). In embodiments, $R^{3.1}$ is independently unsubstituted aryl (e.g., $C_6$-$C_{10}$, $C_{10}$, or phenyl). In embodiments, $R^{3.1}$ is independently unsubstituted heteroaryl (e.g., 5 to 10 membered, 5 to 9 membered, or 5 to 6 membered).

In embodiments, $R^4$ is independently —$NR^{4A}R^{4B}$; and $R^{4A}$ and $R^{4B}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, or unsubstituted $C_1$-$C_4$ alkyl.

In embodiments, $R^4$ is independently —$NH_2$.

In embodiments, $R^4$ is independently oxo, halogen, oxo, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted alkyl (e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered); two adjacent $R^4$ substituents may optionally be joined to form a substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered).

In embodiments, z4 is an integer from 0 to 4.

In embodiments, $R^4$ is independently oxo. In embodiments, $R^4$ is independently —$CF_3$.

In embodiments, $R^4$ is independently halogen. In embodiments, $R^4$ is independently —$CCl_3$. In embodiments, $R^4$ is independently —$CBr_3$. In embodiments, $R^4$ is independently —$CF_3$. In embodiments, $R^4$ is independently —$CI_3$. In embodiments, $R^4$ is independently —$CHCl_2$. In embodiments, $R^4$ is independently —$CHBr_2$. In embodiments, $R^4$ is independently —$CHF_2$. In embodiments, $R^4$ is independently —$CHI_2$. In embodiments, $R^4$ is independently —$CH_2Cl$. In embodiments, $R^4$ is independently —$CH_2Br$. In embodiments, $R^4$ is independently —$CH_2F$. In embodiments, $R^4$ is independently —$CH_2I$. In embodiments, $R^4$ is independently —CN. In embodiments, $R^4$ is independently —OH. In embodiments, $R^4$ is independently —$NH_2$. In embodiments, $R^4$ is independently —COOH. In embodiments, $R^4$ is independently —$CONH_2$. In embodiments, $R^4$ is independently —$NO_2$. In embodiments, $R^4$ is independently —SH. In embodiments, $R^4$ is independently —$SO_3H$. In embodiments, $R^4$ is independently —$SO_4H$. In embodiments, $R^4$ is independently —$SO_2NH_2$. In embodiments, $R^4$ is independently —$NHNH_2$. In embodiments, $R^4$ is independently —$ONH_2$. In embodiments, $R^4$ is independently —NHC(O)$NHNH_2$. In embodiments, $R^4$ is independently —$NHC(O)NH_2$. In embodiments, $R^4$ is independently —$NHSO_2H$. In embodiments, $R^4$ is independently —NHC(O)H. In embodiments, $R^4$ is independently —NHC(O)OH. In embodiments, $R^4$ is independently —NHOH. In embodiments, $R^4$ is independently —$OCCl_3$. In embodiments, $R^4$ is independently —$OCF_3$. In embodiments, $R^4$ is independently —$OCBr_3$. In embodiments, $R^4$ is independently —$OCI_3$. In embodiments, $R^4$ is independently —$OCHCl_2$. In embodiments, $R^4$ is independently —$OCHBr_2$. In embodiments, $R^4$ is independently —$OCHI_2$. In embodiments, $R^4$ is independently —$OCHF_2$. In embodiments, $R^4$ is independently —$OCH_2Cl$. In embodiments, $R^4$ is independently —$OCH_2Br$. In embodiments, $R^4$ is independently —$OCH_2I$. In embodiments, $R^4$ is independently —$OCH_2F$. In embodiments, $R^4$ is independently —$SF_5$. In embodiments, $R^4$ is independently —$N_3$. In embodiments, $R^4$ is independently —F. In embodiments, $R^4$ is independently —Cl. In embodiments, $R^4$ is independently —Br. In embodiments, $R^4$ is independently —I. In embodiments, $R^4$ is independently —$CH_2OCH_3$. In embodiments, $R^4$ is independently —$SCH_3$. In embodiments, $R^4$ is independently —$OCH_3$. In embodiments, $R^4$ is independently —$CH_2CH_2OCH_3$. In embodiments, $R^4$ is independently —$SCH_2CH_3$. In embodiments, $R^4$ is independently —$OCH_2CH_3$. In embodiments, $R^4$ is independently —$CH_2OCH_2CH_3$. In embodiments, $R^4$ is independently unsubstituted $C_1$-$C_4$ alkyl. In embodiments, $R^4$ is independently unsubstituted cyclopropyl. In embodiments, $R^4$ is independently hydrogen. In embodiments, $R^4$ is independently —$OCH_3$. In embodiments, $R^4$ is independently —$OCH_2CH_3$. In embodiments, $R^4$ is independently —$OCH(CH_3)_2$. In embodiments, $R^4$ is independently —$OC(CH_3)_3$. In embodiments, $R^4$ is independently —$CH_3$. In embodiments, $R^4$ is independently —$CH_2CH_3$. In embodiments, $R^4$ is independently —$CH(CH_3)_2$. In embodiments, $R^4$ is independently —$C(CH_3)_3$. In embodiments, $R^4$ is independently unsubstituted cyclopropyl. In embodiments, $R^4$ is independently unsubstituted cyclobutyl. In embodiments, $R^4$ is independently unsubstituted cyclopentyl. In embodiments, $R^4$ is independently unsubstituted cyclohexyl. In embodiments, $R^4$ is independently substituted or unsubstituted alkyl (e.g., $C_1$-$C_8$, $C_1$-$C_6$, or $C_1$-$C_4$). In embodiments, $R^4$ is independently substituted or unsubstituted heteroalkyl (e.g., 2 to 8 membered, 2 to 6 membered, or 2 to 4 membered). In embodiments, $R^4$ is independently substituted or unsubstituted cycloalkyl (e.g., $C_3$-$C_8$, $C_3$-$C_6$, or $C_5$-$C_6$). In embodiments, $R^4$ is independently substituted or unsubstituted heterocycloalkyl (e.g., 3 to 8 membered, 3 to 6 membered, or 5 to 6 membered). In embodiments, $R^4$ is independently substituted or unsubstituted aryl (e.g., $C_6$-$C_{10}$, $C_{10}$, or phenyl). In embodiments, $R^4$ is independently substituted or unsubstituted heteroaryl (e.g., 5 to 10 membered, 5 to 9 membered, or 5 to 6 membered). In embodiments, $R^4$ is independently unsubstituted alkyl (e.g., $C_1$-$C_8$, $C_1$-$C_6$, or $C_1$-$C_4$). In embodiments, $R^4$ is independently unsubstituted heteroalkyl (e.g., 2 to 8 membered, 2 to 6 membered, or 2 to 4 membered). In embodiments, $R^4$ is independently unsubstituted cycloalkyl (e.g., $C_3$-$C_8$, $C_3$-$C_6$, or $C_5$-$C_6$). In embodiments, $R^4$ is independently unsubstituted heterocycloalkyl (e.g., 3 to 8 membered, 3 to 6 membered, or 5 to 6 membered). In embodiments, $R^4$ is independently unsubstituted aryl (e.g., $C_6$-$C_{10}$, $C_{10}$, or phenyl). In embodiments, $R^4$ is independently unsubstituted heteroaryl (e.g., 5 to 10 membered, 5 to 9 membered, or 5 to 6 membered).

In embodiments, z4 is 0. In embodiments, z4 is 1. In embodiments, z4 is 2. In embodiments, z4 is 3. In embodiments, z4 is 4. In embodiments, $X^4$ is independently —F. In embodiments, $X^4$ is independently —Cl. In embodiments, $X^4$ is independently —Br. In embodiments, $X^4$ is independently —I. In embodiments, n4 is 0. In embodiments, n4 is 1. In embodiments, n4 is 2. In embodiments, n4 is 3. In embodiments, n4 is 4. In embodiments, m4 is 1. In embodiments, m4 is 2. In embodiments, v4 is 1. In embodiments, v4 is 2.

In embodiments, $R^{4A}$, $R^{4B}$, $R^{4C}$, and $R^{4D}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl(e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered); $R^{4A}$ and $R^{4B}$ substituents bonded to the same nitrogen atom may optionally be joined to form a substituted or unsubstituted heterocycloalkyl (e.g., 3 to 8 membered, 3 to 6 membered, or 5 to 6 membered) or substituted or unsubstituted heteroaryl (e.g., 5 to 10 membered, 5 to 9 membered, or 5 to 6 membered).

In embodiments, $R^{4A}$ is independently hydrogen. In embodiments, $R^{4A}$ is independently —$CH_3$. In embodiments, $R^{4A}$ is independently —$CH_2CH_3$. In embodiments, $R^{4A}$ is independently —$CH(CH_3)_2$. In embodiments, $R^{4A}$ is independently —$C(CH_3)_3$. In embodiments, $R^{4A}$ is independently unsubstituted cyclopropyl. In embodiments, $R^{4A}$ is independently unsubstituted cyclobutyl. In embodiments, $R^{4A}$ is independently unsubstituted cyclopentyl. In embodiments, $R^{4A}$ is independently unsubstituted cyclohexyl. In embodiments, $R^{4A}$ is independently substituted or unsubstituted alkyl (e.g., $C_1$-$C_8$, $C_1$-$C_6$, or $C_1$-$C_4$). In embodiments, $R^{4A}$ is independently substituted or unsubstituted heteroalkyl (e.g., 2 to 8 membered, 2 to 6 membered, or 2 to 4 membered). In embodiments, $R^{4A}$ is independently substituted or unsubstituted cycloalkyl (e.g., $C_3$-$C_8$, $C_3$-$C_6$, or $C_5$-$C_6$). In embodiments, $R^{4A}$ is independently substituted or unsubstituted heterocycloalkyl (e.g., 3 to 8 membered, 3 to 6 membered, or 5 to 6 membered). In embodiments, $R^{4A}$ is independently substituted or unsubstituted aryl (e.g., $C_6$-$C_{10}$, $C_{10}$, or phenyl). In embodiments, $R^{4A}$ is independently substituted or unsubstituted heteroaryl (e.g., 5 to 10 membered, 5 to 9 membered, or 5 to 6 membered). In embodiments, $R^{4A}$ is independently unsubstituted alkyl (e.g., $C_1$-$C_8$, $C_1$-$C_6$, or $C_1$-$C_4$). In embodiments, $R^{4A}$ is independently unsubstituted heteroalkyl (e.g., 2 to 8 membered, 2 to 6 membered, or 2 to 4 membered). In embodiments, $R^{4A}$ is independently unsubstituted cycloalkyl (e.g., $C_3$-$C_8$, $C_3$-$C_6$, or $C_5$-$C_6$). In embodiments, $R^{4A}$ is independently unsubstituted heterocycloalkyl (e.g., 3 to 8 membered, 3 to 6 membered, or 5 to 6 membered). In embodiments, $R^{4A}$ is independently unsubstituted aryl (e.g., $C_6$-$C_{10}$, $C_{10}$, or phenyl). In embodiments, $R^{4A}$ is independently unsubstituted heteroaryl (e.g., 5 to 10 membered, 5 to 9 membered, or 5 to 6 membered).

In embodiments, $R^{4B}$ is independently hydrogen. In embodiments, $R^{4B}$ is independently —$CH_3$. In embodiments, $R^{4B}$ is independently —$CH_2CH_3$. In embodiments, $R^{4B}$ is independently —$CH(CH_3)_2$. In embodiments, $R^{4B}$ is independently —$C(CH_3)_3$. In embodiments, $R^{4B}$ is independently unsubstituted cyclopropyl. In embodiments, $R^{4B}$ is independently unsubstituted cyclobutyl. In embodiments, $R^{4B}$ is independently unsubstituted cyclopentyl. In embodiments, $R^{4B}$ is independently unsubstituted cyclohexyl. In embodiments, $R^{4B}$ is independently substituted or unsubstituted alkyl (e.g., $C_1$-$C_8$, $C_1$-$C_6$, or $C_1$-$C_4$). In embodiments, $R^{4B}$ is independently substituted or unsubstituted heteroalkyl (e.g., 2 to 8 membered, 2 to 6 membered, or 2 to 4 membered). In embodiments, $R^{4B}$ is independently substituted or unsubstituted cycloalkyl (e.g., $C_3$-$C_8$, $C_3$-$C_6$, or $C_5$-$C_6$). In embodiments, $R^{4B}$ is independently substituted or unsubstituted heterocycloalkyl (e.g., 3 to 8 membered, 3 to 6 membered, or 5 to 6 membered). In embodiments, $R^{4B}$ is independently substituted or unsubstituted aryl (e.g., $C_6$-$C_{10}$, $C_{10}$, or phenyl). In embodiments, $R^{4B}$ is independently substituted or unsubstituted heteroaryl (e.g., 5 to 10 membered, 5 to 9 membered, or 5 to 6 membered). In embodiments, $R^{4B}$ is independently unsubstituted alkyl (e.g., $C_1$-$C_8$, $C_1$-$C_6$, or $C_1$-$C_4$). In embodiments, $R^{4B}$ is independently unsubstituted heteroalkyl (e.g., 2 to 8 membered, 2 to 6 membered, or 2 to 4 membered). In embodiments, $R^{4B}$ is independently unsubstituted cycloalkyl (e.g., $C_3$-$C_8$, $C_3$-$C_6$, or $C_5$-$C_6$). In embodiments, $R^{4B}$ is independently unsubstituted heterocycloalkyl (e.g., 3 to 8 membered, 3 to 6 membered, or 5 to 6 membered). In embodiments, $R^{4B}$ is independently unsubstituted aryl (e.g., $C_6$-$C_{10}$, $C_{10}$, or phenyl). In embodiments, $R^{4B}$ is independently unsubstituted heteroaryl (e.g., 5 to 10 membered, 5 to 9 membered, or 5 to 6 membered).

In embodiments, $R^{4C}$ is independently hydrogen. In embodiments, $R^{4C}$ is independently $-CH_3$. In embodiments, $R^{4C}$ is independently $-CH_2CH_3$. In embodiments, $R^{4C}$ is independently $-CH(CH_3)_2$. In embodiments, $R^{4C}$ is independently $-C(CH_3)_3$. In embodiments, $R^{4C}$ is independently unsubstituted cyclopropyl. In embodiments, $R^{4C}$ is independently unsubstituted cyclobutyl. In embodiments, $R^{4C}$ is independently unsubstituted cyclopentyl. In embodiments, $R^{4C}$ is independently unsubstituted cyclohexyl. In embodiments, $R^{4C}$ is independently substituted or unsubstituted alkyl (e.g., $C_1$-$C_8$, $C_1$-$C_6$, or $C_1$-$C_4$). In embodiments, $R^{4C}$ is independently substituted or unsubstituted heteroalkyl (e.g., 2 to 8 membered, 2 to 6 membered, or 2 to 4 membered). In embodiments, $R^{4C}$ is independently substituted or unsubstituted cycloalkyl (e.g., $C_3$-$C_8$, $C_3$-$C_6$, or $C_5$-$C_6$). In embodiments, $R^{4C}$ is independently substituted or unsubstituted heterocycloalkyl (e.g., 3 to 8 membered, 3 to 6 membered, or 5 to 6 membered). In embodiments, $R^{4C}$ is independently substituted or unsubstituted aryl (e.g., $C_6$-$C_{10}$, $C_{10}$, or phenyl). In embodiments, $R^{4C}$ is independently substituted or unsubstituted heteroaryl (e.g., 5 to 10 membered, 5 to 9 membered, or 5 to 6 membered). In embodiments, $R^{4C}$ is independently unsubstituted alkyl (e.g., $C_1$-$C_8$, $C_1$-$C_6$, or $C_1$-$C_4$). In embodiments, $R^{4C}$ is independently unsubstituted heteroalkyl (e.g., 2 to 8 membered, 2 to 6 membered, or 2 to 4 membered). In embodiments, $R^{4C}$ is independently unsubstituted cycloalkyl (e.g., $C_3$-$C_8$, $C_3$-$C_6$, or $C_5$-$C_6$). In embodiments, $R^{4C}$ is independently unsubstituted heterocycloalkyl (e.g., 3 to 8 membered, 3 to 6 membered, or 5 to 6 membered). In embodiments, $R^{4C}$ is independently unsubstituted aryl (e.g., $C_6$-$C_{10}$, $C_{10}$, or phenyl). In embodiments, $R^{4C}$ is independently unsubstituted heteroaryl (e.g., 5 to 10 membered, 5 to 9 membered, or 5 to 6 membered).

In embodiments, $R^{4D}$ is independently hydrogen. In embodiments, $R^{4D}$ is independently $-CH_3$. In embodiments, $R^{4D}$ is independently $-CH_2CH_3$. In embodiments, $R^{4D}$ is independently $-CH(CH_3)_2$. In embodiments, $R^{4D}$ is independently $-C(CH_3)_3$. In embodiments, $R^{4D}$ is independently unsubstituted cyclopropyl. In embodiments, $R^{4D}$ is independently unsubstituted cyclobutyl. In embodiments, $R^{4D}$ is independently unsubstituted cyclopentyl. In embodiments, $R^{4D}$ is independently unsubstituted cyclohexyl. In embodiments, $R^{4D}$ is independently substituted or unsubstituted alkyl (e.g., $C_1$-$C_8$, $C_1$-$C_6$, or $C_1$-$C_4$). In embodiments, $R^{4D}$ is independently substituted or unsubstituted heteroalkyl (e.g., 2 to 8 membered, 2 to 6 membered, or 2 to 4 membered). In embodiments, $R^{4D}$ is independently substituted or unsubstituted cycloalkyl (e.g., $C_3$-$C_8$, $C_3$-$C_6$, or $C_5$-$C_6$). In embodiments, $R^{4D}$ is independently substituted or unsubstituted heterocycloalkyl (e.g., 3 to 8 membered, 3 to 6 membered, or 5 to 6 membered). In embodiments, $R^{4D}$ is independently substituted or unsubstituted aryl (e.g., $C_6$-$C_{10}$, $C_{10}$, or phenyl). In embodiments, $R^{4D}$ is independently substituted or unsubstituted heteroaryl (e.g., 5 to 10 membered, 5 to 9 membered, or 5 to 6 membered). In embodiments, $R^{4D}$ is independently unsubstituted alkyl (e.g., $C_1$-$C_8$, $C_1$-$C_6$, or $C_1$-$C_4$). In embodiments, $R^{4D}$ is independently unsubstituted heteroalkyl (e.g., 2 to 8 membered, 2 to 6 membered, or 2 to 4 membered). In embodiments, $R^{4D}$ is independently unsubstituted cycloalkyl (e.g., $C_3$-$C_8$, $C_3$-$C_6$, or $C_5$-$C_6$). In embodiments, $R^{4D}$ is independently unsubstituted heterocycloalkyl (e.g., 3 to 8 membered, 3 to 6 membered, or 5 to 6 membered). In embodiments, $R^{4D}$ is independently unsubstituted aryl (e.g., $C_6$-$C_{10}$, $C_{10}$, or phenyl). In embodiments, $R^{4D}$ is independently unsubstituted heteroaryl (e.g., 5 to 10 membered, 5 to 9 membered, or 5 to 6 membered).

In embodiments, $R^5$ is substituted or unsubstituted alkyl, substituted or unsubstituted cycloalkyl, substituted or unsubstituted heterocycloalkyl, substituted or unsubstituted aryl, or substituted or unsubstituted heteroaryl; In embodiments, $R^5$ is substituted or unsubstituted $C_1$-$C_4$ alkyl, substituted or unsubstituted 2 to 4 membered heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is substituted or unsubstituted $C_1$-$C_4$ alkyl, substituted or unsubstituted cycloalkyl, substituted or unsubstituted heterocycloalkyl, substituted or unsubstituted aryl, or substituted or unsubstituted heteroaryl.

In embodiments, $R^5$ is substituted or unsubstituted alkyl (e.g., $C_1$-$C_8$, $C_1$-$C_6$, or $C_1$-$C_4$), substituted or unsubstituted heteroalkyl (e.g., 2 to 8 membered, 2 to 6 membered, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered). In embodiments, $R^5$ is substituted or unsubstituted alkyl (e.g., $C_1$-$C_8$, $C_1$-$C_6$, or $C_1$-$C_4$), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered).

In embodiments, $R^5$ is $-CCl_3$. In embodiments, $R^5$ is $-CBr_3$. In embodiments, $R^5$ is $-CF_3$. In embodiments, $R^5$ is $-CI_3$. In embodiments, $R^5$ is $-CHCl_2$. In embodiments, $R^5$ is $-CHBr_2$. In embodiments, $R^5$ is $-CHF_2$. In embodiments, $R^5$ is $-CHI_2$. In embodiments, $R^5$ is $-CH_2Cl$. In embodiments, $R^5$ is $-CH_2Br$. In embodiments, $R^5$ is $-CH_2F$. In embodiments, $R^5$ is $-CH_2I$. In embodiments, $R^5$ is unsubstituted $C_1$-$C_4$ alkyl. In embodiments, $R^5$ is unsubstituted cyclopropyl. In embodiments, $R^5$ is —$CH_3$. In embodiments, $R^5$ is —$CH_2CH_3$. In embodiments, $R^5$ is —$CH(CH_3)_2$. In embodiments, $R^5$ is —$C(CH_3)_3$. In embodiments, $R^5$ is unsubstituted cyclopropyl. In embodiments, $R^5$ is unsubstituted cyclobutyl. In embodiments, $R^5$ is unsubstituted cyclopentyl. In embodiments, $R^5$ is unsubstituted cyclohexyl. In embodiments, $R^5$ is substituted or unsubstituted alkyl (e.g., $C_1$-$C_8$, $C_1$-$C_6$, or $C_1$-$C_4$). In embodiments, $R^5$ is substituted or unsubstituted heteroalkyl (e.g., 2 to 8 membered, 2 to 6 membered, or 2 to 4 membered). In embodiments, $R^5$ is substituted or unsubstituted cycloalkyl (e.g., $C_3$-$C_8$, $C_3$-$C_6$, or $C_5$-$C_6$). In embodiments, $R^5$ is substituted or unsubstituted heterocycloalkyl (e.g., 3 to 8 membered, 3 to 6 membered, or 5 to 6 membered). In embodiments, $R^5$ is substituted or unsubstituted aryl (e.g., $C_6$-$C_{10}$, $C_{10}$, or phenyl). In embodiments, $R^5$ is substituted or unsubstituted heteroaryl (e.g., 5 to 10 membered, 5 to 9 membered, or 5 to 6 membered). In embodiments, $R^5$ is unsubstituted alkyl (e.g., $C_1$-$C_8$, $C_1$-$C_6$, or $C_1$-$C_4$). In embodiments, $R^5$ is unsubstituted heteroalkyl (e.g., 2 to 8 membered, 2 to 6 membered, or 2 to 4 membered). In embodiments, $R^5$ is unsubstituted cycloalkyl (e.g., $C_3$-$C_8$, $C_3$-$C_6$, or $C_5$-$C_6$). In embodiments, $R^5$ is unsubstituted heterocycloalkyl (e.g., 3 to 8 membered, 3 to 6 membered, or 5 to 6 membered). In embodiments, $R^5$ is unsubstituted aryl (e.g., $C_6$-$C_{10}$, $C_{10}$, or phenyl). In embodiments, $R^5$ is unsubstituted heteroaryl (e.g., 5 to 10 membered, 5 to 9 membered, or 5 to 6 membered).

In embodiments, Ring A is cycloalkyl (e.g., $C_3$-$C_8$, $C_3$-$C_6$, or $C_5$-$C_6$), heterocycloalkyl (e.g., 3 to 8 membered, 3 to 6 membered, or 5 to 6 membered), aryl (e.g., $C_6$-$C_{10}$, $C_{10}$, or phenyl), or heteroaryl (e.g., 5 to 10 membered, 5 to 9 membered, or 5 to 6 membered).

In embodiments, Ring A is $C_5$-$C_6$ cycloalkyl, 5 to 6 membered heterocycloalkyl, phenyl, or 5 to 6 membered heteroaryl.

In embodiments, Ring A is $C_5$-$C_6$ cycloalkyl. In embodiments, Ring A is 5 to 6 membered heterocycloalkyl. In embodiments, Ring A is phenyl. In embodiments, Ring A is 5 to 6 membered heteroaryl.

In embodiments, Ring A is 5 membered heteroaryl. In embodiments, Ring A is triazolyl. In embodiments, Ring A is 1,2,4-triazolyl. In embodiments, Ring A is pyrrolyl. In embodiments, Ring A is pyrazolyl. In embodiments, Ring A is imidazolyl. In embodiments, Ring A is tetrazolyl. In embodiments, Ring A is furanyl. In embodiments, Ring A is thienyl. In embodiments, Ring A is oxazolyl. In embodiments, Ring A is isoxazolyl. In embodiments, Ring A is thiazolyl. In embodiments, Ring A is isothiazolyl. In embodiments, Ring A is oxadiazolyl. In embodiments, Ring A is thiadiazolyl.

In embodiments, Ring A is $C_3$-$C_6$ cycloalkyl. In embodiments, Ring A is $C_4$-$C_6$ cycloalkyl. In embodiments, Ring A is $C_5$-$C_6$ cycloalkyl. In embodiments, Ring A is $C_3$ cycloalkyl. In embodiments, Ring A is $C_4$ cycloalkyl. In embodiments, Ring A is $C_5$ cycloalkyl. In embodiments, Ring A is $C_6$ cycloalkyl. In embodiments, Ring A is $C_3$ cycloalkenyl. In embodiments, Ring A is $C_4$ cycloalkenyl. In embodiments, Ring A is $C_5$ cycloalkenyl. In embodiments, Ring A is $C_6$ cycloalkenyl.

In embodiments, Ring A is 3 to 6 membered heterocycloalkyl. In embodiments, Ring A is 4 to 6 membered heterocycloalkyl. In embodiments, Ring A is 5 to 6 membered heterocycloalkyl. In embodiments, Ring A is 3 membered heterocycloalkyl. In embodiments, Ring A is 4 membered heterocycloalkyl. In embodiments, Ring A is 5 membered heterocycloalkyl. In embodiments, Ring A is 6 membered heterocycloalkyl. In embodiments, Ring A is 3 membered heterocycloalkenyl. In embodiments, Ring A is 4 membered heterocycloalkenyl. In embodiments, Ring A is 5 membered heterocycloalkenyl. In embodiments, Ring A is 6 membered heterocycloalkenyl.

In embodiments, Ring A is phenyl. In embodiments, Ring A is 5 to 6 membered heteroaryl. In embodiments, Ring A is 6 membered heteroaryl.

In embodiments, Ring B is cycloalkyl (e.g., $C_3$-$C_8$, $C_3$-$C_6$, or $C_5$-$C_6$), heterocycloalkyl (e.g., 3 to 8 membered, 3 to 6 membered, or 5 to 6 membered), aryl (e.g., $C_6$-$C_{10}$, $C_{10}$, or phenyl), or heteroaryl (e.g., 5 to 10 membered, 5 to 9 membered, or 5 to 6 membered).

In embodiments, Ring B is $C_3$-$C_6$ cycloalkyl, 3 to 6 membered heterocycloalkyl, phenyl, or 5 to 6 membered heteroaryl.

In embodiments, Ring B is $C_3$-$C_6$ cycloalkyl. In embodiments, Ring B is 3 to 6 membered heterocycloalkyl.

In embodiments, Ring B is $C_5$-$C_6$ cycloalkyl, 5 to 6 membered heterocycloalkyl, phenyl, or 5 to 6 membered heteroaryl.

In embodiments, Ring B is $C_5$-$C_6$ cycloalkyl. In embodiments, Ring B is 5 to 6 membered heterocycloalkyl. In embodiments, Ring B is phenyl. In embodiments, Ring B is 5 to 6 membered heteroaryl.

In embodiments, Ring B is 5 membered heteroaryl. In embodiments, Ring B is triazolyl. In embodiments, Ring B is 1,2,4-triazolyl. In embodiments, Ring B is pyrrolyl. In embodiments, Ring B is pyrazolyl. In embodiments, Ring B is imidazolyl. In embodiments, Ring B is tetrazolyl. In embodiments, Ring B is furanyl. In embodiments, Ring B is thienyl. In embodiments, Ring B is oxazolyl. In embodiments, Ring B is isoxazolyl. In embodiments, Ring B is thiazolyl. In embodiments, Ring B is isothiazolyl. In embodiments, Ring B is oxadiazolyl. In embodiments, Ring B is thiadiazolyl.

In embodiments, Ring B is $C_3$-$C_6$ cycloalkyl. In embodiments, Ring B is $C_4$-$C_6$ cycloalkyl. In embodiments, Ring B is $C_5$-$C_6$ cycloalkyl. In embodiments, Ring B is $C_3$ cycloalkyl. In embodiments, Ring B is $C_4$ cycloalkyl. In embodiments, Ring B is $C_5$ cycloalkyl. In embodiments, Ring B is $C_6$ cycloalkyl. In embodiments, Ring B is $C_3$ cycloalkenyl. In embodiments, Ring B is $C_4$ cycloalkenyl. In embodiments, Ring B is $C_5$ cycloalkenyl. In embodiments, Ring B is $C_6$ cycloalkenyl.

In embodiments, Ring B is 3 to 6 membered heterocycloalkyl. In embodiments, Ring B is 4 to 6 membered heterocycloalkyl. In embodiments, Ring B is 5 to 6 membered heterocycloalkyl. In embodiments, Ring B is 3 membered heterocycloalkyl. In embodiments, Ring B is 4 membered heterocycloalkyl. In embodiments, Ring B is 5 membered heterocycloalkyl. In embodiments, Ring B is 6 membered heterocycloalkyl. In embodiments, Ring B is 3 membered heterocycloalkenyl. In embodiments, Ring B is 4 membered heterocycloalkenyl. In embodiments, Ring B is 5 membered heterocycloalkenyl. In embodiments, Ring B is 6 membered heterocycloalkenyl.

In embodiments, Ring B is phenyl. In embodiments, Ring B is 5 to 6 membered heteroaryl. In embodiments, Ring B is 6 membered heteroaryl.

In embodiments, a substituted $R^1$ (e.g., substituted alkyl, substituted heteroalkyl, substituted cycloalkyl, and/or substituted heterocycloalkyl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, a substituted $R^{1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1A}$ is substituted with a plurality of groups selected from substituent groups, size-limited substituent groups, and lower substituent groups; each substituent group, size-limited substituent group, and/or lower substituent group may optionally be different. In embodiments, when $R^{1A}$ is substituted, it is substituted with at least one substituent group. In embodiments, when $R^{1A}$ is substituted, it is substituted with at least one size-limited substituent group. In embodiments, when $R^{1A}$ is substituted, it is substituted with at least one lower substituent group.

In embodiments, a substituted RB (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted RB is substituted with a plurality of groups selected from substituent groups, size-limited substituent groups, and lower substituent groups; each substituent group, size-limited substituent group, and/or lower substituent group may optionally be different. In embodiments, when RB is substituted, it is substituted with at least one substituent group. In embodiments, when RB is substituted, it is substituted with at least one size-limited substituent group. In embodiments, when RB is substituted, it is substituted with at least one lower substituent group.

In embodiments, a substituted ring formed when $R^{1A}$ and RB substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{1A}$ and RB substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{1A}$ and $R^{1B}$ substituents bonded to the same nitrogen atom are joined is substituted, it is substituted with at least one substituent group. In embodiments, when the substituted ring formed when $R^{1A}$ and $R^{1B}$, substituents bonded to the same nitrogen atom are joined is substituted, it is substituted with at least one size-limited substituent group. In embodiments, when the substituted ring formed when $R^{1A}$ and $R^{1B}$ substituents bonded to the same nitrogen atom are joined is substituted, it is substituted with at least one lower substituent group.

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, a substituted ring formed when two $R^2$ substituents are joined (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed when two $R^2$ substituents are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two $R^2$ substituents are joined is substituted, it is substituted with at least one substituent group. In embodiments, when the substituted ring formed when two $R^2$ substituents are joined is substituted, it is substituted with at least one size-limited substituent group. In embodiments, when the substituted ring formed when two $R^z$ substituents are joined is substituted, it is substituted with at least one lower substituent group.

In embodiments, a substituted $R^{2A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^{2A}$ is substituted, it is substituted with at least one substituent group. In embodiments, when $R^{2A}$ is substituted, it is substituted with at least one size-limited substituent group. In embodiments, when $R^{2A}$ is substituted, it is substituted with at least one lower substituent group.

In embodiments, a substituted $R^{2B}$, (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2B}$, is substituted with a plurality of groups selected from substituent groups, size-limited substituent groups, and lower substituent groups; each substituent group, size-limited substituent group, and/or lower substituent group may optionally be different. In embodiments, when $R^{2B}$, is substituted, it is substituted with at least one substituent group. In embodiments, when $R^{2B}$, is substituted, it is substituted with at least one size-limited substituent group. In embodiments, when $R^{2B}$, is substituted, it is substituted with at least one lower substituent group.

In embodiments, a substituted ring formed when $R^{2A}$ and $R^{2B}$, substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{2A}$ and $R^{2B}$, substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{2A}$ and $R^{2B}$, substituents bonded to the same nitrogen atom are joined is substituted, it is substituted with at least one substituent group. In embodiments, when the substituted ring formed when $R^{2A}$ and $R^{2B}$, substituents bonded to the same nitrogen atom are joined is substituted, it is substituted with at least one size-limited substituent group. In embodiments, when the substituted ring formed when $R^{2A}$ and $R^{2B}$ substituents bonded to the same nitrogen atom are joined is substituted, it is substituted with at least one lower substituent group.

In embodiments, a substituted $R^{2C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2C}$ is substituted with a plurality of groups selected from substituent groups, size-limited substituent groups, and lower substituent groups; each substituent group, size-limited substituent group, and/or lower substituent group may optionally be different. In embodiments, when $R^{2C}$ is substituted, it is substituted with at least one substituent group. In embodiments, when $R^{2C}$ is substituted, it is substituted with at least one size-limited substituent group. In embodiments, when $R^{2C}$ is substituted, it is substituted with at least one lower substituent group.

In embodiments, a substituted $R^{2D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2D}$ is substituted with a plurality of groups selected from substituent groups, size-limited substituent groups, and lower substituent groups; each substituent group, size-limited substituent group, and/or lower substituent group may optionally be different. In embodiments, when $R^{2D}$ is substituted, it is substituted with at least one substituent group. In embodiments, when $R^{2D}$ is substituted, it is substituted with at least one size-limited substituent group. In embodiments, when $R^{2D}$ is substituted, it is substituted with at least one lower substituent group.

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, a substituted ring formed when two $R^3$ substituents are joined (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed when two $R^3$ substituents are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two $R^3$ substituents are joined is substituted, it is substituted with at least one substituent group. In embodiments, when the substituted ring formed when two $R^3$ substituents are joined is substituted, it is substituted with at least one size-limited substituent group. In embodiments, when the substituted ring formed when two $R^3$ substituents are joined is substituted, it is substituted with at least one lower substituent group.

In embodiments, a substituted $R^{3A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3A}$ is substituted with a plurality of groups selected from substituent groups, size-limited substituent groups, and lower substituent groups; each substituent group, size-limited substituent group, and/or lower substituent group may optionally be different. In embodiments, when $R^{3A}$ is substituted, it is substituted with at least one substituent group. In embodiments, when $R^{3A}$ is substituted, it is substituted with at least one size-limited substituent group. In embodiments, when $R^{3A}$ is substituted, it is substituted with at least one lower substituent group.

In embodiments, a substituted $R^{3B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3B}$ is substituted with a plurality of groups selected from substituent groups, size-limited substituent groups, and lower substituent groups; each substituent group, size-limited substituent group, and/or lower substituent group may optionally be different. In embodiments, when $R^{3B}$ is substituted, it is substituted with at least one substituent group. In embodiments, when $R^{3B}$ is substituted, it is substituted with at least one size-limited substituent group. In embodiments, when $R^{3B}$ is substituted, it is substituted with at least one lower substituent group.

In embodiments, a substituted ring formed when $R^{3A}$ and $R^{3B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{3A}$ and $R^{3B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{3A}$ and $R^{3B}$ substituents bonded to the same nitrogen atom are joined is substituted, it is substituted with at least one substituent group. In embodiments, when the substituted ring formed when $R^{3A}$ and $R^{3B}$ substituents bonded to the same nitrogen atom are joined is substituted, it is substituted with at least one size-limited substituent group. In embodiments, when the substituted ring formed when $R^{3A}$ and $R^{3B}$ substituents bonded to the same nitrogen atom are joined is substituted, it is substituted with at least one lower substituent group.

In embodiments, a substituted $R^{3C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group;

wherein if the substituted $R^{3C}$ is substituted with a plurality of groups selected from substituent groups, size-limited substituent groups, and lower substituent groups; each substituent group, size-limited substituent group, and/or lower substituent group may optionally be different. In embodiments, when $R^{3C}$ is substituted, it is substituted with at least one substituent group. In embodiments, when $R^{3C}$ is substituted, it is substituted with at least one size-limited substituent group. In embodiments, when $R^{3C}$ is substituted, it is substituted with at least one lower substituent group.

In embodiments, a substituted $R^{3D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3D}$ is substituted with a plurality of groups selected from substituent groups, size-limited substituent groups, and lower substituent groups; each substituent group, size-limited substituent group, and/or lower substituent group may optionally be different. In embodiments, when $R^{3D}$ is substituted, it is substituted with at least one substituent group. In embodiments, when $R^{3D}$ is substituted, it is substituted with at least one size-limited substituent group. In embodiments, when $R^{3D}$ is substituted, it is substituted with at least one lower substituent group.

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, a substituted ring formed when two $R^4$ substituents are joined (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed when two $R^4$ substituents are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two $R^4$ substituents are joined is substituted, it is substituted with at least one substituent group. In embodiments, when the substituted ring formed when two $R^4$ substituents are joined is substituted, it is substituted with at least one size-limited substituent group. In embodiments, when the substituted ring formed when two $R^4$ substituents are joined is substituted, it is substituted with at least one lower substituent group.

In embodiments, a substituted $R^{4A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4A}$ is substituted with a plurality of groups selected from substituent groups, size-limited substituent groups, and lower substituent groups; each substituent group, size-limited substituent group, and/or lower substituent group may optionally be different. In embodiments, when $R^{4A}$ is substituted, it is substituted with at least one substituent group. In embodiments, when $R^{4A}$ is substituted, it is substituted with at least one size-limited substituent group. In embodiments, when $R^{4A}$ is substituted, it is substituted with at least one lower substituent group.

In embodiments, a substituted $R^{4B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4B}$ is substituted with a plurality of groups selected from substituent groups, size-limited substituent groups, and lower substituent groups; each substituent group, size-limited substituent group, and/or lower substituent group may optionally be different. In embodiments, when $R^{4B}$ is substituted, it is substituted with at least one substituent group. In embodiments, when $R^{4B}$ is substituted, it is substituted with at least one size-limited substituent group. In embodiments, when $R^{4B}$ is substituted, it is substituted with at least one lower substituent group.

In embodiments, a substituted ring formed when $R^{4A}$ and $R^{4B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{4A}$ and $R^{4B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{4A}$ and $R^{4B}$ substituents bonded to the same nitrogen atom are joined is substituted, it is substituted with at least one substituent group. In embodiments, when the substituted ring formed when $R^{4A}$ and $R^{4B}$ substituents bonded to the same nitrogen atom are joined is substituted, it is substituted with at least one size-limited substituent group. In embodiments, when the substituted ring formed when $R^{4A}$ and $R^{4B}$ substituents bonded to the same nitrogen atom are joined is substituted, it is substituted with at least one lower substituent group.

In embodiments, a substituted $R^{4C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4C}$ is substituted with a plurality of groups selected from substituent groups, size-limited substituent groups, and lower substituent groups; each substituent group, size-limited substituent group, and/or lower substituent group may optionally be different. In embodiments, when $R^{4C}$ is substituted, it is substituted with at least one substituent group. In embodiments, when $R^{4C}$ is substituted, it is substituted with at least one size-limited substituent group. In embodiments, when $R^{4C}$ is substituted, it is substituted with at least one lower substituent group.

In embodiments, a substituted $R^{4D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4D}$ is substituted with a plurality of groups selected from substituent groups, size-limited substituent groups, and lower substituent groups; each substituent group, size-limited substituent group, and/or lower substituent group may optionally be different. In embodiments, when $R^{4D}$ is substituted, it is substituted with at least one substituent group. In embodiments, when $R^{4D}$ is substituted, it is substituted with at least one size-limited substituent group. In embodiments, when $R^{4D}$ is substituted, it is substituted with at least one lower substituent group.

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, a substituted $R^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, a substituted ring formed when two $R^{10}$ substituents bonded to adjacent atoms are joined (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed when two $R^{10}$ substituents bonded to adjacent atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two $R^{10}$ substituents bonded to adjacent atom are joined is substituted, it is substituted with at least one substituent group. In embodiments, when the substituted ring formed when two $R^{10}$ substituents bonded to adjacent atom are joined is substituted, it is substituted with at least one size-limited substituent group. In embodiments, when the substituted ring formed when two $R^{10}$ substituents bonded to adjacent atom are joined is substituted, it is substituted with at least one lower substituent group.

In embodiments, when $R^1$ is substituted, $R^1$ is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by R1.2 as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when $R^{1A}$ is substituted, $R^{1A}$ is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A}$, $R^{1A.1}$, $R^{A.2}$, and $R^{1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1A}$, $R^{1A.1}$, $R^{1A.2}$, and $R^{1A.3}$, respectively.

In embodiments, when $R^{1B}$ is substituted, $R^{1B}$ is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B}$, $R^{1B.1}$, $R^{1B.2}$, and $R^{1B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1B}$, $R^{1B.1}$, $R^{1B.2}$, and $R^{1B.3}$, respectively.

In embodiments, when $R^{1A}$ and $R^{1B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A.1}$, $R^{1A.2}$, and $R^{1A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{1A.1}$, $R^{1A.2}$, and $R^{1A.3}$ respectively.

In embodiments, when $R^{1A}$ and $R^{1B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B.1}$, $R^{1B.2}$, and $R^{1B.3}$ have values corresponding to the values of $R^{WW.1}$, $R^{WW.2}$ and $R^{WW.3}$, respectively, as explained in the definitions section above in the description of "first substituent group(s)", wherein $R^{WW.1}$, $R^{WW.2}$, and $R^{WW.3}$ correspond to $R^{1B.1}$, $R^{1B.2}$, and $R^{1B.3}$ respectively.

In embodiments, when $R^2$ is substituted, $R^2$ is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by R2.2 as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when two $R^2$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$ and $R^{2.3}$, respectively.

In embodiments, when $R^{2A}$ is substituted, $R^{2A}$ is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$, respectively.

In embodiments, when $R^{2B}$, is substituted, $R^{2B}$ is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B}$, $R^{2B.1}$, $R^{2B.2}$, and $R^{2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2A}$ and $R^{2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A.1}$, $R^{2A.2}$, and $R^{2A.3}$ have values corresponding to the values of $R^{WW.1}$, $R^{WW2}$, and $R^{WW.3}$, respectively, as explained in the definitions section above in the description of "first substituent group(s)", wherein $R^{WW.1}$, $R^{WW.2}$, and $R^{WW.3}$ correspond to $R^{2A.1}$, $R^{2A.2}$, and $R^{2A.3}$ respectively.

In embodiments, when $R^{2A}$ and $R^{2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B.1}$, $R^{2B.2}$, and $R^{2B.3}$ have values corresponding to the values of $R^{WW.1}$, $R^{WW2}$, and $R^{WW.3}$, respectively, as explained in the definitions section above in the description of "first substituent group(s)", wherein $R^{WW.1}$, $R^{WW.2}$, and $R^{WW.3}$ correspond to $R^{2B.1}$, $R^{2B.2}$, and $R^{2B.3}$, respectively.

In embodiments, when $R^{2C}$ is substituted, $R^{2C}$ is substituted with one or more first substituent groups denoted by $R^{2C.1}$ as explained in the definitions section above in the description of "first substituent group(s)". In embodiments, when an $R^{2C.1}$ substituent group is substituted, the $R^{2C.1}$ substituent group is substituted with one or more second substituent groups denoted by $R^{2C.2}$ as explained in the definitions section above in the description of "first substituent group(s)". In embodiments, when an $R^{2C.2}$ substituent group is substituted, the $R^{2C.2}$ substituent group is substituted with one or more third substituent groups denoted by $R^{2C.3}$ as explained in the definitions section above in the description of "first substituent group(s)". In the above embodiments, $R^{2C}$, $R^{2C.1}$, $R^{2C.2}$, and $R^{2C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2C}$, $R^{2C.1}$, $R^{2C.2}$, and $R^{2C.3}$, respectively.

In embodiments, when $R^{2D}$ is substituted, $R^{2D}$ is substituted with one or more first substituent groups denoted by $R^{2D.1}$ as explained in the definitions section above in the description of "first substituent group(s)". In embodiments, when an $R^{2D.1}$ substituent group is substituted, the $R^{2D.1}$ substituent group is substituted with one or more second substituent groups denoted by $R^{2D.2}$ as explained in the definitions section above in the description of "first substituent group(s)". In embodiments, when an $R^{2D.2}$ substituent group is substituted, the $R^{2D.2}$ substituent group is substituted with one or more third substituent groups denoted by $R^{2D.3}$ as explained in the definitions section above in the description of "first substituent group(s)". In the above embodiments, $R^{2D}$, $R^{2D.1}$, $R^{2D.2}$, and $R^{2D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2D}$, $R^{2D.1}$, $R^{2D.2}$, and $R^{2D.3}$, respectively.

In embodiments, when $R^3$ is substituted, $R^3$ is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.2}$ substituent group is substituted, the $R^{3.2}$ substituent group is substituted with one or more third substituent groups denoted by $R^{3.3}$ as explained in the definitions section above in the description of "first substituent group(s)". In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^3$, $R^{3.1}$, $R^{3.2}$ and $R^{3.3}$, respectively.

In embodiments, when two $R^3$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.2}$ substituent group is substituted, the $R^{3.2}$ substituent group is substituted with one or more third substituent groups denoted by $R^{3.3}$ as explained in the definitions section above in the description of "first substituent group(s)". In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^3$, $R^{3.1}$, $R^{3.2}$ and $R^{3.3}$, respectively.

In embodiments, when $R^{3A}$ is substituted, $R^{3A}$ is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A}$, $R^{3A.1}$, $R^{3A.2}$, and $R^{3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3A}$, $R^{3A.1}$, $R^{3A.2}$ and $R^{3A.3}$, respectively.

In embodiments, when $R^{3B}$ is substituted, $R^{3B}$ is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ as explained in the definitions section above in the description of "first substituent group(s)". In the above embodiments, $R^{3B}$, $R^{3B.1}$, $R^{3B.2}$, and $R^{3B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3B}$, $R^{3B.1}$, $R^{3B.2}$, and $R^{3B.3}$, respectively.

In embodiments, when $R^{3A}$ and $R^{3B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A.1}$, $R^{3A.2}$, and $R^{3A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{3A.1}$, $R^{3A.2}$, and $R^{3A.3}$ respectively.

In embodiments, when $R^{3A}$ and $R^{3B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ as explained in the definitions section above in the description of "first substituent group(s)". In the above embodiments, $R^{3B.1}$, $R^{3B.2}$, and $R^{3B.3}$ have values corresponding to the values of $R^{WW.1}$, $R^{WW.2}$ and $R^{WW.3}$, respectively, as explained in the definitions section above in the description of "first substituent group(s)", wherein $R^{WW.1}$, $R^{WW.2}$, and $R^{WW.3}$ correspond to $R^{3B.1}$, $R^{3B.2}$, and $R^{3B.3}$ respectively.

In embodiments, when $R^{3C}$ is substituted, $R^{3C}$ is substituted with one or more first substituent groups denoted by $R^{3C.1}$ as explained in the definitions section above in the description of "first substituent group(s)". In embodiments, when an $R^{3C.1}$ substituent group is substituted, the $R^{3C.1}$ substituent group is substituted with one or more second substituent groups denoted by $R^{3C.2}$ as explained in the definitions section above in the description of "first substituent group(s)". In embodiments, when an $R^{3C.2}$ substituent group is substituted, the $R^{3C.2}$ substituent group is substituted with one or more third substituent groups denoted by $R^{3C.3}$ as explained in the definitions section above in the description of "first substituent group(s)". In the above embodiments, $R^{3C}$, $R^{3C.1}$, $R^{3C.2}$, and $R^{3C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3C}$, $R^{3C.1}$, $R^{3C.2}$, and $R^{3C.3}$, respectively.

In embodiments, when $R^{3D}$ is substituted, $R^{3D}$ is substituted with one or more first substituent groups denoted by $R^{3D.1}$ as explained in the definitions section above in the description of "first substituent group(s)". In embodiments, when an $R^{3D.1}$ substituent group is substituted, the $R^{3D.1}$ substituent group is substituted with one or more second substituent groups denoted by $R^{3D.2}$ as explained in the definitions section above in the description of "first substituent group(s)". In embodiments, when an $R^{3D.2}$ substituent group is substituted, the $R^{3D.2}$ substituent group is substituted with one or more third substituent groups denoted by $R^{3D.3}$ as explained in the definitions section above in the description of "first substituent group(s)". In the above embodiments, $R^{3D}$, $R^{3D.1}$, $R^{3D.2}$, and $R^{3D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3D}$, $R^{3D.1}$, $R^{3D.2}$, and $R^{3D.3}$, respectively.

In embodiments, when $R^4$ is substituted, $R^4$ is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$ and $R^{4.3}$, respectively.

In embodiments, when two $R^4$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$ and $R^{4.3}$, respectively.

In embodiments, when $R^{4A}$ is substituted, $R^{4A}$ is substituted with one or more first substituent groups denoted by $R^{4A.1}$ as explained in the definitions section above in the description of "first substituent group(s)". In embodiments, when an $R^{4A.1}$ substituent group is substituted, the $R^{4A.1}$ substituent group is substituted with one or more second substituent groups denoted by $R^{4A.2}$ as explained in the definitions section above in the description of "first substituent group(s)". In embodiments, when an $R^{4A.2}$ substituent group is substituted, the $R^{4A.2}$ substituent group is substituted with one or more third substituent groups denoted by $R^{4A.3}$ as explained in the definitions section above in the description of "first substituent group(s)". In the above embodiments, $R^{4A}$, $R^{4A.1}$, $R^{4A.2}$, and $R^{4A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4A}$, $R^{4A.1}$, $R^{4A.2}$, and $R^{4A.3}$, respectively.

In embodiments, when $R^{4B}$ is substituted, $R^{4B}$ is substituted with one or more first substituent groups denoted by $R^{4B.1}$ as explained in the definitions section above in the description of “first substituent group(s)”. In embodiments, when an $R^{4B.1}$ substituent group is substituted, the $R^{4B.1}$ substituent group is substituted with one or more second substituent groups denoted by $R^{4B.2}$ as explained in the definitions section above in the description of “first substituent group(s)”. In embodiments, when an $R^{4B.2}$ substituent group is substituted, the $R^{4B.2}$ substituent group is substituted with one or more third substituent groups denoted by $R^{4B.3}$ as explained in the definitions section above in the description of “first substituent group(s)”. In the above embodiments, $R^{4B}$, $R^{4B.1}$, $R^{4B.2}$, and $R^{4B.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{4B}$, $R^{4B.1}$, $R^{4B.2}$, and $R^{4B.3}$, respectively.

In embodiments, when $R^{4A}$ and $R^{4B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{4A.1}$ as explained in the definitions section above in the description of “first substituent group(s)”. In embodiments, when an $R^{4A.1}$ substituent group is substituted, the $R^{4A.1}$ substituent group is substituted with one or more second substituent groups denoted by $R^{4A.2}$ as explained in the definitions section above in the description of “first substituent group(s)”. In embodiments, when an $R^{4A.2}$ substituent group is substituted, the $R^{4A.2}$ substituent group is substituted with one or more third substituent groups denoted by $R^{4A.3}$ as explained in the definitions section above in the description of “first substituent group(s)”. In the above embodiments, $R^{4A.1}$, $R^{4A.2}$, and $R^{4A.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{4A.1}$, $R^{4A.2}$, and $R^{4A.3}$ respectively.

In embodiments, when $R^{4A}$ and $R^{4B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{4B.1}$ as explained in the definitions section above in the description of “first substituent group(s)”. In embodiments, when an $R^{4B.1}$ substituent group is substituted, the $R^{4B.1}$ substituent group is substituted with one or more second substituent groups denoted by $R^{4B.2}$ as explained in the definitions section above in the description of “first substituent group(s)”. In embodiments, when an $R^{4B.2}$ substituent group is substituted, the $R^{4B.2}$ substituent group is substituted with one or more third substituent groups denoted by $R^{4B.3}$ as explained in the definitions section above in the description of “first substituent group(s)”. In the above embodiments, $R^{4B.1}$, $R^{4B.2}$, and $R^{4B.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{4B.1}$, $R^{4B.2}$, and $R^{4B.3}$ respectively.

In embodiments, when $R^{4C}$ is substituted, $R^{4C}$ is substituted with one or more first substituent groups denoted by $R^{4C.1}$ as explained in the definitions section above in the description of “first substituent group(s)”. In embodiments, when an $R^{4C.1}$ substituent group is substituted, the $R^{4C.1}$ substituent group is substituted with one or more second substituent groups denoted by $R^{4C.2}$ as explained in the definitions section above in the description of “first substituent group(s)”. In embodiments, when an $R^{4C.2}$ substituent group is substituted, the $R^{4C.2}$ substituent group is substituted with one or more third substituent groups denoted by $R^{4C.3}$ as explained in the definitions section above in the description of “first substituent group(s)”. In the above embodiments, $R^{4C}$, $R^{4C.1}$, $R^{4C.2}$, and $R^{4C.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{4C}$, $R^{4C.1}$, $R^{4C.2}$, and $R^{4C.3}$, respectively.

In embodiments, when $R^{4D}$ is substituted, $R^{4D}$ is substituted with one or more first substituent groups denoted by $R^{4D.1}$ as explained in the definitions section above in the description of “first substituent group(s)”. In embodiments, when an $R^{4D.1}$ substituent group is substituted, the $R^{4D.1}$ substituent group is substituted with one or more second substituent groups denoted by $R^{4D.2}$ as explained in the definitions section above in the description of “first substituent group(s)”. In embodiments, when an $R^{4D.2}$ substituent group is substituted, the $R^{4D.2}$ substituent group is substituted with one or more third substituent groups denoted by $R^{4D.3}$ as explained in the definitions section above in the description of “first substituent group(s)”. In the above embodiments, $R^{4D}$, $R^{4D.1}$, $R^{4D.2}$, and $R^{4D.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{4D}$, $R^{4D.1}$, $R^{4D.2}$, and $R^{4D.3}$, respectively.

In embodiments, when $R^5$ is substituted, $R^5$ is substituted with one or more first substituent groups denoted by $R^{5.1}$ as explained in the definitions section above in the description of “first substituent group(s)”. In embodiments, when an $R^{5.1}$ substituent group is substituted, the $R^{5.1}$ substituent group is substituted with one or more second substituent groups denoted by $R^{5.2}$ as explained in the definitions section above in the description of “first substituent group(s)”. In embodiments, when an $R^{5.2}$ substituent group is substituted, the $R^{5.2}$ substituent group is substituted with one or more third substituent groups denoted by $R^{5.3}$ as explained in the definitions section above in the description of “first substituent group(s)”. In the above embodiments, $R^5$, $R^{5.1}$, $R^{5.2}$, and $R^{5.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^5$, $R^{5.1}$, $R^{5.2}$ and $R^{5.3}$, respectively.

In embodiments, when $R^{10}$ is substituted, $R^{10}$ is substituted with one or more first substituent groups denoted by $R^{10.1}$ as explained in the definitions section above in the description of “first substituent group(s)”. In embodiments, when an $R^{10.1}$ substituent group is substituted, the $R^{10.1}$ substituent group is substituted with one or more second substituent groups denoted by $R^{10.2}$ as explained in the definitions section above in the description of “first substituent group(s)”. In embodiments, when an $R^{10.2}$ substituent group is substituted, the $R^{10.2}$ substituent group is substituted with one or more third substituent groups denoted by $R^{10.3}$ as explained in the definitions section above in the description of “first substituent group(s)”. In the above embodiments, $R^{10}$, $R^{10.1}$, $R^{10.2}$, and $R^{10.3}$ have values corresponding to the values of $R^{WW}$, $R^{WW.1}$, $R^{WW.2}$, and $R^{WW.3}$, Respectively, as Explained in the Definitions Section Above in the description of “first substituent group(s)”, wherein $R^{WW}$, $R^{WW.1}$, $R^{WW.2}$, and $R^{WW.3}$ correspond to $R^{10}$, $R^{10.1}$, $R^{10.2}$, and $R^{10.3}$, respectively.

In embodiments, when two $R^{10}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{10.1}$ as explained in the definitions section above in the description of "first substituent group(s)". In embodiments, when an $R^{10.1}$ substituent group is substituted, the $R^{10.1}$ substituent group is substituted with one or more second substituent groups denoted by $R^{10.2}$ as explained in the definitions section above in the description of "first substituent group(s)". In embodiments, when an $R^{10.2}$ substituent group is substituted, the $R^{10.2}$ substituent group is substituted with one or more third substituent groups denoted by $R^{10.3}$ as explained in the definitions section above in the description of "first substituent group(s)". In the above embodiments, $R^{10}$, $R^{10.1}$, $R^{10.2}$, and $R^{10.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10}$, $R^{10.1}$, $R^{10.2}$, and $R^{10.3}$, respectively.

In embodiments, the compound has the formula

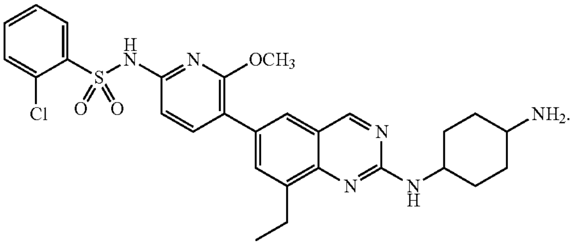 [SMILES: CCc1cc(-c2ccc(NS(=O)(=O)c3ccccc3Cl)nc2OC)cc2cnc(NC3CCC(N)CC3)nc12]

In embodiments, the compound has the formula

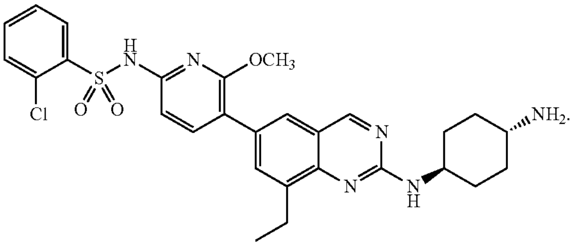 [SMILES: CCc1cc(-c2ccc(NS(=O)(=O)c3ccccc3Cl)nc2OC)cc2cnc(N[C@H]3CC[C@H](N)CC3)nc12]

In embodiments, the compound has the formula

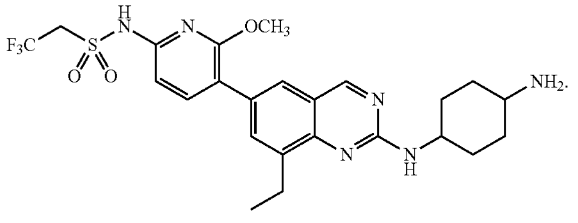 [SMILES: CCc1cc(-c2ccc(NS(=O)(=O)CC(F)(F)F)nc2OC)cc2cnc(NC3CCC(N)CC3)nc12]

In embodiments, the compound has the formula

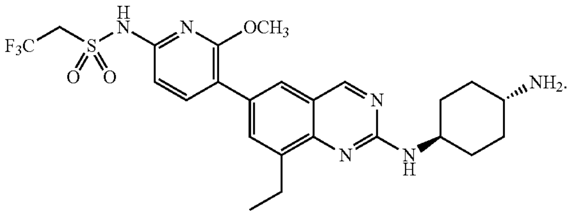 [SMILES: CCc1cc(-c2ccc(NS(=O)(=O)CC(F)(F)F)nc2OC)cc2cnc(N[C@H]3CC[C@H](N)CC3)nc12]

In embodiments, the compound has the formula

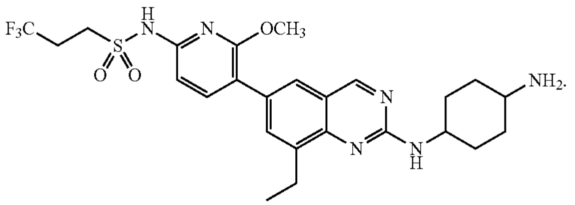 [SMILES: CCc1cc(-c2ccc(NS(=O)(=O)CCC(F)(F)F)nc2OC)cc2cnc(NC3CCC(N)CC3)nc12]

In embodiments, the compound has the formula

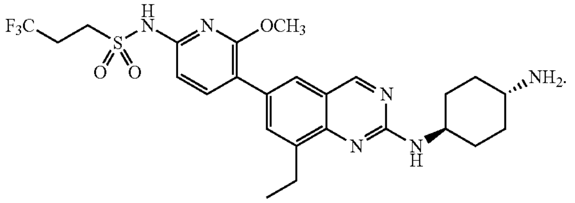 [SMILES: CCc1cc(-c2ccc(NS(=O)(=O)CCC(F)(F)F)nc2OC)cc2cnc(N[C@H]3CC[C@H](N)CC3)nc12]

In embodiments, the compound has the formula

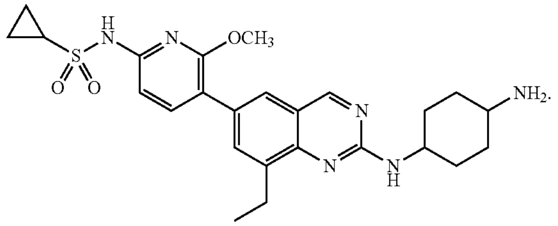 [SMILES: CCc1cc(-c2ccc(NS(=O)(=O)C3CC3)nc2OC)cc2cnc(NC3CCC(N)CC3)nc12]

In embodiments, the compound has the formula

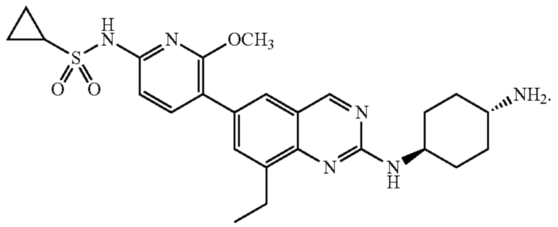 [SMILES: CCc1cc(-c2ccc(NS(=O)(=O)C3CC3)nc2OC)cc2cnc(N[C@H]3CC[C@H](N)CC3)nc12]

In embodiments, the compound is a compound described herein. In embodiments, the compound, or salt (e.g., pharmaceutically acceptable salt) thereof, is the compound. In embodiments, the compound, or a salt (e.g., pharmaceutically acceptable salt) thereof, is the salt (e.g., pharmaceuti cally acceptable salt) of the compound. In embodiments, the compound, or a salt (e.g., pharmaceutically acceptable salt) thereof, is the pharmaceutically acceptable salt of the compound. In embodiments, at least one atom of the compound is an isotope other than the most common isotope of that atom (e.g., wherein a compound described herein includes a hydrogen at a specific position, that hydrogen is a deuterium, wherein a compound described herein includes a hydrogen at a specific position, that hydrogen is a tritium, wherein a compound described herein includes a carbon at a specific position, that carbon is a carbon-14). In embodiments, an atom of the compound is an isotope other than the most common isotope of that atom (e.g., wherein a compound described herein includes a hydrogen at a specific position, that hydrogen is a deuterium, wherein a compound described herein includes a hydrogen at a specific position, that hydrogen is a tritium, wherein a compound described herein includes a carbon at a specific position, that carbon is a carbon-14). In embodiments, wherein a compound described herein includes an isotope at a particular atom position that is not the most common isotope of that atom, the particular atom is not the most common isotope (e.g., a deuterium instead of a protium) in at least 50% of the compounds (e.g., at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, wherein a compound described herein includes an isotope at a particular atom position that is not the most common isotope of that atom, the particular atom is not the most common isotope (e.g., a deuterium instead of a protium) in at least 50% of the compounds (e.g., about 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, wherein a compound described herein includes an isotope at a particular atom position that is not the most common isotope of that atom, the particular atom is not the most common isotope (e.g., a deuterium instead of a protium) in at least 50% of the compounds (e.g., 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

III. Pharmaceutical Compositions

In an aspect is provided a pharmaceutical composition including a compound described herein, or a salt (e.g., pharmaceutically acceptable salt) thereof, and a pharmaceutically acceptable excipient. In embodiments, the compound as described herein is included in a therapeutically effective amount. In embodiments, the compound as described herein is included in an effective amount.

In embodiments of the pharmaceutical compositions, the compound, or salt (e.g., pharmaceutically acceptable salt) thereof, is included in a therapeutically effective amount. In embodiments of the pharmaceutical compositions, the compound, or salt (e.g., pharmaceutically acceptable salt) thereof, is a compound. In embodiments of the pharmaceutical compositions, the compound, or salt (e.g., pharmaceutically acceptable salt) thereof, is a salt (e.g., pharmaceutically acceptable salt) of the compound. In embodiments of the pharmaceutical compositions, the compound, or salt (e.g., pharmaceutically acceptable salt) thereof, is a pharmaceutically acceptable salt of the compound.

In embodiments of the pharmaceutical compositions, the pharmaceutical composition includes a second agent (e.g., therapeutic agent). In embodiments of the pharmaceutical compositions, the pharmaceutical composition includes a second agent (e.g., therapeutic agent) in a therapeutically effective amount. In embodiments of the pharmaceutical compositions, the second agent is an agent for treating cancer. In embodiments of the pharmaceutical compositions, the second agent is an agent for treating a cell degenerative disease. In embodiments of the pharmaceutical compositions, the second agent is an agent for treating a neurodegenerative disease. In embodiments, the administering does not include administration of any active agent other than the recited active agent (e.g., a compound described herein). In embodiments, the second agent is included in an effective amount.

IV. Methods of Use

In an aspect is provided a method of decreasing the level of Ire1α protein activity in a subject, the method including administering a compound described herein, or a salt (e.g., pharmaceutically acceptable salt) thereof, to the subject. In embodiments, the compound is administered in a therapeutically effective amount. In embodiments, the compound as described herein is included in an effective amount. In embodiments, the activity is kinase activity. In embodiments, the activity is RNase activity.

In an aspect is provided a method of treating a cell degenerative disease in a subject in need thereof, the method including administering to the subject in need thereof an effective amount of a compound described herein.

In embodiments, the cell degenerative disease is a neurodegenerative disease.

In embodiments, the cell degenerative disease is Type 1 Diabetes Melllitus, Type 2 Diabetes Mellitus, Mature Onset diabetes of the Young (MODY), Mutant INS-gene-induced Diabetes of the young (MIDY), Immune Checkpoint-induced Diabetes Mellitus, Wolfram's Syndrome, Wolcott-Rallison Syndrome, Idiopathic Pulmonary fibrosis (IPF), Familial Pulmonary Fibrosis (FPF), Asthma, Alzheimer's disease, Amyotrophic lateral sclerosis, Charcot-Marie-Tooth disease, Chronic traumatic encephalopathy, Cystic fibrosis, cytochrome c oxidase deficiency, degenerative Leigh syndrome, Ehlers-Danlos syndrome, Fibrodysplasia ossificans progressiva, Friedreich's ataxia, Frontotemporal dementia, cardiovascular diseases, coronary artery disease, aortic stenosis, Huntington's disease, Infantile neuroaxonal dystrophy, Keratoconus, Keratoglobus, Leukodystrophies, Wet Macular degeneration, Dry Macular degeneration, Marfan's syndrome, Some mitochondrial myopathies, Mitochondrial DNA depletion syndrome, Multiple sclerosis, Multiple system atrophy, Muscular dystrophies, Neuronal ceroid lipofuscinosis, Niemann-Pick diseases, Osteoarthritis, Osteoporosis, Parkinson's disease, Pulmonary arterial hypertension, prion disease, Creutzfeldt-Jakob disease, fatal familial insomnia, Progressive supranuclear palsy, Retinitis pigmentosa, Rheumatoid arthritis, Sandhoff Disease, Scleroderma, Spinal muscular atrophy, Subacute sclerosing panencephalitis, Tay-Sachs disease, or Vascular dementia.

In embodiments, the method further includes co-administering an agent for treating a cell degenerative disease to the subject in need.

In an aspect is provided a method of inhibiting cancer growth in a subject in need thereof, the method including administering to the subject in need thereof an effective amount of a compound described herein, or a salt (e.g., pharmaceutically acceptable salt) thereof. In embodiments, the compound is administered in a therapeutically effective amount. In embodiments, the compound as described herein is included in an effective amount.

In an aspect is provided a method of treating a cancer in a subject in need thereof, the method including administering to the subject in need thereof an effective amount of a compound described herein, or a salt (e.g., pharmaceutically acceptable salt) thereof. In embodiments, the compound is administered in a therapeutically effective amount. In embodiments, the compound as described herein is included in an effective amount.

In an aspect is provided a method of treating a proliferative disorder (e.g., cancer) in a subject in need thereof, the method including administering to the subject in need thereof an effective amount of a compound described herein, or a salt (e.g., pharmaceutically acceptable salt) thereof. In embodiments, the compound is administered in a therapeutically effective amount. In embodiments, the compound as described herein is included in an effective amount.

In embodiments, the cancer is a solid cancer or a hematologic cancer. In embodiments, the cancer is an ovarian cancer, a colon carcinoma, a bladder cancer, hepatocellular carcinoma, a breast cancer, a pancreatic adenocarcinoma, a prostate cancer, a gliobastoma, or a lung cancer. In embodiments, the breast cancer is triple negative breast cancer (TNBC). In embodiments, the cancer is a leukemia, lymphoma, or multiple myeloma. In embodiments, the compound is administered to the subject intravenously or orally. In embodiments, the cancer is a cancer of the breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, or villous colon adenoma. In some embodiments, the cancer is squamous cell cancer, small-cell lung cancer, non-small cell lung cancer ("NSCLC"), adenocarcinoma of the lung and squamous carcinoma of the lung, cancer of the peritoneum, hepatocellular cancer, stomach cancer, gastrointestinal cancer, esophageal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, or head and neck cancer. In some embodiments, the cancer is a hematological malignancy selected from the group consisting of lymphomas, lymphocytic leukemia, myeloma, acute and chronic myelogenous leukemia, myelodysplastic syndrome and myeloproliferative disease. In embodiments, the cancer is selected from the group consisting of squamous cell cancer, small-cell lung cancer, non-small cell lung cancer ("NSCLC"), adenocarcinoma of the lung and squamous carcinoma of the lung, cancer of the peritoneum, hepatocellular cancer, stomach cancer, gastrointestinal cancer, esophageal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, and head and neck cancer. In embodiments, the cancer is a hematological malignancy selected from the group consisting of lymphomas, lymphocytic leukemia, myeloma, acute and chronic myelogenous leukemia, myelodysplastic syndrome and myeloproliferative disease. In embodiments, the cancer is multiple myeloma. In embodiments, the cancer is a triple-negative breast cancer ("TNBC").

In embodiments, a compound disclosed herein is used to treat or ameliorate a disease associated with altered IRE1α pathway signaling when administered to a subject in need thereof. In embodiments, a compound disclosed herein is used to treat or ameliorate the effects of a disease associated with altered IRE1α pathway signaling when administered to a subject in need thereof. In embodiments, the disease associated with altered IRE1α signaling is cancer. In embodiments, a compound disclosed herein is used to treat or ameliorate a cancer when administered to a subject in need thereof. In embodiments, the cancer includes tumors, solid, or hematologic cancers. In embodiments, a compound disclosed herein is used to treat or ameliorate a cell proliferative disorder when administered to a subject in need thereof. In embodiments, the cell proliferative disorder is a cancer. In embodiments, the solid cancer is ovarian cancer, lung cancer, breast cancer, bladder cancer, or triple negative breast cancer (TNBC). In embodiments, the hematological cancer is a leukemia, lymphoma, or multiple myeloma.

In embodiments, a compound disclosed herein is used to reinforce anti-tumor mechanisms through stimulation of the innate (for example dendritic cells) and adaptive immune (T- and/or B-cells) systems in recognition and targeting of the tumor cells. In embodiments, an anti-tumor mechanism includes direct inhibition of tumor growth. In embodiments, an anti-tumor mechanism includes induction of anti-tumor immunity. In embodiments, the compound preserves the differentiated state and/or health of immune cells (e.g., of the innate immune system or adaptive immune system). In embodiments, the compound increases the production of antibodies by a cell compared to the production of the cell in the absence of the compound (e.g., in a subject). In embodiments, anti-tumor mechanisms include direct inhibition of tumor growth and simultaneous induction of anti-tumor immunity—in these cases, PD-1 or PD-L1 inhibitors may be used in combination with IRE1α inhibitors. In embodiments, a compound disclosed herein can prevent lipid accumulation in myeloid cells exposed to ovarian cancer-derived ascites supernatants. In embodiments, a compound disclosed herein can block myeloid cell immunosuppression mediated by tumor-associated factors. In embodiments, a compound disclosed herein can be employed as a therapeutic compound that enhances dendritic cell and T cell anti-tumor activity in a mammal. In embodiments, the compounds disclosed herein can be used to treat murine and/or human ovarian cancers. In embodiments, a compound described herein reinforces anti-cancer mechanisms through stimulation of the innate (for example dendritic cells) and adaptive immune (T- and/or B-cells) systems in recognition and targeting of the cancer cells, wherein the cancer is a cancer described herein (e.g., solid cancer, hematologic cancer, ovarian cancer, a colon carcinoma, a bladder cancer, hepatocellular carcinoma, a breast cancer, a pancreatic adenocarcinoma, a prostate cancer, a glioblastoma, a lung cancer, triple negative breast cancer (TNBC), leukemia, lymphoma, multiple myeloma, breast cancer, ovarian cancer, cervix cancer, prostate cancer, testis cancer, genitourinary tract cancer, esophagus cancer, larynx cancer; glioblastoma, neuroblastoma, stomach cancer, skin cancer, keratoacanthoma cancer, lung cancer, epidermoid carcinoma, large cell carcinoma, non-small cell lung carcinoma (NSCLC), small cell carcinoma, lung adenocarcinoma, bone cancer, colon cancer, adenoma, pancreas cancer, adenocarcinoma, thyroid cancer, follicular carcinoma, undifferentiated carcinoma, papillary carcinoma, seminoma, melanoma, sarcoma, bladder carcinoma, liver carcinoma and biliary passages, kidney carcinoma, pancreatic cancer, myeloid disorders, lymphoma, hairy cells cancer, buccal cavity cancer, naso-pharyngeal cancer, pharynx cancer, lip cancer, tongue cancer, mouth cancer, small intestine cancer, colon-rectum cancer, large intestine cancer, rectum cancer, brain and central nervous system cancer, Hodgkin's, leukemia, bronchus cancer, thyroid cancer, liver and intrahepatic bile duct cancer, hepatocellular cancer, gastric cancer, glioma/glioblastoma, endometrial cancer, melanoma, kidney and renal pelvis cancer, urinary bladder cancer, uterine corpus cancer, uterine cervix cancer, multiple myeloma, acute myelogenous leukemia, chronic myelogenous leukemia, lymphocytic leukemia, chronic lymphoid leukemia (CLL), myeloid leukemia, oral cavity and pharynx cancer, non-Hodgkin lymphoma, melanoma, villous colon adenoma, squamous cell cancer, small-cell lung cancer, non-small cell lung cancer ("NSCLC"), adenocarcinoma of the lung, squamous carcinoma of the lung, cancer of the peritoneum, hepatocellular cancer, stomach cancer, gastrointestinal cancer, esophageal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, lymphomas, lymphocytic leukemia, myeloma, acute and chronic myelogenous leukemia, myelodysplastic syndrome, myeloproliferative disease, squamous cell cancer, small-cell lung cancer, non-small cell lung cancer ("NSCLC"), adenocarcinoma of the lung, squamous carcinoma of the lung, cancer of the peritoneum, hepatocellular cancer, stomach cancer, gastrointestinal cancer, esophageal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, hematological malignancy, lymphomas, lymphocytic leukemia, myeloma, acute and chronic myelogenous leukemia, myelodysplastic syndrome, myeloproliferative disease, multiple myeloma, or triple-negative breast cancer ("TNBC")).

In an aspect is provided a method of treating a disease associated with aberrant IRE1α activity in a subject in need thereof, the method including administering to the subject in need thereof an effective amount of a compound described herein, or a salt (e.g., pharmaceutically acceptable salt) thereof. In embodiments, the compound is administered in a therapeutically effective amount. In embodiments, the compound as described herein is included in an effective amount.

In embodiments, the method further includes co-administering an anti-cancer agent to the subject in need. In embodiments, the anti-cancer agent is administered in a therapeutically effective amount. In embodiments, the anti-cancer agent is a checkpoint inhibitor.

In an aspect is provided a method of treating a disease associated with IRE1α activity in a subject in need thereof, the method including administering to the subject in need thereof an effective amount of a compound described herein, or a salt (e.g., pharmaceutically acceptable salt) thereof. In embodiments, the compound is administered in a therapeutically effective amount. In embodiments, the compound as described herein is included in an effective amount. In embodiments, the disease is a neurodegenerative disease (ND) (e.g., amyotrophic lateral sclerosis (ALS), Parkinson's disease, Alzheimer's disease, prion disorders (e.g., BSE), frontotemporal dementia), posterior eye indication (e.g., retinal degeneration (e.g., a subset of ND): retinitis pigmentosa (ADRP), Stargardt's disease, wet AMD (choroidal neovascularization-CNV), dry AMD), Anterior eye indication (e.g., glaucoma, Fuch's dystrophy), Diabetes mellitus (e.g, typel (autoimmune), type 2 (e.g., obesity-induced/insulin-resistant), monogenic (e.g., MODY syndromes, for example pro-insulin mutations), recessive genetic disorders in which diabetes mellitus is a prominent component (e.g, Wolcott Rallisson syndrome (e.g., associated with Perk genetic deficiency), Wolfram syndrome (WFS1 or WFS2 deficiency)), fibrosing disorder or fibrosis (e.g., idiopathic pulmonary fibrosis (IPF), familial pulmonary fibrosis (FPF), scleroderma (systemic sclerosis), renal fibrosis, hepatic fibrosis), demyelinating disorder (e.g., multiple sclerosis (MS), Guillan-Barre, adrenoleukodystrophy, adrenomyeloneuropathy, optic neuritis, transverse myelitis), peripheral neuropathy (e.g., primary such as Charcot-Marie Tooth (CMT) or secondary from diabetes mellitus), dermatologic disease (e.g., psoriasis), rheumatologic disease, or autoimmune disease (e.g., rheumatoid arthritis, Grave's disease, Hashimoto's Disease, Addison's disease, Lupus, ankylosing spondylitis, sarcoidosis). In embodiments, the disease is Type 1 Diabetes Melllitus, Type 2 Diabetes Mellitus, Mature Onset diabetes of the Young (MODY), Mutant INS-gene-induced Diabetes of the young (MIDY), Immune Checkpoint-induced Diabetes Mellitus, Wolfram's Syndrome, Wolcott-Rallison Syndrome, Idiopathic Pulmonary fibrosis (IPF), Familial Pulmonary Fibrosis (FPF), Asthma, Alzheimer's disease, Amyotrophic lateral sclerosis, Charcot-Marie-Tooth disease, Chronic traumatic encephalopathy, Cystic fibrosis, cytochrome c oxidase deficiency, degenerative Leigh syndrome, Ehlers-Danlos syndrome, Fibrodysplasia ossificans progressiva, Friedreich's ataxia, Frontotemporal dementia, cardiovascular diseases, coronary artery disease, aortic stenosis, Huntington's disease, Infantile neuroaxonal dystrophy, Keratoconus, Keratoglobus, Leukodystrophies, Wet Macular degeneration, Dry Macular degeneration, Marfan's syndrome, Some mitochondrial myopathies, Mitochondrial DNA depletion syndrome, Multiple sclerosis, Multiple system atrophy, Muscular dystrophies, Neuronal ceroid lipofuscinosis, Niemann-Pick diseases, Osteoarthritis, Osteoporosis, Parkinson's disease, Pulmonary arterial hypertension, prion disease, Creutzfeldt-Jakob disease, fatal familial insomnia, Progressive supranuclear palsy, Retinitis pigmentosa, Rheumatoid arthritis, Sandhoff Disease, Scleroderma, Spinal muscular atrophy, Subacute sclerosing panencephalitis, Tay-Sachs disease, Vascular dementia. In an aspect is provided a method of treating a disease in a subject in need thereof, the method including administering to the subject in need thereof an effective amount of a compound described herein, or a salt (e.g., pharmaceutically acceptable salt) thereof, wherein the disease is a neurodegenerative disease (ND) (e.g., amyotrophic lateral sclerosis (ALS), Parkinson's disease, Alzheimer's disease, prion disorders (e.g., BSE), frontotemporal dementia), posterior eye indication (e.g., retinal degeneration (e.g. a subset of ND): retinitis pigmentosa (ADRP), Stargardt's disease, wet AMD (choroidal neovascularization-CNV), dry AMD), Anterior eye indication (e.g., glaucoma, Fuch's dystrophy), Diabetes mellitus (e.g, typel (autoimmune), type 2 (e.g., obesity-induced/insulin-resistant), monogenic (e.g. MODY syndromes, for example pro-insulin mutations), recessive genetic disorders in which diabetes mellitus is a prominent component (e.g, Wolcott Rallisson syndrome (e.g., associated with Perk genetic deficiency), Wolfram syndrome (WFS1 or WFS2 deficiency)), fibrosing disorder or fibrosis (e.g., idiopathic pulmonary fibrosis (IPF), familial pulmonary fibrosis (FPF), scleroderma (systemic sclerosis), renal fibrosis, hepatic fibrosis), demyelinating disorder (e.g., multiple sclerosis (MS), Guillan-Barre, adrenoleukodystrophy, adrenomyeloneuropathy, optic neuritis, transverse myelitis), peripheral neuropathy (e.g., primary such as Charcot-Marie Tooth (CMT) or secondary from diabetes mellitus), dermatologic disease (e.g., psoriasis), rheumatologic disease, or autoimmune disease (e.g., rheumatoid arthritis, Grave's disease, Hashimoto's Disease, Addison's disease, Lupus, ankylosing spondylitis, sarcoidosis). In embodiments, the compound is administered in a therapeutically effective amount. In embodiments, the compound as described herein is included in an effective amount. In embodiments, the disease is a neurodegenerative disease (ND) (e.g., amyotrophic lateral sclerosis (ALS), Parkinson's disease, Alzheimer's disease, prion disorders (e.g., BSE), frontotemporal dementia). In embodiments, the disease is a posterior eye indication (e.g., retinal degeneration (e.g., a subset of ND): retinitis pigmentosa (ADRP), Stargardt's disease, wet AMD (choroidal neovascularization-CNV), dry AMD). In embodiments, the disease is an anterior eye indication (e.g., glaucoma, Fuch's dystrophy). In embodiments, the disease is diabetes mellitus (e.g, typel (autoimmune), type 2 (e.g., obesity-induced/insulin-resistant), monogenic (e.g. MODY syndromes, for example pro-insulin mutations), recessive genetic disorders in which diabetes mellitus is a prominent component (e.g, Wolcott Rallisson syndrome (e.g., associated with Perk genetic deficiency), Wolfram syndrome (WFS1 or WFS2 deficiency)). In embodiments, the disease is a fibrosing disorder or fibrosis (e.g., idiopathic pulmonary fibrosis (IPF), familial pulmonary fibrosis (FPF), scleroderma (systemic sclerosis), renal fibrosis, hepatic fibrosis). In embodiments, the disease is a demyelinating disorder (e.g., multiple sclerosis (MS), Guillan-Barre, adrenoleukodystrophy, adrenomyeloneuropathy, optic neuritis, transverse myelitis). In embodiments, the disease is a peripheral neuropathy (e.g., primary such as Charcot-Marie Tooth (CMT) or secondary from diabetes mellitus). In embodiments, the disease is a dermatologic disease (e.g., psoriasis). In embodiments, the disease is a rheumatologic disease. In embodiments, the disease is an autoimmune disease (e.g., rheumatoid arthritis, Grave's disease, Hashimoto's Disease, Addison's disease, Lupus, ankylosing spondylitis, sarcoidosis). In embodiments, the compound treats an autoimmune disease associated with checkpoint inhibitor treatment (e.g., cancer treatment). In embodiments, the compound treats a disease (e.g., diabetes mellitus) associated with checkpoint inhibitor treatment (e.g., cancer treatment). In an aspect is provided a method of treating a disease in a subject in need thereof, the method including administering to the subject in need thereof an effective amount of a compound described herein, or a salt (e.g., pharmaceutically acceptable salt) thereof, wherein the disease is Type 1 Diabetes Melllitus, Type 2 Diabetes Mellitus, Mature Onset diabetes of the Young (MODY), Mutant INS-gene-induced Diabetes of the young (MIDY), Immune Checkpoint-induced Diabetes Mellitus, Wolfram's Syndrome, Wolcott-Rallison Syndrome, Idiopathic Pulmonary fibrosis (IPF), Familial Pulmonary Fibrosis (FPF), Asthma, Alzheimer's disease, Amyotrophic lateral sclerosis, Charcot-Marie-Tooth disease, Chronic traumatic encephalopathy, Cystic fibrosis, cytochrome c oxidase deficiency, degenerative Leigh syndrome, Ehlers-Danlos syndrome, Fibrodysplasia ossificans progressiva, Friedreich's ataxia, Frontotemporal dementia, cardiovascular diseases, coronary artery disease, aortic stenosis, Huntington's disease, Infantile neuroaxonal dystrophy, Keratoconus, Keratoglobus, Leukodystrophies, Wet Macular degeneration, Dry Macular degeneration, Marfan's syndrome, Some mitochondrial myopathies, Mitochondrial DNA depletion syndrome, Multiple sclerosis, Multiple system atrophy, Muscular dystrophies, Neuronal ceroid lipofuscinosis, Niemann-Pick diseases, Osteoarthritis, Osteoporosis, Parkinson's disease, Pulmonary arterial hypertension, prion disease, Creutzfeldt-Jakob disease, fatal familial insomnia, Progressive supranuclear palsy, Retinitis pigmentosa, Rheumatoid arthritis, Sandhoff Disease, Scleroderma, Spinal muscular atrophy, Subacute sclerosing panencephalitis, Tay-Sachs disease, Vascular dementia.

In embodiments, the method includes co-administering (e.g., in an effective amount, in a therapeutically effective amount) a second agent useful for treating the disease. In embodiments, the disease is a neurodegenerative disease (ND) (e.g., amyotrophic lateral sclerosis (ALS), Parkinson's disease, Alzheimer's disease, prion disorders (e.g., BSE), frontotemporal dementia), posterior eye indication (e.g., retinal degeneration (e.g. a subset of ND): retinitis pigmentosa (ADRP), Stargardt's disease, wet AMD (choroidal neovascularization-CNV), dry AMD), Anterior eye indication (e.g., glaucoma, Fuch's dystrophy), Diabetes mellitus (e.g., typel (autoimmune), type 2 (e.g., obesity-induced/insulin-resistant), monogenic (e.g., MODY syndromes, for example pro-insulin mutations), recessive genetic disorders in which diabetes mellitus is a prominent component (e.g., Wolcott Rallisson syndrome (e.g., associated with Perk genetic deficiency), Wolfram syndrome (WFS1 or WFS2 deficiency)), fibrosing disorder or fibrosis (e.g., idiopathic pulmonary fibrosis (IPF) (e.g., pirfenidone, nintedanib), familial pulmonary fibrosis (FPF), scleroderma (systemic sclerosis), renal fibrosis, hepatic fibrosis), demyelinating disorder (e.g., multiple sclerosis (MS), Guillan-Barre, adrenoleukodystrophy, adrenomyeloneuropathy, optic neuritis, transverse myelitis), peripheral neuropathy (e.g., primary such as Charcot-Marie Tooth (CMT) or secondary from diabetes mellitus), dermatologic disease (e.g., psoriasis), rheumatologic disease, or autoimmune disease (e.g., rheumatoid arthritis, Grave's disease, Hashimoto's Disease, Addison's disease, Lupus, ankylosing spondylitis, sarcoidosis).

Viruses are obligatory intracellular parasites that hijack and usurp cellular synthetic functions for their replications. The early secretory pathway (especially the ER) can be the site of both entry into the cytosol and an initial site for packaging and egress. Either non-enveloped viruses such as such as coxsackieviruses, rotavirus, or poliovirus, or enveloped viruses such as influenza virus, herpes simplex virus (HSV), human immunodeficiency virus (HIV), and SARS CoV-2 (the coronavirus that causes COVID-19) all are reported to exhibit high ER stress. In the case of SARS CoV-2, the viral replication cycle and maturation of both structural and non-structural proteins leads to upregulation of ER stress signaling components (PMCID: PMC7431030). Original SARS (CoV-1) and MERS both led to UPR upregulation (PMCID: PMC1563899). Thus, the role of coronaviruses in causing ER stress is established. In embodiments, the compounds described herein modulate host cell IRE1α in order to produce anti-viral activity (PMCID: PMC7480111). Furthermore, anti-inflammatory activity through unfolded protein response (UPR) inhibition with IRE1α inhibitors could provide clinical benefit. In embodiments, the compounds described herein may provide clinical benefit for SARS CoV-2 infection. In embodiments, the compounds described herein (e.g., IRE1α inhibitors) could provide clinical benefit in a variety of viral infections, including but not limited to infections associated with the viruses described above.

In an aspect is provided a method of treating a viral infection in a subject in need thereof, the method including administering to the subject in need thereof an effective amount of a compound described herein, or a salt (e.g., pharmaceutically acceptable salt) thereof. In embodiments the viral infection is associated with a non-enveloped viruse. In embodiments the viral infection is associated with a coxsackievirus, rotavirus, or poliovirus. In embodiments the viral infection is associated with an enveloped virus. In embodiments the viral infection is associated with an influenza virus, herpes simplex virus (HSV), human immunodeficiency virus (HIV), or SARS CoV-2 (the coronavirus that causes COVID-19). In embodiments the viral infection is associated with a virus associated with high ER stress. In embodiments the viral infection is associated with SARS (CoV-1). In embodiments the viral infection is associated with MERS. In embodiments the viral infection is associated with UPR upregulation. In embodiments the viral infection is associated with a coronavirus. In embodiments the viral infection is associated with ER stress. In embodiments, the compounds described herein modulate host cell IRE1α in order to produce anti-viral activity. In embodiments the viral infection is associated with SARS CoV-2. In embodiments, the method includes co-administering (e.g., in an effective amount, in a therapeutically effective amount) a second agent useful for treating the viral infection.

Compounds disclosed herein could prove useful in applications where increasing protein production output is desirable, such as in vitro cell free systems for protein production. Similarly production of antibodies by hybridomas may also be improved by addition of compounds disclosed herein.

In an aspect is provided a method of increasing protein expression of a cell or in vitro expression system, the method including administering an effective amount of a compound described herein, or a salt thereof, to the cell or in vitro expression system. In embodiments, the method is a method of increasing protein expression by a cell. In embodiments, the method is a method of increasing protein expression by an in vitro protein expression system.

In embodiments, the compound is useful as a comparator compound. In embodiments, the comparator compound can be used to assess the activity of a test compound in an assay (e.g., an assay as described herein, for example in the examples section, figures, or tables).

V. Embodiments

Embodiment P1. A compound having the formula:

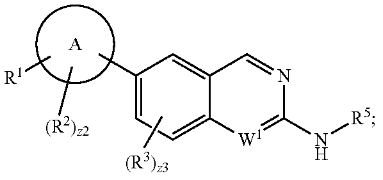

wherein,

Ring A is cycloalkyl, heterocycloalkyl, aryl, or heteroaryl;

$R^1$ is independently —$NR^{1A}SO_2R^{1B}$, —$NR^{1A}SOR^{1B}$, —$SOR^{1B}$, —$SO_2R^{1B}$, —$SONR^{1A}R^{1B}$, —$SO_2NR^{1A}R^{1B}$, —$NHC(O)NR^{1A}R^{1B}$, —$NR^{1A}R^{1B}$, —$C(O)R^{1B}$, —$OC(O)R^{1B}$, —$C(O)OR^{1B}$, —$C(O)NR^{1A}R^{1B}$, —$OR^{1B}$, —$NR^{1A}C(O)R^{1B}$, —$NR^{1A}C(O)OR^{1B}$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl;

$R^{1A}$ and $R^{1B}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$, substituents bonded to the same nitrogen atom may optionally be joined to form a substituted or unsubstituted heterocycloalkyl;

$R^z$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —C(O)—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

z2 is an integer from 0 to 4;

$R^3$ is independently halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$ $NR^{3C}NR^{3A}R^{3B}$, —$ONR^{3A}R^{3B}$, —$NHC(O)NR^{3C}NR^{3A}R^{3B}$, —$NHC(O)NR^{3A}R^{3B}$, —$N(O)_{m3}$, —$NR^{3A}$R3B, —$C(O)R^{3C}$, —C(O)—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl;

z3 is independently an integer from 0 to 4;

$W^1$ is —N═, —CH═, or —$CR^3$═;

$R^5$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$, $R^{2B}$, $R^{2C}$, $R^{2D}$, $R^{3A}$, $R^{3B}$, $R^{3C}$, and $R^{3D}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$, substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

$X^2$ and $X^3$ are independently —F, —Cl, —Br, or —I;

n2 and n3 are independently an integer from 0 to 4; and m2, m3, v2, and v3 are independently 1 or 2;

or a salt thereof.

Embodiment P2. The compound of embodiment P1, wherein $R^5$ is independently substituted or unsubstituted $C_1$-$C_4$ alkyl, substituted or unsubstituted 2 to 4 membered heteroalkyl, substituted or unsubstituted cycloalkyl, substituted or unsubstituted heterocycloalkyl, substituted or unsubstituted aryl, or substituted or unsubstituted heteroaryl.

Embodiment P3. The compound of one of embodiments P1 to P2, having the formula:

(Ia)

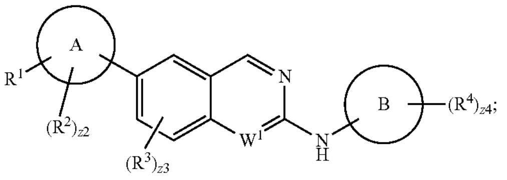

wherein,

Ring B is cycloalkyl, heterocycloalkyl, aryl, or heteroaryl;

$R^4$ is independently oxo, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NR^{4C}NR^{4A}R^{4B}$, —$ONR^{4A}R^{4B}$, —NHC(O)$NR^{4A}R^{4B}$, —NHC(O)$NR^{4A}R^{4B}$, —$N(O)_{m4}$, —$NR^{4A}R^{4B}$, —C(O)$R^{4C}$, —OC(O)$R^{4C}$, —C(O)—$OR^{4C}$, —OC(O)—$OR^{4C}$, —C(O)$NR^{4A}R^{4B}$, —OC(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^4$ substituents may optionally be joined to form a substituted or unsubstituted cycloalkyl, substituted or unsubstituted heterocycloalkyl, substituted or unsubstituted aryl, or substituted or unsubstituted heteroaryl;

z4 is independently an integer from 0 to 5;

$R^{4A}$, $R^{4B}$, $R^{4C}$, and $R^{4D}$ are independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

$X^4$ is independently —F, —Cl, —Br, or —I;

n4 is independently an integer from 0 to 4; and m4 and v4 are independently 1 or 2; and or a salt thereof.

Embodiment P4. The compound of embodiment P3, wherein Ring B is $C_5$-$C_6$ cycloalkyl, 5 to 6 membered heterocycloalkyl, phenyl, or 5 to 6 membered heteroaryl.

Embodiment P5. The compound of embodiment P3, having the formula:

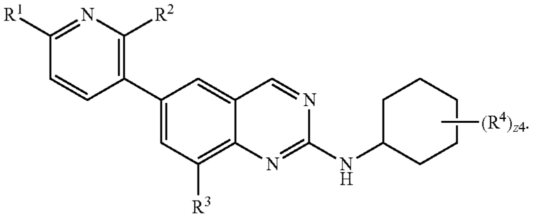

Embodiment P6. The compound of one of embodiments P1 to P5, wherein $R^1$ is independently —$NR^{1A}SO_2R^{1B}$, —$NR^{1A}SOR^{1B}$, or —$NR^{1A}C(O)R^{1B}$;

$R^{1A}$ is independently hydrogen or unsubstituted $C_1$-$C_4$ alkyl; and $R^{1B}$ is independently hydrogen, halo-substituted or unsubstituted $C_1$-$C_2$ alkyl, or halo-substituted or unsubstituted $C_3$-$C_4$ cycloalkyl.

Embodiment P7. The compound of one of embodiments P1 to P6, wherein $R^{1A}$ is independently hydrogen; and $R^{1B}$ is independently hydrogen, halo-substituted or unsubstituted $C_1$-$C_2$ alkyl, or halo-substituted or unsubstituted $C_3$-$C_4$ cycloalkyl.

Embodiment P8. The compound of one of embodiments P1 to P6, wherein $R^{1A}$ is independently hydrogen; and $R^{1B}$ is independently halo-substituted or unsubstituted $C_1$-$C_2$ alkyl, or halo-substituted or unsubstituted $C_3$-$C_4$ cycloalkyl.

Embodiment P9. The compound of one of embodiments P1 to P8, having the formula:

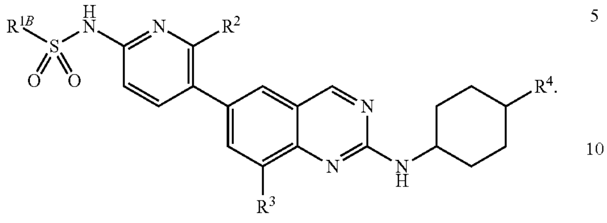

Embodiment P10. The compound of one of embodiments P1 to P9, wherein $R^2$ is independently $—OCX^2_3$, $—OCH_2X^2$, $—OCHX^2_2$, or $—OR^{2D}$, unsubstituted alkyl; and $R^{2D}$ is independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, or unsubstituted $C_1$-$C_4$ alkyl.

Embodiment P11. The compound of one of embodiments P1 to P9, wherein $R^2$ is independently $—OCX^2_3$, $—OCH_2X^2$, $—OCHX^2_2$, or $—OCH_3$.

Embodiment P12. The compound of one of embodiments P1 to P11, wherein $R^3$ is independently $—CX^3_3$, $—CHX^3_2$, $—CH_2X^3$, or unsubstituted $C_1$-$C_4$ alkyl.

Embodiment P13. The compound of one of embodiments P1 to P11, wherein $R^3$ is independently unsubstituted $C_1$-$C_3$ alkyl.

Embodiment P14. The compound of one of embodiments P1 to P13, wherein $R^4$ is independently $—NR^{4A}R^{4B}$; and $R^{4A}$ and $R^{4B}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, or unsubstituted $C_1$-$C_4$ alkyl.

Embodiment P15. The compound of one of embodiments P1 to P13, wherein $R^4$ is independently $—NH_2$.

Embodiment P16. The compound of one of embodiments P1 to P15, having the formula:

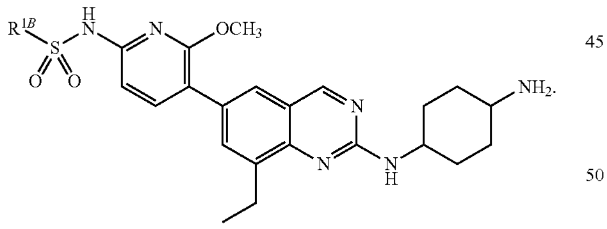

Embodiment P17. The compound of one of embodiments P1 to P15, having the formula:

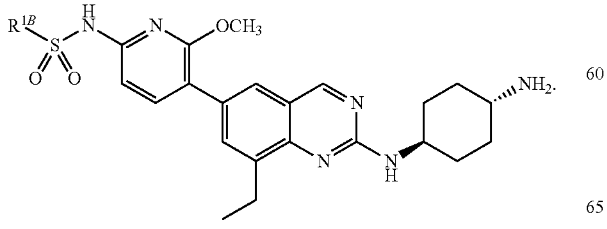

Embodiment P18. The compound of one of embodiments P1 to P17, wherein $R^{1B}$ is independently halo-substituted $C_1$-$C_2$ alkyl, or unsubstituted $C_3$-$C_4$ cycloalkyl.

Embodiment P19. The compound of one of embodiments P1 to P17, wherein $R^{1B}$ is independently fluoro-substituted $C_1$-$C_2$ alkyl, or unsubstituted $C_3$-$C_4$ cycloalkyl.

Embodiment P20. The compound of one of embodiments P1 to P17, wherein R" is independently-$CH_2CF_3$.

Embodiment P21. The compound of one of embodiments P1 to P17, wherein RB is independently unsubstituted cyclopropyl.

Embodiment P22. A pharmaceutical composition comprising the compound of any one of embodiments P1 to P21 and a pharmaceutically acceptable excipient.

Embodiment P23. A method of treating a cell degenerative disease in a subject in need thereof, said method comprising administering to the subject in need thereof an effective amount of a compound of one of embodiments P1 to P21.

Embodiment P24. The method of embodiment P23, wherein the cell degenerative disease is a neurodegenerative disease.

Embodiment P25. The method of embodiment P23, wherein the cell degenerative disease is diabetes, pulmonary fibrosis, Alzheimer's disease, Amyotrophic lateral sclerosis, Charcot-Marie-Tooth disease, Chronic traumatic encephalopathy, Cystic fibrosis, cytochrome c oxidase deficiencie, degenerative Leigh syndrome, Ehlers-Danlos syndrome, Fibrodysplasia ossificans progressiva, Friedreich's ataxia, Frontotemporal dementia, cardiovascular diseases, coronary artery disease, aortic stenosis, Huntington's disease, Infantile neuroaxonal dystrophy, Keratoconus, Keratoglobus, Leukodystrophies, Macular degeneration, Marfan's syndrome, Some mitochondrial myopathies, Mitochondrial DNA depletion syndrome, Multiple sclerosis, Multiple system atrophy, Muscular dystrophies, Neuronal ceroid lipofuscinosis, Niemann-Pick diseases, Osteoarthritis, Osteoporosis, Parkinson's disease, Pulmonary arterial hypertension, prion disease, Creutzfeldt-Jakob disease, fatal familial insomnia, Progressive supranuclear palsy, Retinitis pigmentosa, Rheumatoid arthritis, Sandhoff Disease, Spinal muscular atrophy, Subacute sclerosing panencephalitis, Tay-Sachs disease, Vascular dementia, Embodiment P26. The method of one of embodiments P23 to P25, further comprising co-administering an agent for treating a cell degenerative disease to said subject in need.

Embodiment P27. A method of treating a disease in a subject in need thereof, said method comprising administering to the subject in need thereof an effective amount of a compound of one of embodiments P1 to P21, wherein the disease is Type 1 Diabetes Melllitus, Type 2 Diabetes Mellitus, Mature Onset diabetes of the Young (MODY), Mutant INS-gene-induced Diabetes of the young (MIDY), Immune Checkpoint-induced Diabetes Mellitus, Wolfram's Syndrome, Wolcott-Rallison Syndrome, Idiopathic Pulmonary fibrosis (IPF), Familial Pulmonary Fibrosis (FPF), Asthma, Alzheimer's disease, Amyotrophic lateral sclerosis, Charcot-Marie-Tooth disease, Chronic traumatic encephalopathy, Cystic fibrosis, cytochrome c oxidase deficiencie, degenerative Leigh syndrome, Ehlers-Danlos syndrome, Fibrodysplasia ossificans progressiva, Friedreich's ataxia, Frontotemporal dementia, cardiovascular diseases, coronary artery disease, aortic stenosis, Huntington's disease, Infantile neuroaxonal dystrophy, Keratoconus, Keratoglobus, Leukodystrophies, Wet Macular degeneration, Dry Macular degeneration, Marfan's syndrome, Some mitochondrial myopathies, Mitochondrial DNA depletion syndrome, Multiple sclerosis, Multiple system atrophy, Muscular dystrophies, Neuronal ceroid lipofuscinosis, Niemann-Pick diseases, Osteoarthritis, Osteoporosis, Parkinson's disease, Pulmonary arterial hypertension, prion disease, Creutzfeldt-Jakob disease, fatal familial insomnia, Progressive supranuclear palsy, Retinitis pigmentosa, Rheumatoid arthritis, Sandhoff Disease, Scleroderma, Spinal muscular atrophy, Subacute sclerosing panencephalitis, Tay-Sachs disease, Vascular dementia, or cancer.

VI. Additional Embodiments

Embodiment 1. A compound having the formula:

(I)

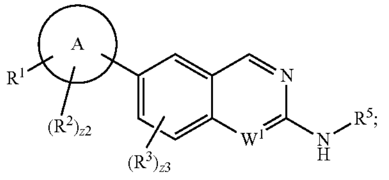

wherein

Ring A is cycloalkyl, heterocycloalkyl, aryl, or heteroaryl;

$R^1$ is $-NR^{1A}SO_2R^{1B}$, $-NR^{1A}SOR^{1B}$, $-SOR^{1B}$, $-SO_2R^{1B}$, $-SONR^{1A}R^{1B}$, $-SO_2NR^{1A}R^{1B}$, $-NHC(O)NR^{1A}R^{1B}$, $-NR^{1A}R^{1B}$, $-C(O)R^{1B}$, $-OC(O)R^{1B}$, $-C(O)OR^{1B}$, $-C(O)NR^{1A}R^{1B}$, $-OR^{1B}$, $-NR^{1A}C(O)R^{1B}$, $-NR^{1A}C(O)OR^{1B}$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl;

$R^{1A}$ and $R^{1B}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl; $R^{1A}$ and $R^{1B}$ substituents bonded to the same nitrogen atom may optionally be joined to form a substituted or unsubstituted heterocycloalkyl;

$R^2$ is independently oxo, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

z2 is an integer from 0 to 4;

$R^3$ is independently halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NR^{3C}NR^{3A}R^{3B}$, $-ONR^{3A}R^{3B}$, $-NHC(O)NR^{3C}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl;

z3 is an integer from 0 to 4;

$W^1$ is $-N=$, $-CH=$, or $-CR^3=$;

$R^5$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$, $R^{2B}$, $R^{2C}$, $R^{2D}$, $R^{3A}$, $R^{3B}$, $R^{3C}$, and $R^{3D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $X^2$ and $X^3$ are independently $-F$, $-Cl$, $-Br$, or $-I$;

n2 and n3 are independently an integer from 0 to 4; and m2, m3, v2, and v3 are independently 1 or 2;

or a salt thereof.

Embodiment 2. The compound of embodiment 1, wherein $R^5$ is substituted or unsubstituted $C_1$-$C_4$ alkyl, substituted or unsubstituted 2 to 4 membered heteroalkyl, substituted or unsubstituted cycloalkyl, substituted or unsubstituted heterocycloalkyl, substituted or unsubstituted aryl, or substituted or unsubstituted heteroaryl.

Embodiment 3. The compound of one of embodiments 1 to 2, having the formula:

(Ia)

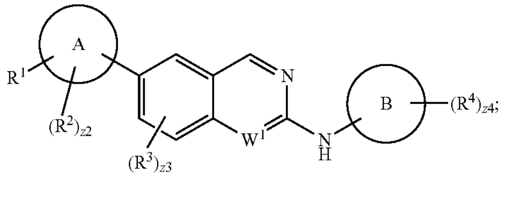

wherein

Ring B is cycloalkyl, heterocycloalkyl, aryl, or heteroaryl;

$R^4$ is independently oxo, halogen, $—CX^4_3$, $—CHX^4_2$, $—CH_2X^4$, $—OCX^4_3$, $—OCH_2X^4$, $—OCHX^4_2$, —CN, $—SO_{n4}R^{4D}$, $SO_{v4}NR^{4A}R^{4B}$, $—NR^{4C}NR^{4A}R^{4B}$, $—ONR^{4A}R^{4B}$, $—NHC(O)NR^{4C}NR^{4A}R^{4B}$, $—NHC(O)NR^{4A}R^{4B}$, $—N(O)_{m4}$, $—NR^{4A}R^{4B}$, $—C(O)R^{4C}$, $—OC(O)R^{4C}$, $—C(O)—OR^{4C}$, $—OC(O)—OR^{4C}$, $—C(O)NR^{4A}R^{4B}$, $—OC(O)NR^{4A}R^{4B}$, $—OR^{4D}$, $—NR^{4A}SO_2R^{4D}$, $—NR^{4A}C(O)R^{4C}$, $—NR^{4A}C(O)OR^{4C}$, $—NR^{4A}OR^{4C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^4$ substituents may optionally be joined to form a substituted or unsubstituted cycloalkyl, substituted or unsubstituted heterocycloalkyl, substituted or unsubstituted aryl, or substituted or unsubstituted heteroaryl;

z4 is an integer from 0 to 5;

$R^{4A}$, $R^{4B}$, $R^{4C}$, and $R^{4D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

$X^4$ is independently —F, —Cl, —Br, or —I;

n4 is an integer from 0 to 4; and m4 and v4 are independently 1 or 2;

or a salt thereof.

Embodiment 4. The compound of embodiment 3, wherein Ring B is $C_5$-$C_6$ cycloalkyl, 5 to 6 membered heterocycloalkyl, phenyl, or 5 to 6 membered heteroaryl.

Embodiment 5. The compound of embodiment 3, having the formula:

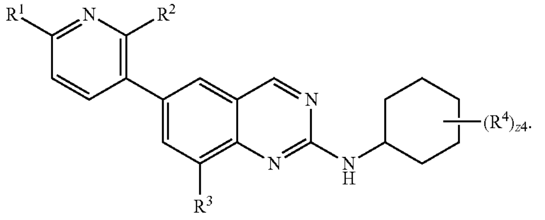

Embodiment 6. The compound of one of embodiments 1 to 5, wherein $R^1$ is $—NR^{1A}SO_2R^{1B}$, $—NR^{1A}SOR^{1B}$, or $—NR^{1A}C(O)R^{1B}$.

$R^{1A}$ is hydrogen or unsubstituted $C_1$-$C_4$ alkyl; and $R^{1B}$ is hydrogen, halo-substituted or unsubstituted $C_1$-$C_2$ alkyl, halo-substituted or unsubstituted $C_3$-$C_4$ cycloalkyl, or halo-substituted or unsubstituted phenyl.

Embodiment 7. The compound of one of embodiments 1 to 6, wherein $R^{1A}$ is hydrogen; and $R^{1B}$ is hydrogen, halo-substituted or unsubstituted $C_1$-$C_2$ alkyl, or halo-substituted or unsubstituted $C_3$-$C_4$ cycloalkyl.

Embodiment 8. The compound of one of embodiments 1 to 6, wherein $R^{1A}$ is hydrogen; and $R^{1B}$ is halo-substituted or unsubstituted $C_1$-$C_2$ alkyl, or halo-substituted or unsubstituted $C_3$-$C_4$ cycloalkyl.

Embodiment 9. The compound of one of embodiments 3 to 8, having the formula:

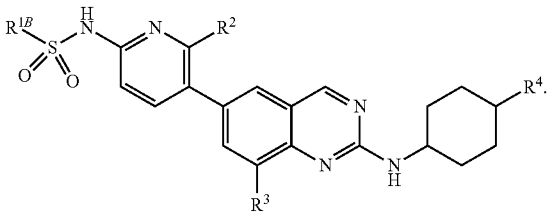

Embodiment 10. The compound of one of embodiments 1 to 9, wherein $R^2$ is independently $—OCX^2_3$, $—OCH_2X^2$, $—OCHX^2_2$, or $—OR^{2D}$, unsubstituted alkyl; and $R^{2D}$ is hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, or unsubstituted $C_1$-$C_4$ alkyl.

Embodiment 11. The compound of one of embodiments 1 to 9, wherein $R^2$ is independently $—OCX^2_3$, $—OCH_2X^2$, $—OCHX^2_2$, or $—OCH_3$.

Embodiment 12. The compound of one of embodiments 1 to 11, wherein $R^3$ is independently $—CX^3_3$, $—CHX^3_2$, $—CH_2X^3$, or unsubstituted $C_1$-$C_4$ alkyl.

Embodiment 13. The compound of one of embodiments 1 to 11, wherein $R^3$ is independently unsubstituted $C_1$-$C_3$ alkyl.

Embodiment 14. The compound of one of embodiments 3 to 13, wherein $R^4$ is independently $—NR^{4A}R^{4B}$; and $R^{4A}$ and $R^{4B}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, or unsubstituted $C_1$-$C_4$ alkyl.

Embodiment 15. The compound of one of embodiments 3 to 13, wherein $R^4$ is independently $—NH_2$.

Embodiment 16. The compound of one of embodiments 1 to 15, having the formula:

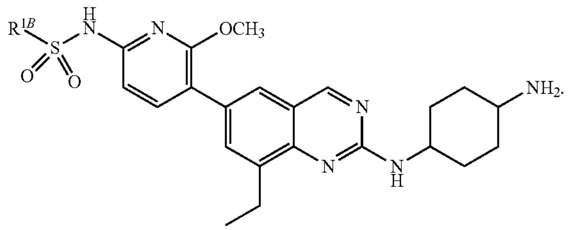

Embodiment 17. The compound of one of embodiments 1 to 15, having the formula:

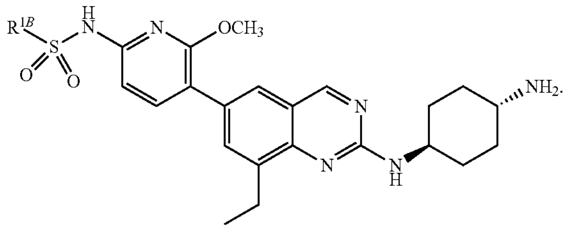

Embodiment 18. The compound of one of embodiments 1 to 17, wherein RB is halo-substituted $C_1$-$C_2$ alkyl, or unsubstituted $C_3$-$C_4$ cycloalkyl.

Embodiment 19. The compound of one of embodiments 1 to 17, wherein RB is fluoro-substituted $C_1$-$C_2$ alkyl, or unsubstituted $C_3$-$C_4$ cycloalkyl.

Embodiment 20. The compound of one of embodiments 1 to 17, wherein $R^{1B}$, is —$CH_2CF_3$.

Embodiment 21. The compound of one of embodiments 1 to 17, wherein $R^{1B}$ is unsubstituted cyclopropyl.

Embodiment 22. A pharmaceutical composition comprising a compound of any one of embodiments 1 to 21 and a pharmaceutically acceptable excipient.

Embodiment 23. A method of treating a cell degenerative disease in a subject in need thereof, said method comprising administering to the subject in need thereof an effective amount of a compound of one of embodiments 1 to 21.

Embodiment 24. The method of embodiment 23, wherein the cell degenerative disease is a neurodegenerative disease.

Embodiment 25. The method of embodiment 23, wherein the cell degenerative disease is diabetes, pulmonary fibrosis, Alzheimer's disease, Amyotrophic lateral sclerosis, Charcot-Marie-Tooth disease, Chronic traumatic encephalopathy, Cystic fibrosis, cytochrome c oxidase deficiency, degenerative Leigh syndrome, Ehlers-Danlos syndrome, Fibrodysplasia ossificans progressiva, Friedreich's ataxia, Frontotemporal dementia, cardiovascular diseases, coronary artery disease, aortic stenosis, Huntington's disease, Infantile neuroaxonal dystrophy, Keratoconus, Keratoglobus, Leukodystrophies, Macular degeneration, Marfan's syndrome, Some mitochondrial myopathies, Mitochondrial DNA depletion syndrome, Multiple sclerosis, Multiple system atrophy, Muscular dystrophies, Neuronal ceroid lipofuscinosis, Niemann-Pick diseases, Osteoarthritis, Osteoporosis, Parkinson's disease, Pulmonary arterial hypertension, prion disease, Creutzfeldt-Jakob disease, fatal familial insomnia, Progressive supranuclear palsy, Retinitis pigmentosa, Rheumatoid arthritis, Sandhoff Disease, Spinal muscular atrophy, Subacute sclerosing panencephalitis, Tay-Sachs disease, or Vascular dementia.

Embodiment 26. The method of one of embodiments 23 to 25, further comprising co-administering an agent for treating a cell degenerative disease to said subject in need.

Embodiment 27. A method of treating a disease in a subject in need thereof, said method comprising administering to the subject in need thereof an effective amount of a compound of one of embodiments 1 to 21, wherein the disease is Type 1 Diabetes Melllitus, Type 2 Diabetes Mellitus, Mature Onset diabetes of the Young (MODY), Mutant INS-gene-induced Diabetes of the young (MIDY), Immune Checkpoint-induced Diabetes Mellitus, Wolfram's Syndrome, Wolcott-Rallison Syndrome, Idiopathic Pulmonary fibrosis (IPF), Familial Pulmonary Fibrosis (FPF), Asthma, Alzheimer's disease, Amyotrophic lateral sclerosis, Charcot-Marie-Tooth disease, Chronic traumatic encephalopathy, Cystic fibrosis, cytochrome c oxidase deficiency, degenerative Leigh syndrome, Ehlers-Danlos syndrome, Fibrodysplasia ossificans progressiva, Friedreich's ataxia, Frontotemporal dementia, cardiovascular diseases, coronary artery disease, aortic stenosis, Huntington's disease, Infantile neuroaxonal dystrophy, Keratoconus, Keratoglobus, Leukodystrophies, Wet Macular degeneration, Dry Macular degeneration, Marfan's syndrome, Some mitochondrial myopathies, Mitochondrial DNA depletion syndrome, Multiple sclerosis, Multiple system atrophy, Muscular dystrophies, Neuronal ceroid lipofuscinosis, Niemann-Pick diseases, Osteoarthritis, Osteoporosis, Parkinson's disease, Pulmonary arterial hypertension, prion disease, Creutzfeldt-Jakob disease, fatal familial insomnia, Progressive supranuclear palsy, Retinitis pigmentosa, Rheumatoid arthritis, Sandhoff Disease, Scleroderma, Spinal muscular atrophy, Subacute sclerosing panencephalitis, Tay-Sachs disease, Vascular dementia, or cancer.

EXAMPLES

Described herein are new IRE1α kinase inhibitors that at full occupancy of the kinase domain cause partial antagonism of the RNase.

Described herein are small molecule kinase inhibitors which we named 'PAIR's for (Partial Antagonists of IRE1α RNase). Without being bound by theory, compound described herein bind ATP-competitively in the kinase to partially displace the IRE1α kinase helix αC, leading to stabilization of dimeric IRE1α species. In insulin-producing beta cells, PAIRs permit adaptive XBP1 mRNA splicing, while quelling destructive/terminal outputs from extra-XBP1 mRNA endonucleolytic decay, thus preventing apoptosis. Preservation of XBP1 splicing by PAIRs permits B-cells to differentiate into immunoglobulin-producing plasma cells.

In summary, an intermediate RNAse-inhibitory "sweet spot", achieved by PAIR-bound IRE1α, may capture a structural conformation naturally available to IRE1α that could represent a desirable therapeutic state for drugging this master UPR sensor/effector.

Here, we demonstrate that it is possible to design ATP-competitive inhibitors, which we call Partial Antagonists of IRE1α RNase (PAIRs), that fully engage IRE1α's kinase domain but only partially inhibit its RNase activity. By systematically defining the structural features of PAIRs that lead to stabilization of the kinase domain of IRE1α in this "intermediate" activation mode, we highlight new understanding of both the structure-activity relationships of PAIRs while comparing these to previous activators and full inhibitors of IRE1α.

The degree of outward displacement of the helix αC in IRE1α's kinase domain is the key determinant of these differential RNase activation states. Enforcing such an optimal IRE1α RNase activation state in cells allows partial activation of the RNase, sufficient to largely splice XBP1 mRNA, while mostly inhibiting RIDD. Finally, PAIRs have the unique ability to segregate distinct biological outputs of IRE1α in cellular systems by chiseling away destructive (RIDD-dependent) cell fate outputs from adaptive (XBP1 splicing-dependent) outputs. In this regard, PAIRs may represent a new pharmacological modality for addressing cell degeneration-namely by preserving an adaptive, while blunting, a terminal-UPR.

Example 1: Activation Loop Phosphorylation and ATP-Binding Site Ligands Rheostatically Tune IRE1α's Dimerization Affinity In order to better understand how to achieve an optimal intermediate RNase activation state through engagement of IRE1α's kinase domain, we first established a quantitative in vitro framework for characterizing how ATP-binding site occupancy influences RNase activity. It has been demonstrated that IRE1α must form a dimer in order for its RNase domain to be catalytically active (FIG. 1A). This dimeric state-commonly referred to as the "back-to-back" dimer—is characterized by an extensive interface between the kinase and RNase domains of each IRE1α protomer; this dimeric state can be promoted through mass action as IRE1α concentration is raised. Phosphorylation of IRE1α's activation loop has been demonstrated to promote the RNase activity of IRE1α by promoting dimer formation (PMIDs:). Furthermore, ligands that occupy the ATP-binding site of the kinase domain can also stimulate IRE1α's RNase activity by promoting dimer formation. We measured the ability of a purified, recombinant kinase/RNase domain construct of IRE1α-called IRE1α* to cleave a FRET-quenched XBP1 RNA mini-substrate as a function of IRE1α* concentration, in order to provide a quantitative metric of IRE1α's dimer affinity ($K_{dimer}$) (FIG. 1).

Figure 1C:
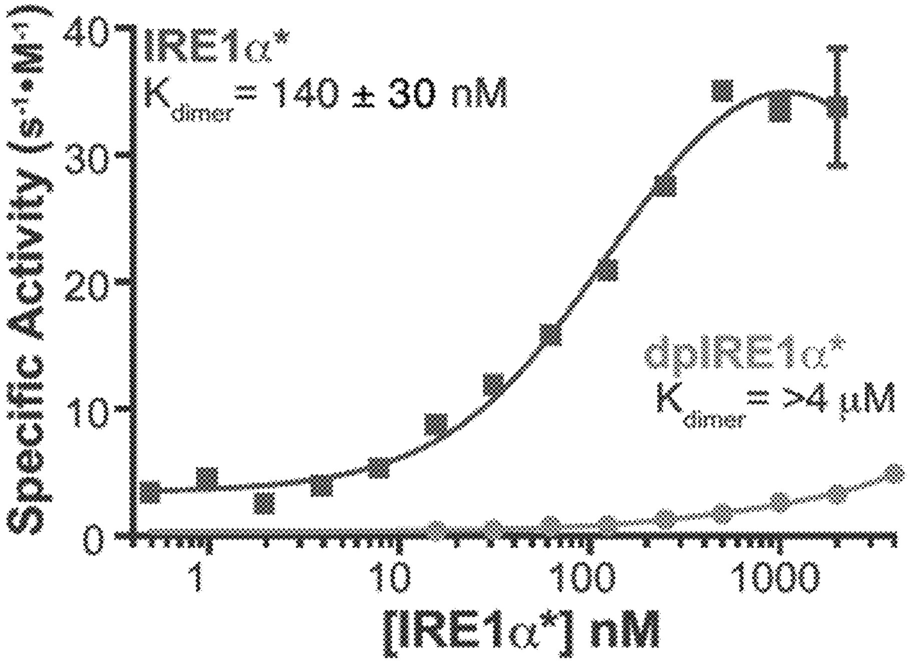
Figure 1D:
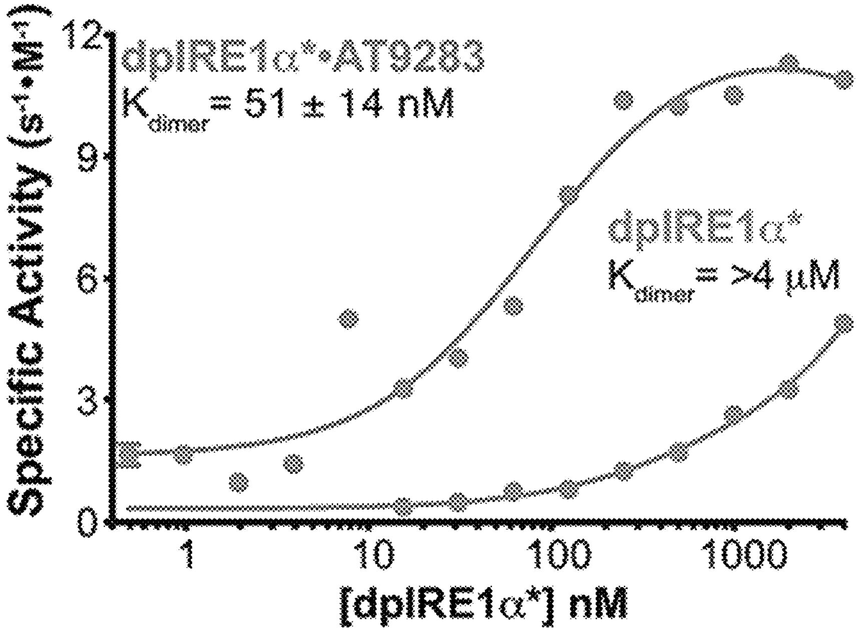
Figure 1E:
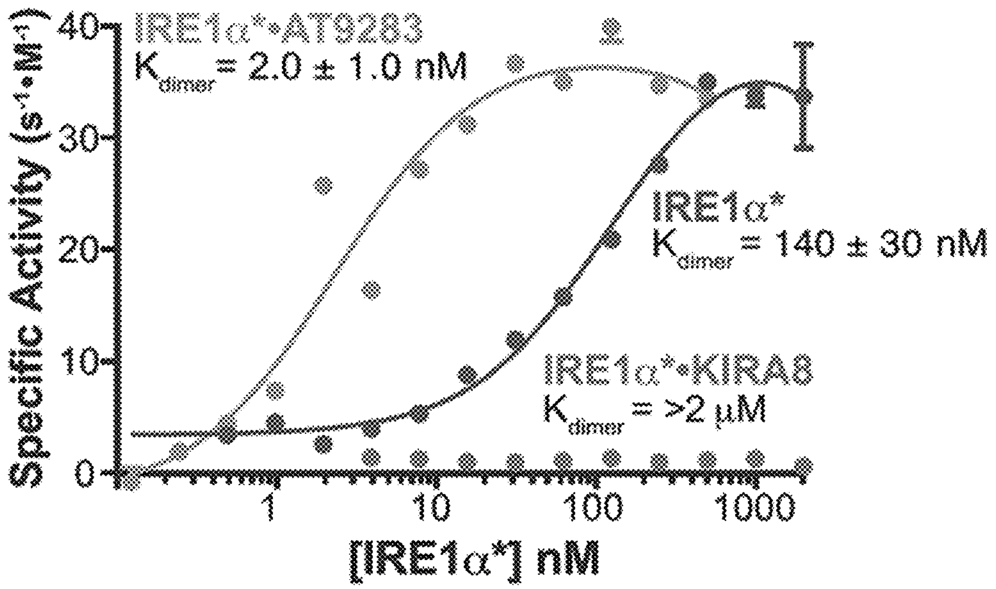
Figure 2A:
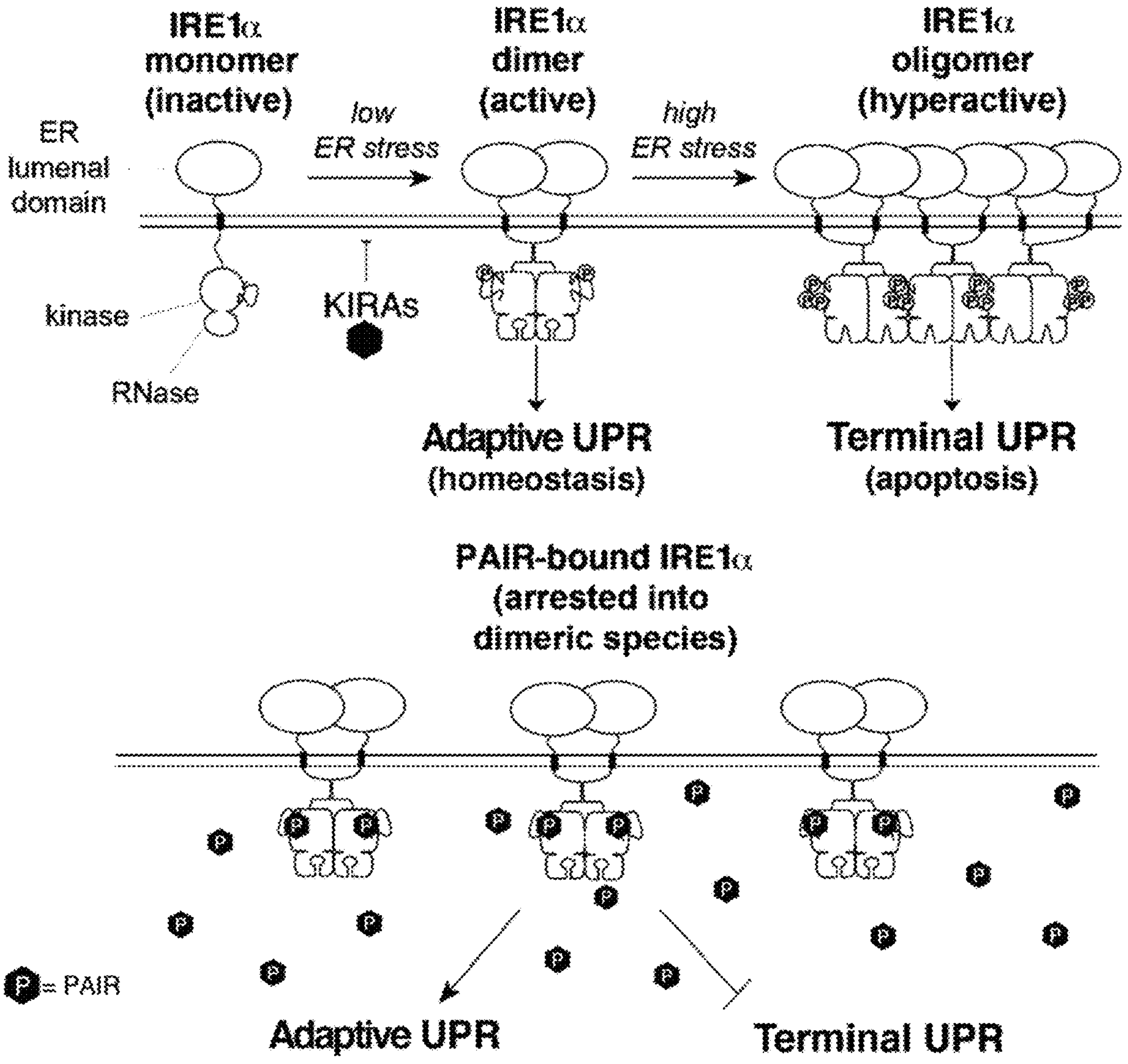
FIGS. 2A-2B. PAIR inhibition.
Figure 2B:
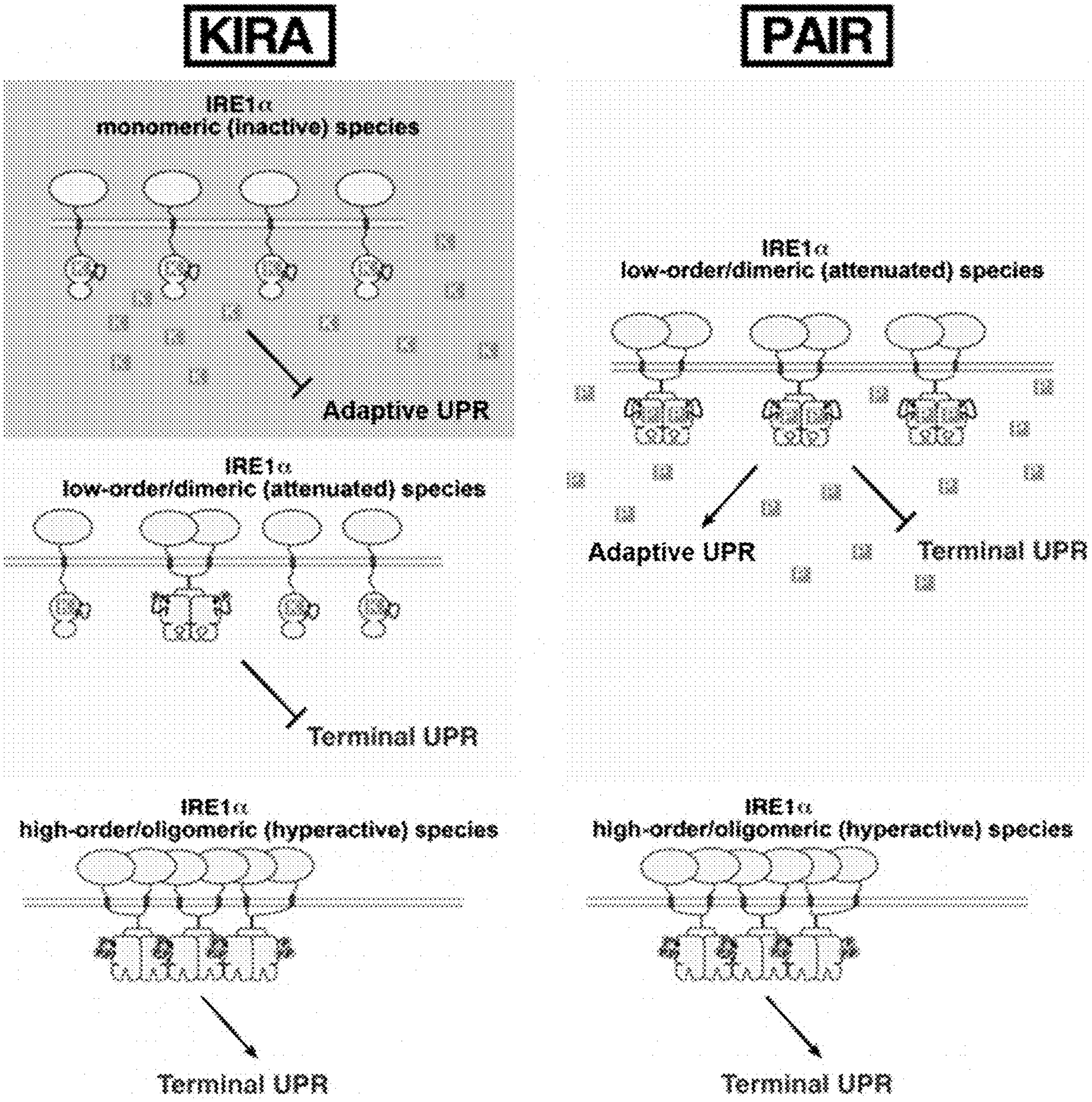
Figure 3:
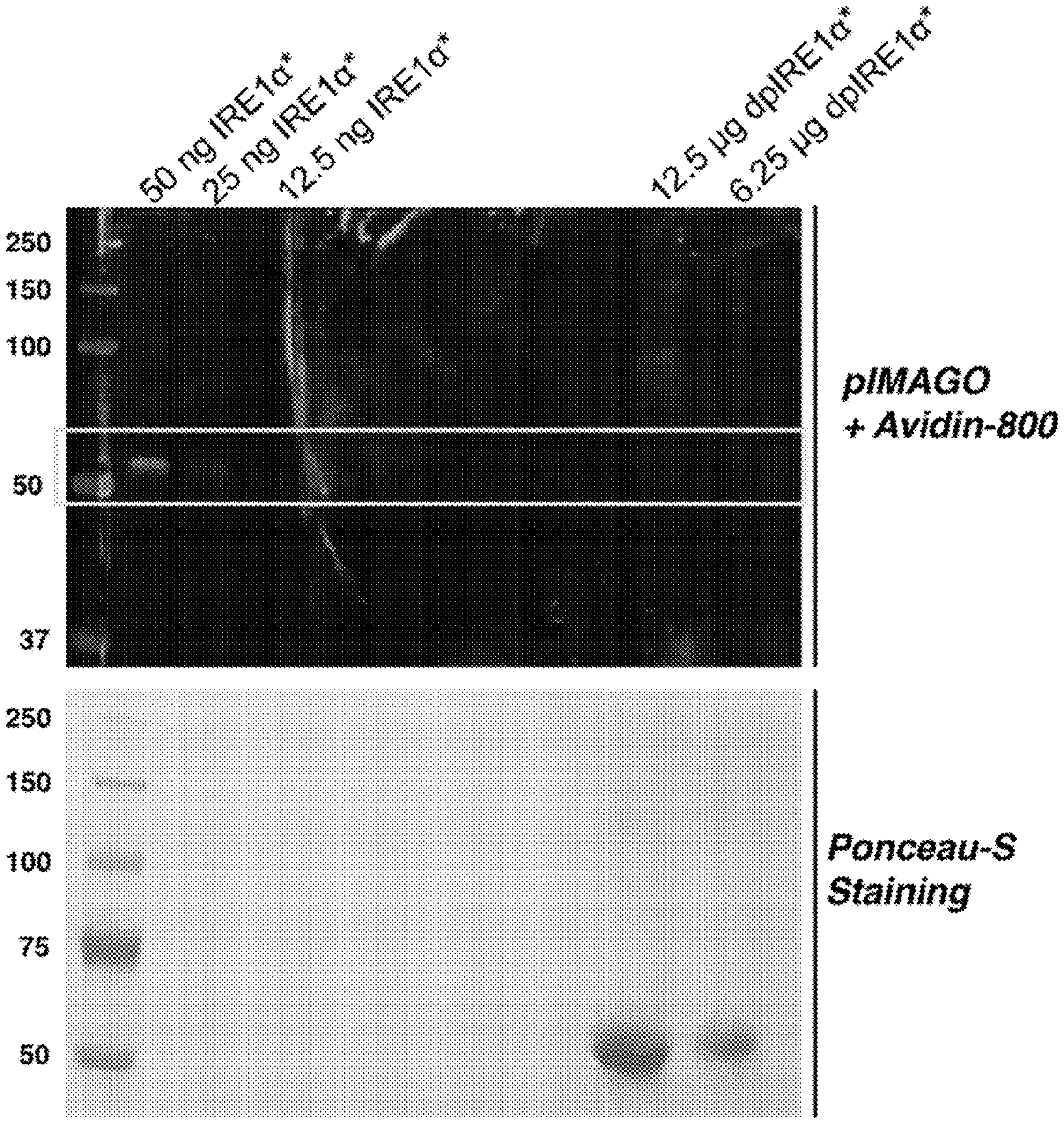
FIG. 3. Dephosphorylated IRE1α* (dpIRE1α*) is quantitatively dephosphorylated. Tymora pIMAGO phosphoprotein (top gel) and Ponceau-S (bottom gel) staining of 12,500 ng and 6,250 ng of dpIRE1α* (far right lanes) and 50 to 12.5 ng of IRE1α* (lanes 1-3).
Figure 4:
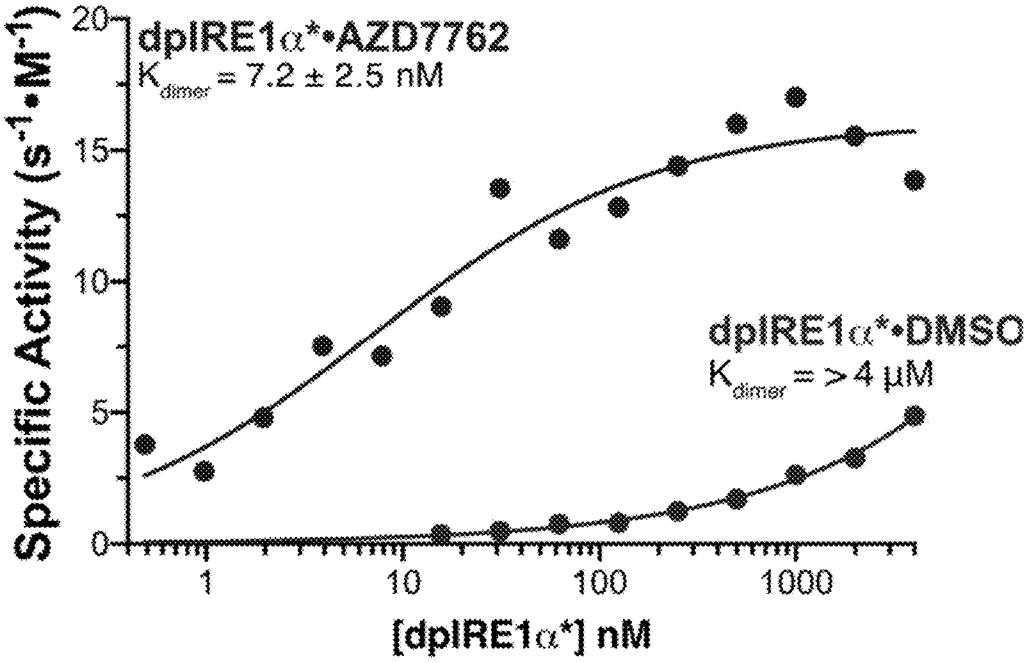
FIG. 4. AZD7762 promotes the formation of the RNase active dimer of dpIRE1α*. Kaimer curve of dpIRE1α*-AZD7762 complex (top curve). The Kaimer curve of apo dpIRE1α* (bottom curve) from FIG. 1C is shown for comparison. Data points shown are the mean±SEM, n=3.
Figure 5:
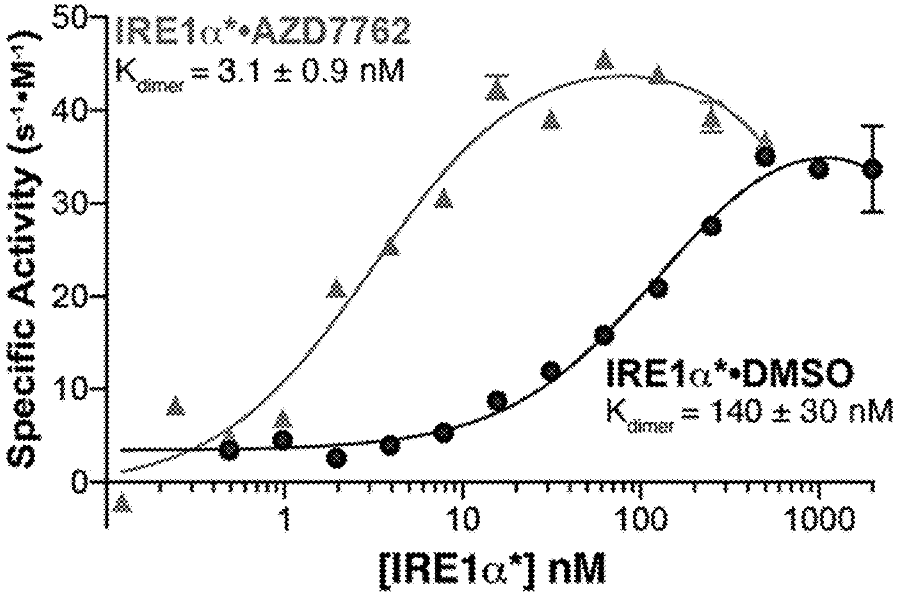
FIG. 5. AZD7762 promotes the formation of the RNase active dimer of IRE1α*. Kaimer curve of IRE1α*-AZD7762 complex (triangles). The $K_{dimer}$ curve of apo IRE1α* (circles) from FIG. 1C is shown as a comparison. Data points shown are the mean±SEM, n=3.
Figure 6A:
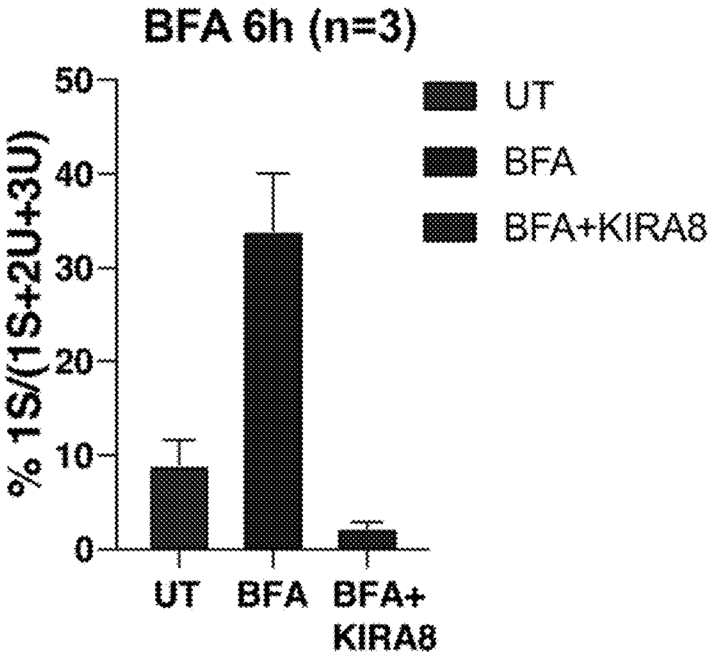
FIGS. 6A-6D. KIRA8 completely suppresses XBP1 splicing in ER-stressed INS-1 cells.
Figure 6B:
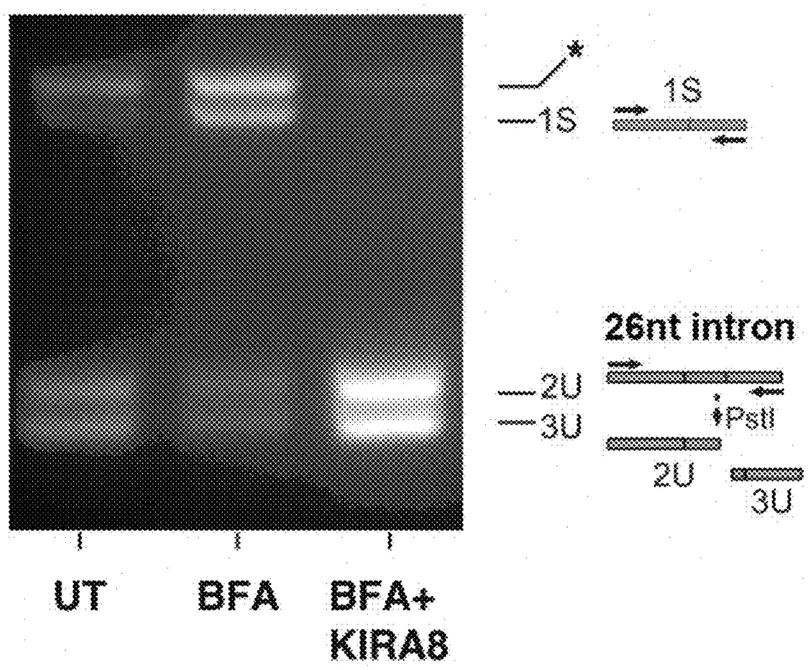
Figure 6C:
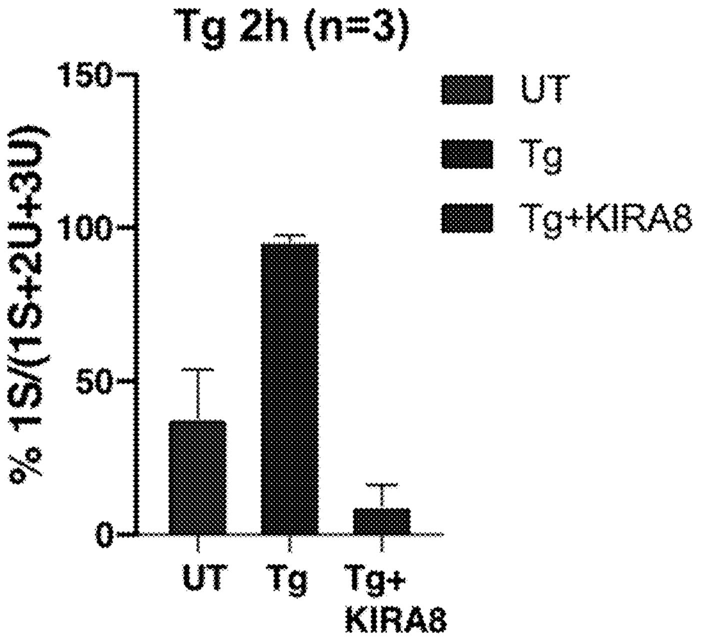
Figure 6D:
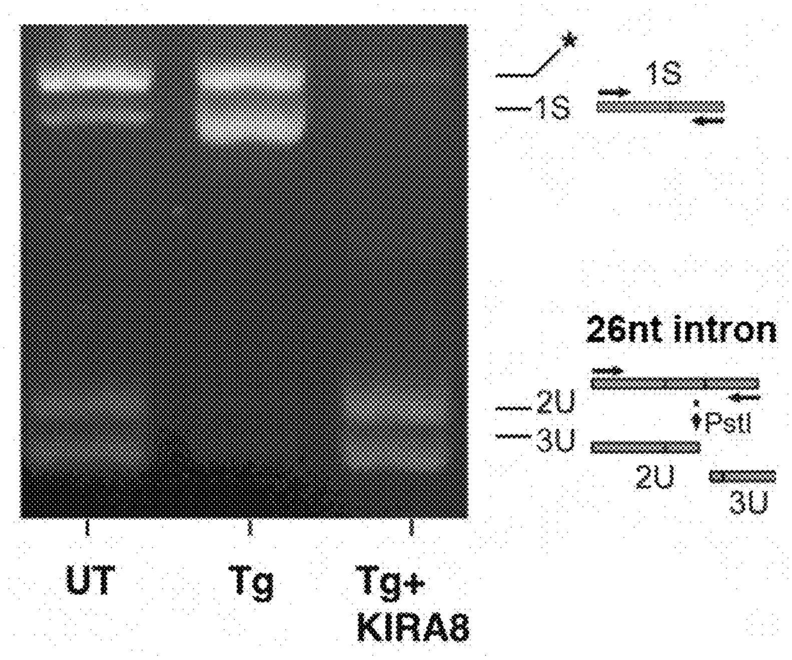
Figure 7:
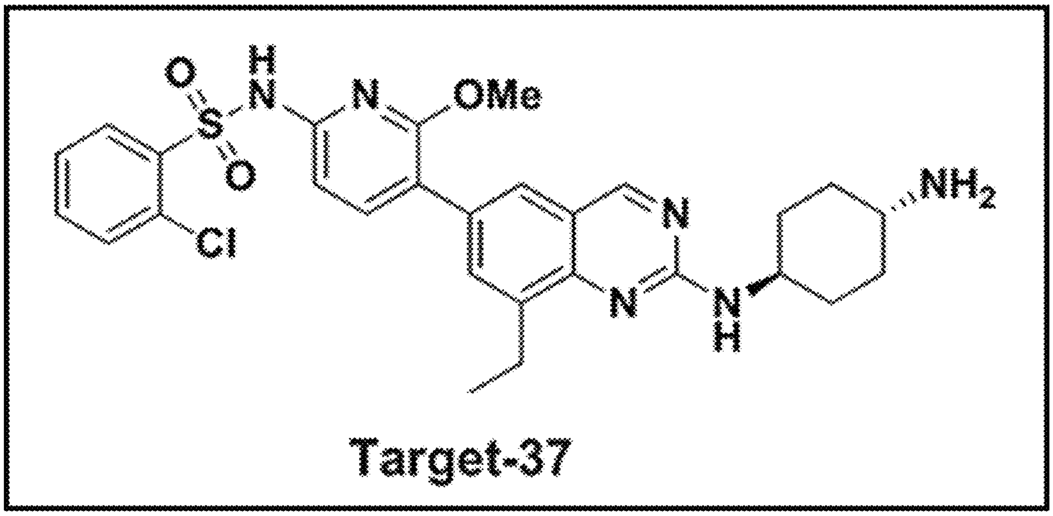
FIG. 7. KIRA and PAIR comparison.
Figure 7:
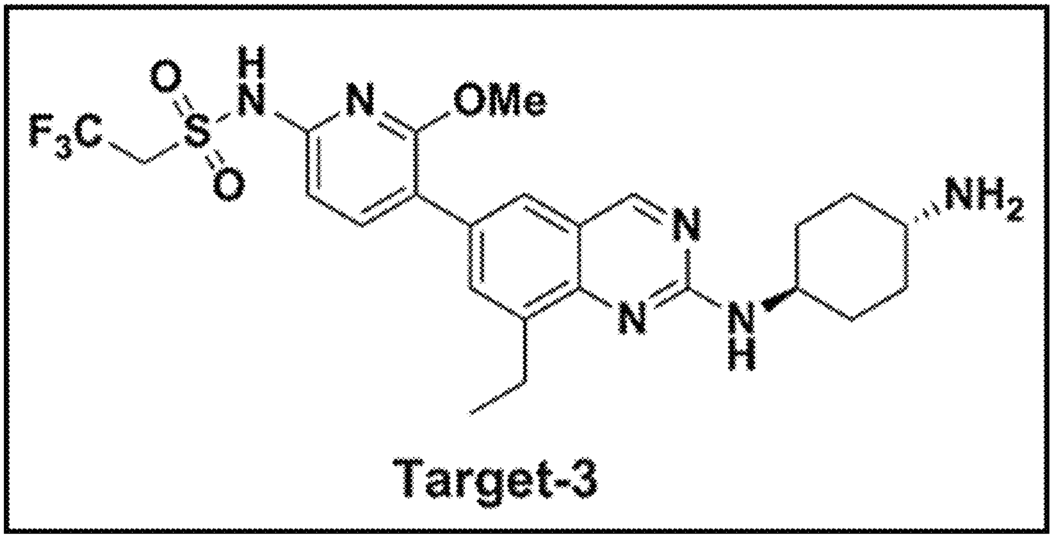
Figure 8:
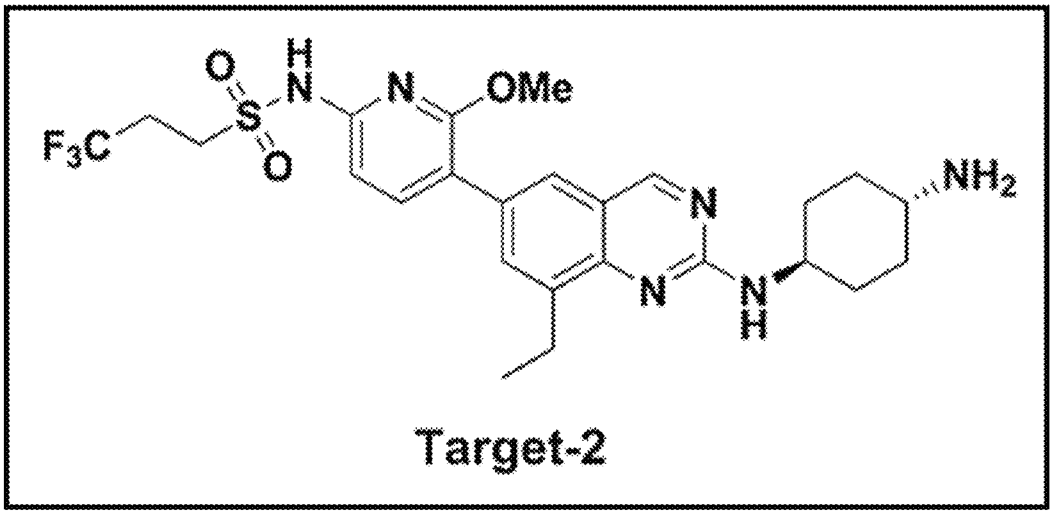
FIG. 8. Selected PAIR compounds.
Figure 8:
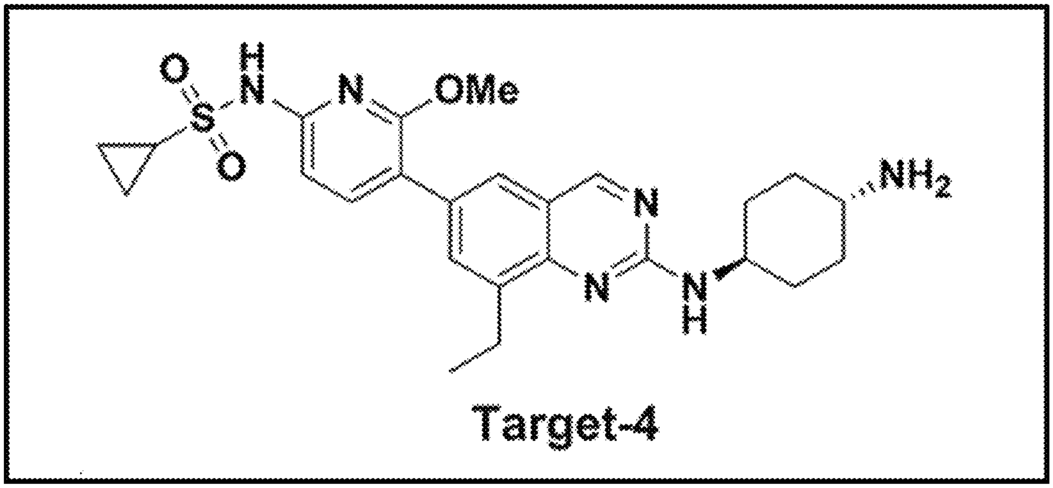
Figure 9A:
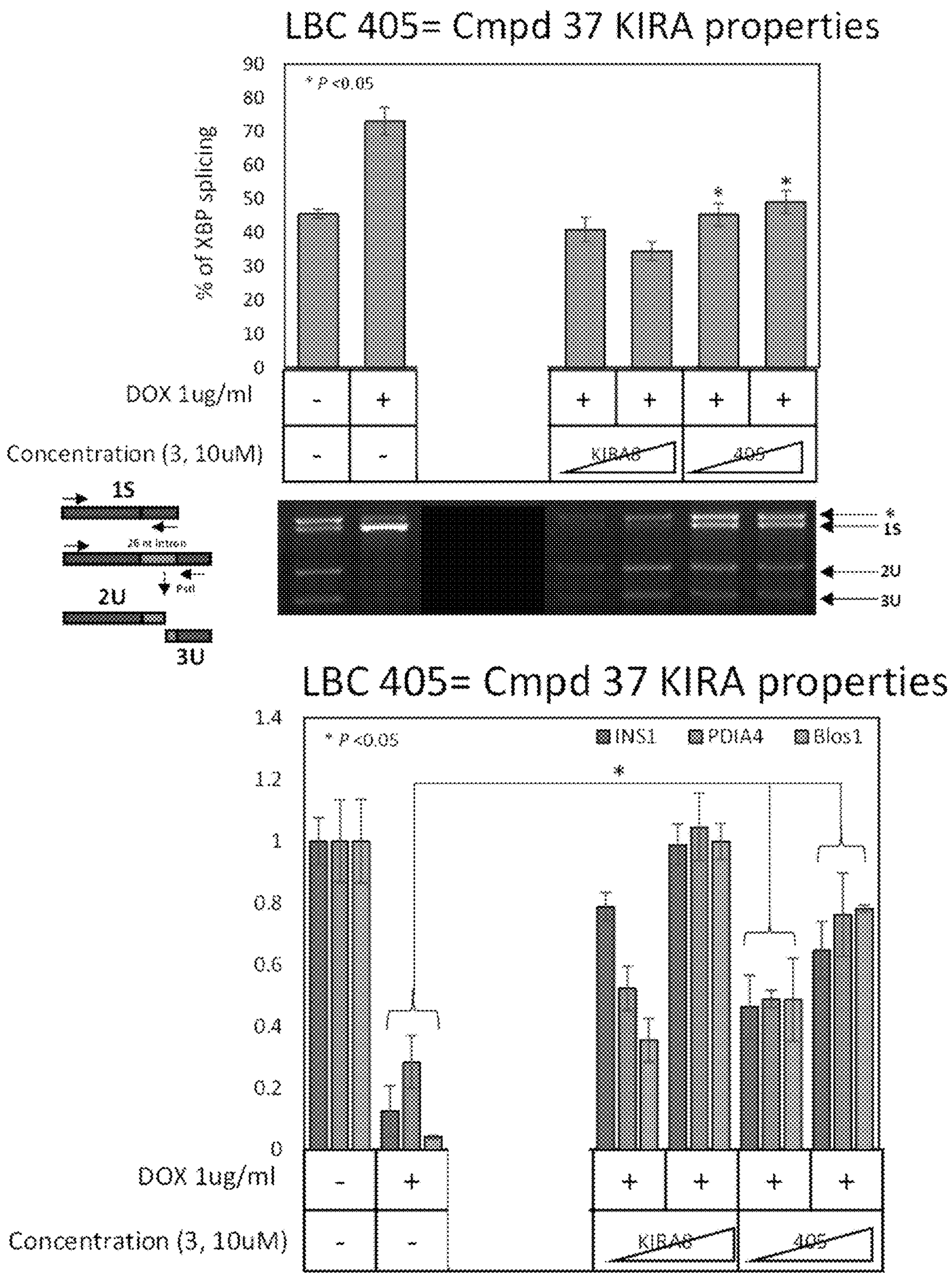
FIGS. 9A-9D. Selected PATR compounds cellular assay compared to KIRA8. XBP1 splicing: INS-1 cells expressing IRE1α (WT) indicated concentrations (3, 10 μM) of LBC-405 (FIG. 9A), 407 (FIG. 9B), 408 (FIG. 9C), and KIRA8 (FIG. 9D)) for 1 hr and then with or without Dox (1 μg/mL) for 4 hrs. Ethidium bromide-stained agarose gel of XBP1 cDNA amplicons from PCR. The ratio of spliced over (spliced+unspliced) amplicons 1S/(1S+2U+3U)—is reported as "% spliced XBP1 amplicons" in bar graph. Three independent biological samples were used. Data are shown as mean±SE. *$p<0.05$ significant. Real-time PCR for RIDD target quantification: cDNA was prepared from INS-1 cells expressing IRE1α or without Dox (5 ng/mL) for 24 hrs. Quantitative PCR for Ins1, PDIA4, Blos1 expression shown two independent biological and experiments perform in quadruplet. Data are shown as mean±±SE. *$p<0.05$ significant.
Figure 9B:
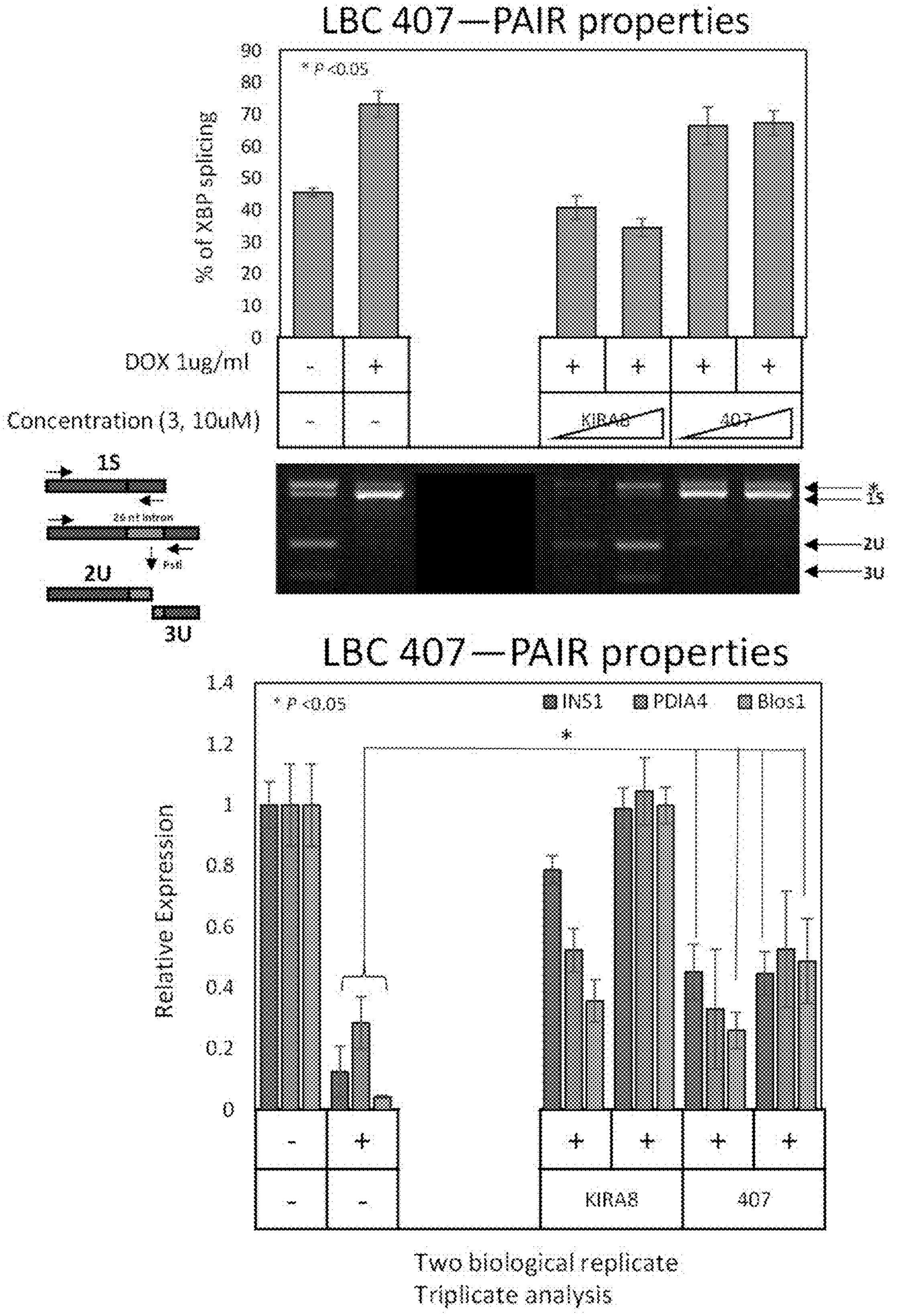
Figure 9C:
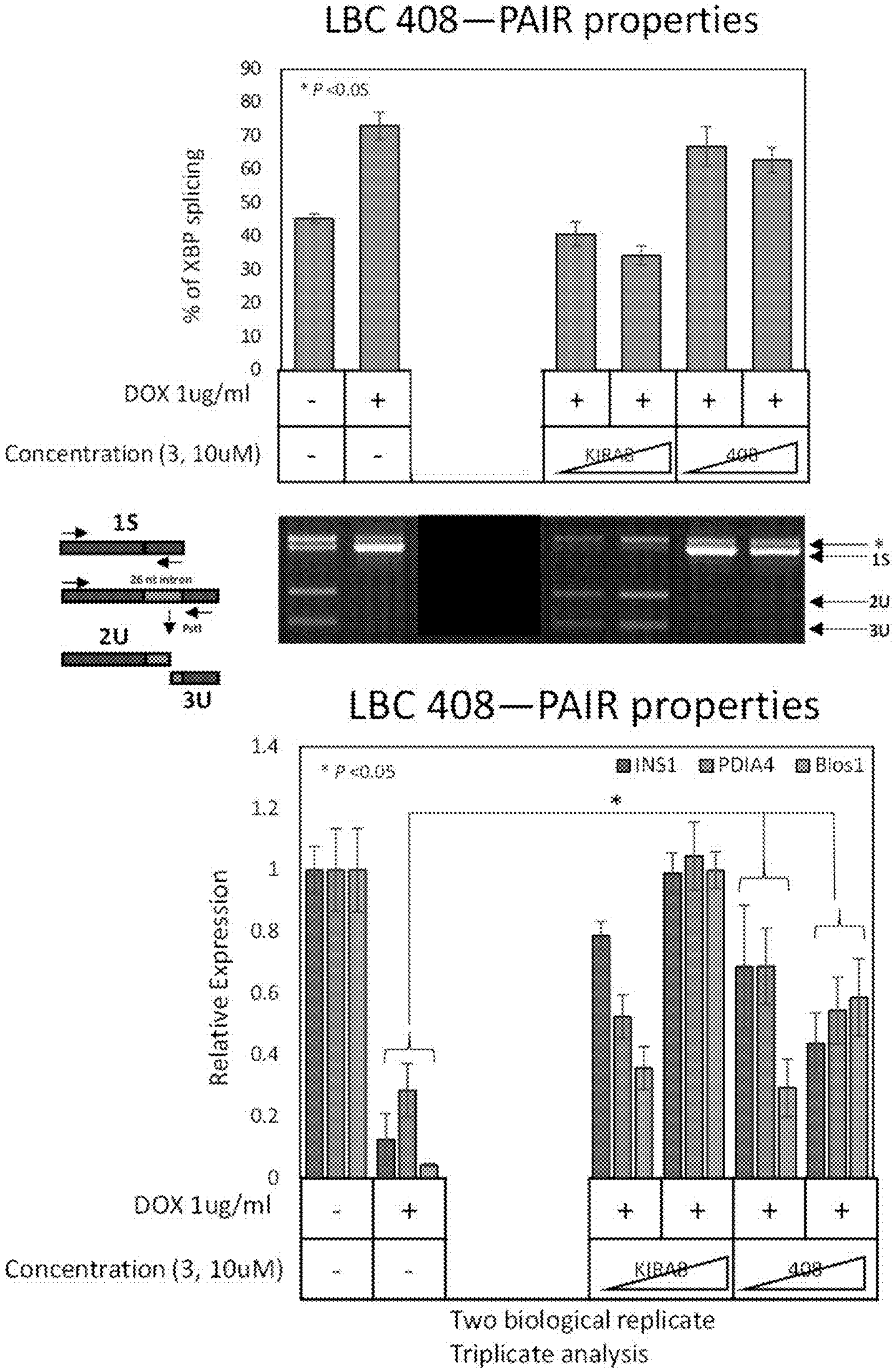
Figure 9D:
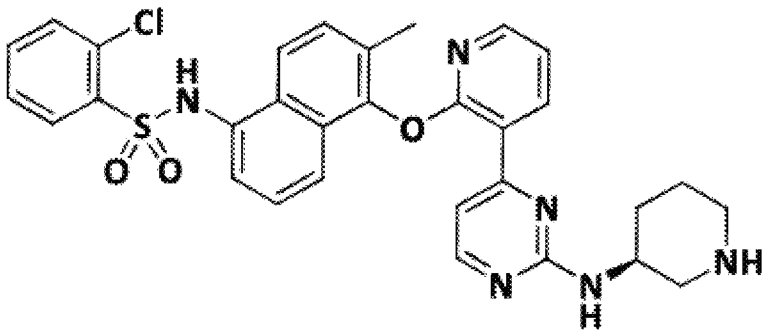

Using this assay, we found that IRE1*, which is basally autophosphorylated on its activation loop, demonstrated a dimerization affinity in the high nanomolar range ($K_{dimer}$=140 nM). A quantitatively dephosphorylated IRE1α* construct (dpIRE1α*) (FIG. 3) was also capable of forming RNase active dimers but with a much lower dimerization affinity ($K_{dimer}$>4 μM), showing that activation loop phosphorylation strengthens back-to-back dimer formation by over 25-fold (FIG. 1C). ATP-competitive ligands that allosterically promote IRE1α's RNase activity also increase the dimerization affinity of the kinase/RNase domains of IRE1α. We found that the $K_{dimer}$ of dpIRE1α* was over 80-fold lower when its kinase domain was complexed to the ATP-competitive ligands AT9283 or AZD7762 (FIG. 1D, FIG. 4). AT9283 and AZD7762 also led to a similar fold increase in the dimerization affinity of RE1α*, demonstrating that ATP-binding ligands are capable of further increasing the already enhanced ability of activation loop-phosphorylated IRE1α to form dimers (FIG. 1E, FIG. 5).

Next, we tested how a class of ATP-binding site ligands-called kinase inhibiting RNase attenuators (KIRAs)—that inactivate IRE1α's RNase activity through the kinase domain affect dimerization affinity. We found that IRE1α* was unable to form RNase active dimers at any concentration tested when bound to the highly potent KIRA, KIRA8, or even to lower affinity KIRAs (FIG. 1E). Thus, it appears that KIRAs stabilize an ATP-binding site conformation that completely disrupts the back-to-back dimer interface of IRE1α. Thus, KIRA-bound IRE1α appears to be locked in an RNase inactive monomeric state in vitro and in cells.

Example 2: Partial Antagonists of IRE1α's RNase Activity

We speculated that it should be possible to identify ATP-competitive ligands that only intermediately weaken the dimerization affinity of IRE1α, and hence preserve some RNase outputs, rather than enforce a fully monomeric state with completely crippled RNase activity, like KIRAs do.

Example 3

Ire1 mediates a simple, linear UPR pathway through splicing of Hac1 mRNA in *S. cerevisiae* PMID: 9348528, PMID: 8898193, and appears to exclusively promote RIDD in *S. pombe* PMID: 23066505. In both these well studied models, Ire1 outputs restore ER secretory homeostasis. In contrast to these lower eukaryotes, multicellular eukaryotes—especially mammals—have evolved an expanded number of UPR outputs, and other UPR sensor/effectors; yet the widely-expressed IRE1α ortholog has preserved both non-conventional splicing features (through frameshift splicing of XBP1 mRNA) and RIDD PMID: 19651891, PMID: 19665977. The first studies to bifurcate these two outputs used allele-sensitized versions of IRE1α, which as with yeast Ire1 PMID: 14564015, can be activated through the provision of a designer kinase inhibitor—1NM-PP1-fulfills a "co-factor" requirement in the enlarged kinase domain nucleotide-binding pocket (I642G) to activate from a distance (allosterically) the XBP1 mRNA splicing feature of the RNase, while averting RIDD PMID: 18035051, 19651891, 19665977.

Furthermore, the scope of biological outputs of XBP1 mRNA and RIDD have been widely studied, but are still largely debated. The requirement of XBP1 transcription factor in de novo differentiation of progenitor cells to mature professional terminally differentiated cells was first discovered in the B-cell to plasma cell transition PMID: 11460154; IRE1α-mediated splicing of XBP1 mRNA is critical for this transition and for other examples in ontogeny PMID: 11780124. The role of RIDD has been studied in many contexts. In our previous studies, the pharmacological inhibition of RIDD using KIRAs prevents apoptosis. At maximal occupancy, KIRAs monomerize IRE1α and thereby quench XBP1 splicing. Here, we are developing ATP-competitive ligands—PAIRs—that achieve an intermediate dimerization state of the kinase/RNase domain of IRE1α, which allows inhibition of RIDD while preserving XBP1 mRNA splicing. We achieve this intermediate dimerization state by introducing substituents into PAIRs that only partially displace the helix αC of IRE1α from an active conformation. The helix αCs of protein kinases are dynamic structural features that are often allosterically coupled to distal binding interfaces. In most cases the conformation of helix αC has been defined as two conformational extremes; an active "in" form or an inactive "out" conformation. PAIRs stabilize an intermediate conformational state between these two extremes, which appears to mimic unphosphorylated apo IRE1α based on the similar $K_{dimer}$s of PAIR-bound IRE1α and unphosphorylated apo IRE1α. As the helix αCs of many kinases are components of binding interfaces, it is likely that similar rheostatic control can be engineered into ATP-competitive inhibitors that target other kinases The capability to bifurcate the two distinct cytosolic RNase outputs of IRE1α with a small molecule opens up the potential to drug the UPR in more nuanced ways. Thus, we compared KIRAs and PAIRs here in two distinct-even opposite-cell fate outcome settings: one destructive (IRE1α over-expression leasing to apoptosis), the other constructive (B-cell differentiation). The dismantling of an ER-stressed cell during its commitment to entering mitochondrial apoptosis has been studied by us and others. We have proposed that hyperactivation of IRE1α RNase and reduction of many ER-localized mRNAs is a sine quo none of this cell death entry step. In many biological contexts, we have reported this RIDD signature preceding entry into apoptosis; this set of events is hastened in INS-1 insulinoma cell lines (derived from an insulin-producing β-cell tumor) that force RIDD (on top of XBP1 mRNA splicing) through mere overexpression of IRE1α. If RIDD leads deterministically to apoptosis, without regard to XBP1 outputs, PAIRs should be non-inferior to KIRAs in these cellular systems.

In summary, we propose that the ability to segregate IRE1α's synthetic UPR outputs (i.e, XBP1 transcription factor-driven) from its destructive RIDD outputs through applying PAIRs as comparators to monomerizing KIRAs will reveal the scope and diversity of distinct UPR biological outputs. Finally, such compounds may have the benefit of navigating a wider therapeutic window than existing IRE1α kinase inhibitors (such as KIRAs or the less-selective RNase inhibitors that work through covalent modification). The unique ability of PAIRs to preserve adaptive XBP1 splicing at full target engagement may thereby achieve a more desirable therapeutic modulation of IRE1α in myriad diseases caused by ER stress-induced premature cell death Target Compounds:

Target-2

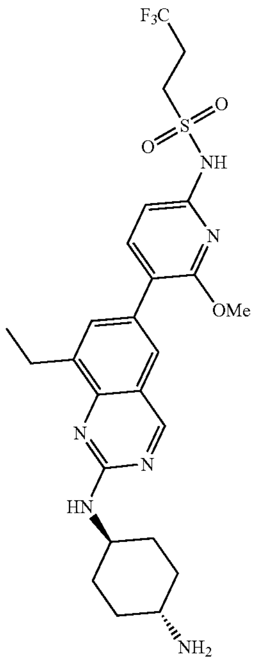

-continued

Target-3

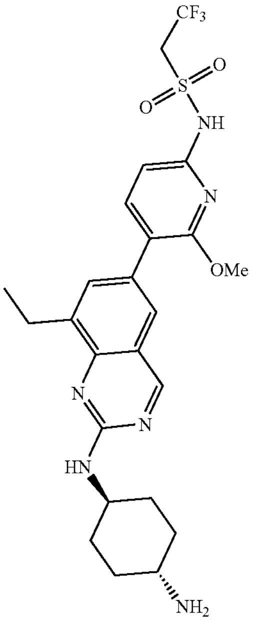

Target-4

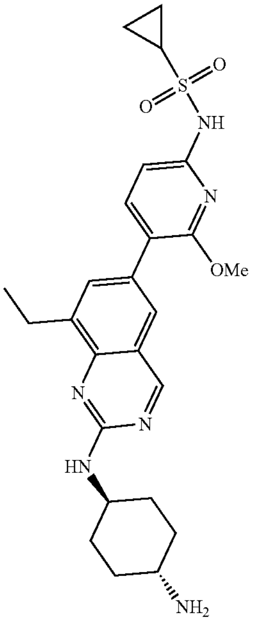

Synthetic Scheme for Target-2:

Synthetic Scheme for Target-2

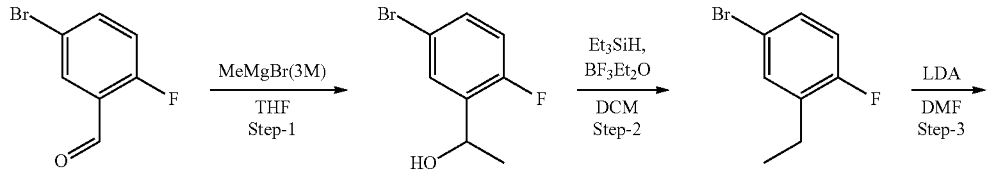

1

2

-continued
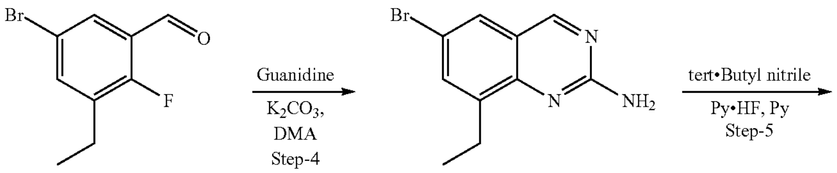
4 5
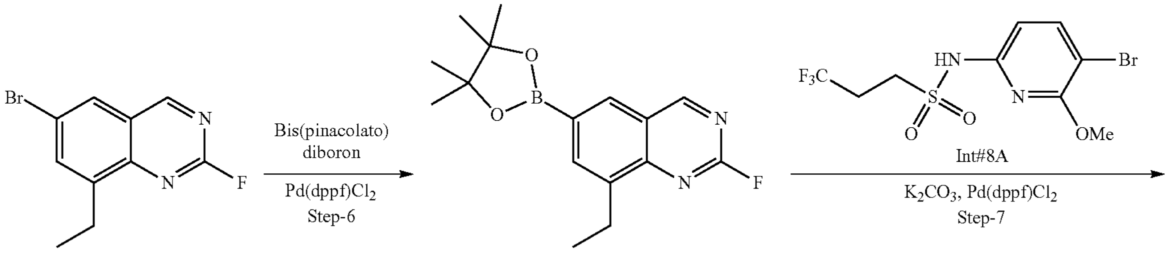
6 Int#7
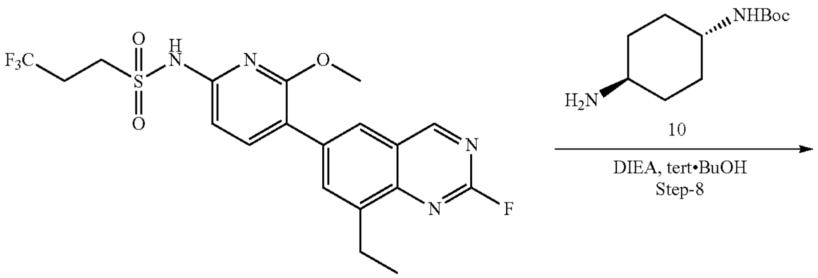
9A
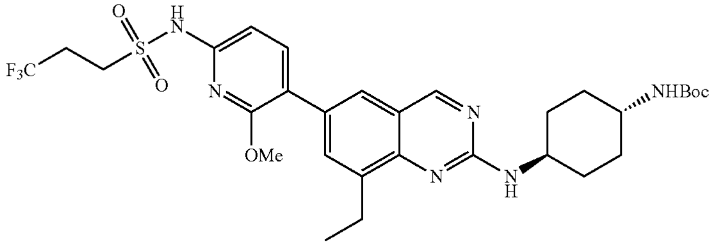
11A
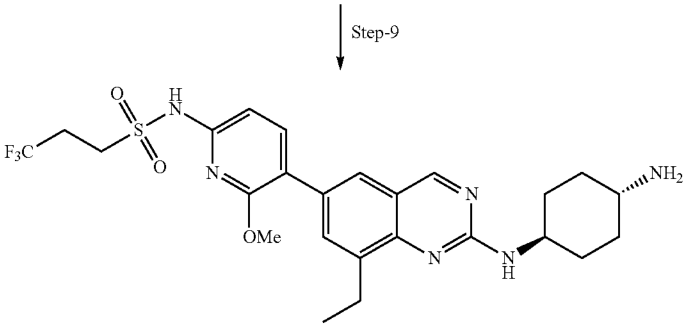
Target-2
Int#8A:
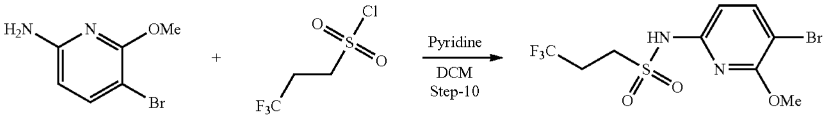
12 13A Int#8A Step-1: Synthesis of 1-(5-bromo-2-fluorophenyl) ethan-1-ol (2)

To a stirred solution of 5-Bromo-2-fluorobenzaldehyde (5 g, 0.0246 mol) in THE (50 mL) was added $CH_3MgBr$ (3M) (9 mL, 0.027 mol) at 0° C. for a period of 30 min. The resulting reaction mixture was stirred for 3 h at the same temperature. The reaction mixture was then treated with saturated $NH_4Cl$ (45 mL) at 0° C., and extracted with EtOAc (30 mL×3). The combined organic layer was washed with brine (3*20 mL), and the separated organic layer was dried over anhydrous $Na_2SO_4$, filtered and concentrated under reduced pressure to dryness. The residue was purified from column chromatography eluting with ethyl acetate/hexane (5:95) in giving Compound-2 as a colorless liquid. Yield: 4 g (74.6%); TLC system: EtOAc:Hexane [5:95]; $R_f$: 0.3. $^1H$ NMR (400 MHz, DMSO-$d_6$): δ 7.64-7.61 (m, 1H), 7.48-7.44 (m, 1H), 7.16-7.11 (m, 1H), 5.45 (d, 1H), 4.97-4.91 (m, 1H), 1.32 (d, 3H).

Step-2: Synthesis of 4-bromo-2-ethyl-1-fluorobenzene (3)

To a stirred solution of 1-(5-bromo-2-fluorophenyl) ethanol (14 g, 0.0642 mol) in DCM (140 mL) was added Triethyl silane (20.5 mL, 0.128 mol) at room temperature. After being stirred for 15 min at 0° C., $BF_3 \cdot Et_2O$ (15.9 mL, 0.128 mol) was added. Then the mixture was allowed to stir at RT for 18 h. The reaction mixture was quenched by addition of sat·$NaHCO_3$ (70 mL) at 0° C., stirred for 30 min and extracted with DCM (2*50 mL). The combined organic layers were washed with brine (2*30 mL), dried over anhydrous $Na_2SO_4$, filtered and concentrated under reduced pressure to dryness. The crude residue was further purified by silica-gel column chromatography eluting with hexane giving Compound-3 as a colorless liquid. Yield: 6 g (46.2%); TLC system: Hexane [100]; $R_f$: 0.7. $^1H$ NMR (400 MHz, $CDCl_3$): δ 7.35-7.30 (m, 1H), 7.27-7.$2_3$ (m, 1H), 6.88 (t, J=9.2 Hz, 1H), 2.63 (q, J=7.6 Hz, 15.2 Hz, 2H), 1.24-1.19 (t, J=7.6 Hz, 3H).

Step-3: Synthesis of 5-bromo-3-ethyl-2-fluorobenzaldehyde (4)

To a stirred solution of 4-Bromo-2-ethyl-1-fluorobenzene (10 gr, 0.050 mol) in THE (100 mL) at −78° C. was added LDA (22.2 mL, 2M in THF, 0.0445 mol) slowly over a period of 30 min, followed by stirring for 1 h. Then DMF (3.25 mL, 0.0445 mol) was added and stirring continued for another 1 h. The mixture was then treated with a sat. $NH_4Cl$ (90 mL) solution at −78° C. and extracted with EtOAc (2*60 mL). The combined organic layers were washed with brine (2*40 mL), dried over anhydrous $Na_2SO_4$, filtered and concentrated under reduced pressure to dryness. The crude residue was further purified by silica-gel column chromatography eluting with ethyl acetate/hexane (2:98) to give Compound-4 as a colorless liquid. Yield: 6.6 g (58.4%); TLC system: EtOAc:Hexane [5:95]; $R_f$: 0.4. $^1H$ NMR (400 MHz, $CDCl_3$): δ 10.29 (s, 1H), 7.81-7.79 (m, 1H), 7.60-7.56 (m, 1H), 2.71 (q, J=7.6 Hz, 14.8 Hz, 2H), 1.29-1.24 (t, J=7.6 Hz, 3H).

Step-4: Synthesis of 6-bromo-8-ethylquinazolin-2-amine (5)

To a stirred solution of Guanidine carbonate (3.16 g, 0.0260 mol) in DMA (35 mL) was added $K_2CO_3$ (7.2 gr, 0.052 mol) followed by 5-bromo-3-ethyl-2-fluorobenzaldehyde (Compound-4) (4.0 g, 0.017 mol; in 5 mL of DMA solution). Then the reaction mixture was heated and stirred at 160° C. for 2 h. After completion of the reaction by TLC, the mixture was concentrated to dryness under reduced pressure. The obtained crude residue was further purified from silica-gel column chromatography using ethyl acetate/hexane (20:80) as an eluent to obtain Compound-5 as a yellowish colored solid. Yield: 1.3 g (29.8%); TLC system: EtOAc:Hexane [20:80]; $R_f$: 0.3. $^1H$ NMR (400 MHz, DMSO-$d_6$): δ 9.05 (s, 1H), 7.87 (d, 1H), 7.62 (d, 1H), 6.95 (s, 2H), 2.94 (q, J=7.6 Hz, 15.2 Hz, 2H), 1.22 (t, J=7.6 Hz, 3H).

Step-5: Synthesis of 6-bromo-8-ethyl-2-fluoroquinazoline (6)

To a stirred solution of 6-bromo-8-ethylquinazolin-2-amine (compound-5) (1.2 g, 0.0047 mol) in Pyridine (12 mL) at −40° C. was added HF-Py (24 mL). After 15 min., tert-butyl nitrite (1.14 mL, 0.0095 mol) was added at the same temperature over 15 min., and the reaction was allowed to stir at room temperature for 1 h. The reaction mixture was then poured in ice cold water and the pH was adjusted to 7 using sat. $NaHCO_3$ solution and extracted with EtOAc (2*40 mL). The combined organic layers were washed with brine (3*20 mL), dried over anhydrous $Na_2SO_4$, filtered and concentrated to dryness. The crude residue was further purified from silica-gel column chromatography using ethyl acetate/hexane (5:95) as an eluent to obtain Compound-6 as a yellowish solid. Yield: 400 mg (33%); TLC system: EtOAc:Hexane [20:80]; $R_f$: 0.7. $^1H$ NMR (400 MHz, $CDCl_3$): δ 9.25 (d, 1H), 7.99 (d, 1H), 7.86 (d, 1H), 3.174 (q, J=7.6 Hz, J=15.2 Hz, 2H), 1.38-1.34 (t, J=7.6 Hz, 3H).

Step-6: Synthesis of 8-ethyl-2-fluoro-6-(4,4,5,5-tetramethyl-1,3,2-dioxaborolan-2-yl) quinazoline (7)

A solution of 6-bromo-8-ethyl-2-fluoroquinazoline (6) (750 mg, 0.0029 mol), KOAc (434 mg, 0.0044 mol), Bis (pinacolato diborane) (900 mg, 0.0035 mol), $Pd(dppf)Cl_2$ (236 mg, 0.00029 mol) in 1,4-dioxane (15 mL) was stirred at 90° C. for 18 h under nitrogen atmosphere. The reaction mixture was filtered through a celite pad and washed with EtOAc (25 mL), and the filtrate was concentrated under reduced pressure to dryness. The crude residue (Compound-7, black colored solid) was directly used in the next step without any further purification. Yield: 1 g (crude); TLC system: EtOAc:Hexane (30:70); $R_f$: 0.4. $^1H$ NMR (400 MHz, DMSO-$d_6$): δ 11.5 (brs, 1H), 9.01 (brs, 1H), 8.28 (d, 1H), 7.71 (d, 1H), 7.67-7.63 (m, 3H), 7.60-7.56 (m, 2H), 7.26 (brs, 1H), 6.75 (d, 1H), 6.61 (d, 1H), 3.80-3.70 (m, 1H), 3.48 (s, 3H), 3.28-3.20 (m, 1H), 2.94 (q, J=7.2 Hz, 14.8 Hz, 2H), 2.07-2.02 (m, 2H), 1.83-1.78 (m, 2H), 1.38 (s, 9H), 1.33-1.$2_3$ (m, 4H), 1.16 (t, J=8 Hz, 3H).

Step-7: Synthesis of N-(5-(8-ethyl-2-fluoroquinazolin-6-yl)-6-methoxypyridin-2-yl)-3,3,3-trifluoropropane-1-sulfonamide (9A)

To a stirred solution of 8-ethyl-2-fluoro-6-(4,4,5,5-tetramethyl-1,3,2-dioxaborolan-2-yl) quinazoline (Int#7) (275 mg, 0.910 mmol) and Int#8A (265 mg, 0.728 mmol) in 1,4-dioxane (8 mL) were added 2M solution of $K_2CO_3$ (1.86 mL, 3.73 mmol) and $Pd(dppf)Cl_2$ (75 mg 0.091 mmol). The mixture was evacuated and back filled with nitrogen, heated at 90° C. and stirred for 18 h. The reaction mixture was filtered through a pad of celite and washed with EtOAc (30 mL). The filtrate was concentrated to dryness, and the crude residue was further purified from basic silica-gel column chromatography using ethyl acetate/hexane (20:80) as an eluent to obtain Compound-9A as an off white solid. LC-MS purity: 70.94%; Mass (m/z): 459.1 $[M+H]^+$; Yield: 220 mg (52.7%); TLC system: EtOAc:Hexane [30:70]; $R_f$: 0.3.

Step-8: Synthesis of tert-butyl ((1r,4r)-4-((8-ethyl-6-(2-methoxy-6-((3,3,3-trifluoropropyl) sulfonamido) pyridin-3-yl) quinazolin-2-yl) amino) cyclohexyl) carbamate (11A)

To a stirred solution of Compound-(9A) (220 mg, 0.480 mmol) in n-butanol (8 mL) was added N,N-diisopropylethylamine (0.60 mL, 3.5 mmol) followed by tert-butyl ((1r, 4r)-4-aminocyclohexyl) carbamate (422 mg, 1.969 mmol). The mixture was heated at 100° C. for 18 h with stirring. The reaction mixture was concentrated under reduced pressure to dryness, and the crude residue was purified by basic silica-gel column chromatography using methanol/dichloro methane (3:97) as an eluent to obtain Compound-11A as an off-white solid. LC-MS purity: 63.92%; Mass (m/z): 651.2 $[M-H]^+$; Yield: 120 mg (38.3%); TLC system: EtOAc: Hexane [30:70]; $R_f$: 0.2.

Step-9: Synthesis of N-(5-(2-(((1r,4r)-4-aminocyclohexyl) amino)-8-ethylquinazolin-6-yl)-6-methoxypyridin-2-yl)-3,3,3-trifluoropropane-1-sulfonamide (Target-2)

To a stirred solution of tert-butyl ((1R,4R)-4-((8-ethyl-6-(2-methoxy-6-((3,3,3-trifluoropropyl) sulfonamido) pyridin-3-yl) quinazolin-2-yl) amino) cyclohexyl) carbamate (120 mg) in 1,4-dioxane (1 mL) was added 4M dioxane in HCl (1.5 mL). The mixture was stirred at room temperature for 2 h, concentrated on rotavap under reduced pressure and triturated with $Et_2O$. The crude material was further purified by Combi-flash purification. The collected fractions were lyophilized to obtain Target-2 as a yellow solid.

LC-MS purity: 96.57%; Mass (m/z): 553.4 $[M+H]^+$; Yield: 30 mg (29.7%); TLC system: MeOH:DCM [20:80]; $R_f$: 0.2. $^1H$ NMR (400 MHz, DMSO-$d_6$): δ 11.01 (brs, 1H), 9.09 (brs, 1H), 8.18-7.90 (m, 4H), 7.84-7.78 (m, 2H), 7.42-7.37 (m, 1H), 6.67 (d, 1H), 3.93-3.88 (m, 3H), 3.85 (s, 3H), 3.06-3.00 (m, 3H), 2.86-2.79 (m, 2H), 2.15-2.00 (m, 4H), 1.60-1.40 (m, 4H), 1.28 (t, J=7.6 Hz, 3H).

Step-10: Synthesis of N-(5-bromo-6-methoxypyridin-2-yl)-3,3,3-trifluoropropane-1-sulfonamide (Int#8A)

To a stirred solution of 5-bromo-6-methoxypyridin-2-amine (compound-11) (300 mg, 1.485 mmol) in pyridine (2 mL) was added 3,3,3-trifluoropropane-1-sulfonyl chloride (350 mg, 1.8 mmol) slowly for about 5 min. The reaction mixture was stirred at room temperature for 18 h and then concentrated to dryness under reduced pressure. The crude residue was purified by silica-gel column chromatography using ethyl acetate/hexane (20:80) as an eluent to obtain Int#8A as a brown solid. LC-MS purity: 99.18%; Mass (m/z): 362.8$[M+H]^+$; Yield: 320 mg (59.5%); TLC system: EtOAc:Hexane [20:80]; $R_f$: 0.3. $^1H$ NMR (400 MHz, $CDCl_3$): δ 7.77 (d, 1H), 6.53 (d, 1H), 3.96 (s, 3H), 3.70-3.66 (m, 2H), 2.75-2.68 (m, 2H).

Synthetic Scheme for Target-4:

Synthetic Scheme for Target-4

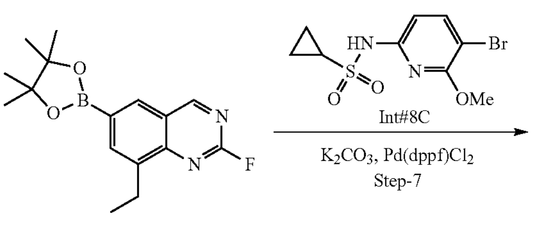

Int#7

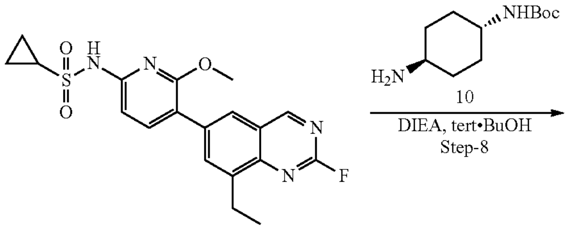

9C

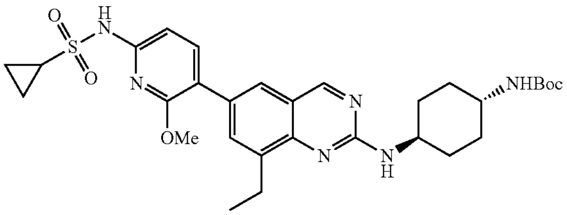

11C

Step-9

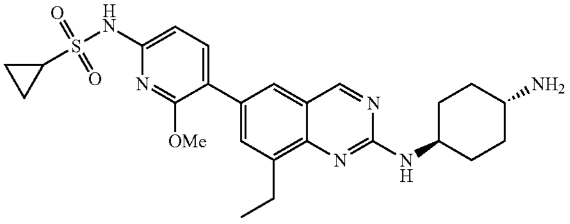

Target-4

Int#8C:

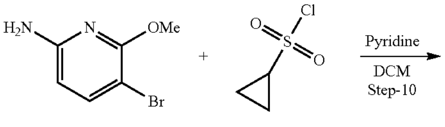

12

13C

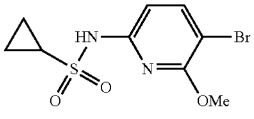

Int#8C

Step-7: Synthesis of N-(5-(8-ethyl-2-fluoroquinazolin-6-yl)-6-methoxypyridin-2-yl) cyclopropane sulfonamide (9C)

To a stirred solution of 8-ethyl-2-fluoro-6-(4,4,5,5-tetramethyl-1,3,2-dioxaborolan-2-yl) quinazoline (Int#7) (300 mg, 1.0 mmol) in dioxane (8 mL) were added Compound-8C (243 mg, 0.794 mmol), 2M solution of $K_2CO_3$ (2 mL, 4.072 mmol) and Pd(dppf)$Cl_2$ (81 mg 0.0993 mmol). The mixture was evacuated and back filled with nitrogen, then heated to 90° C. and stirred for 18 h. After completion of the reaction by TLC, the reaction mixture was filtered through a pad of celite and washed with EtOAc. The filtrate was concentrated to dryness under reduced pressure. The crude residue was purified by basic silicagel column chromatography using ethyl acetate/hexane (20:80) as an eluent to obtain Compound-9C as a yellow solid. LC-MS purity: 42.67%; Mass (m/z): 403.0 $[M+H]^+$; Yield: 290 mg (72.6%); TLC system: EtOAc:Hexane [30:70]; $R_f$: 0.3.

Step-8: Synthesis of tert-butyl ((1r,4r)-4-((6-(6-(cyclopropanesulfonamido)-2-methoxypyridin-3-yl)-8-ethylquinazolin-2-yl) amino) cyclohexyl) carbamate (11C)

To a stirred solution of compound-(9C) (290 mg, 0.721 mmol) in n-butanol (8 mL) were added DIPEA (0.90 mL, 5.194 mmol) followed by tert-butyl ((1r,4r)-4-aminocyclohexyl) carbamate (632 mg, 2.957 mmol). Then the reaction mixture was heated to 100° C. and stirred for 18 h. After completion of the reaction by TLC, the reaction mixture was concentrated to dryness by rotavap. The crude residue was further purified by basic silica-gel column chromatography using methanol/dichloro methane (3:97) as an eluent to obtain Compound-11C as a brown solid.

LC-MS purity: 60.29%; Mass (m/z): 597.4 $[M+H]^+$; Yield: 140 mg (32.6%); TLC system: EtOAc:Hexane [30:70]; $R_f$: 0.2.

Step-9: Synthesis of N-(5-(2-(((1r,4r)-4-aminocyclohexyl) amino)-8-ethylquinazolin-6-yl)-6-methoxypyridin-2-yl) cyclopropane sulfonamide (Target-4)

To a stirred solution of tert-butyl ((1r,4r)-4-((6-(6-(cyclopropanesulfonamido)-2-methoxypyridin-3-yl)-8-ethylquinazolin-2-yl) amino) cyclohexyl) carbamate (140 mg) in 1,4-dioxane (1 mL) was added 4M-HCl in dioxane (1.5 mL) and stirred the reaction mixture at room temperature for 2 h. After completion of the reaction by TLC, the reaction mixture was directly concentrated under reduced pressure, and washed with $Et_2O$ (2 mL). The crude residue was purified by reverse phase purification using Combi-Flash. The collected fractions were lyophilized to obtain Target-4 as a yellow solid. LC-MS purity: 97.53%; Mass (m/z): 497.4 $[M+H]^+$; Yield: 35 mg (30.17%); TLC system: MeOH:DCM [20:80]; $R_f$: 0.2. $^1H$ NMR (400 MHz, DMSO-$d_6$): δ 10.67 (brs, 1H), 9.55 (brs, 1H), 9.10 (brs, 1H), 8.14-8.07 (m, 4H), 7.85-7.75 (m, 2H), 6.68 (d, 1H), 4.10-4.00 (m, 1H), 3.92 (s, 3H), 3.24-3.17 (m, 1H), 3.05-3.00 (m, 3H), 2.17-2.00 (m, 4H), 1.60-1.40 (m, 4H), 1.28 (t, J=7.6 Hz, 3H), 1.13-1.07 (m, 4H).

Step-10: Synthesis of N-(5-bromo-6-methoxypyridin-2-yl) cyclopropane sulfonamide (Int#8C)

To a stirred solution of 5-bromo-6-methoxypyridin-2-amine (Compound-11) (300 mg, 1.5 mmol) in pyridine (2 mL) was added cyclopropane sulfonyl chloride (250 mg, 1.782 mmol). and stirred the mixture at room temperature for 18 h. The reaction mixture was then concentrated and the resulted crude was further purified from basic silica-gel column chromatography using ethyl acetate/hexane (20:80) as an eluent to obtain Int#8C as a brown solid. LC-MS purity: 74.25%; Mass (m/z): 308.8 $[M+2H]^+$; Yield: 300 mg (66%); TLC system: EtOAc:Hexane [20:80]; $R_f$: 0.3. $^1H$ NMR (400 MHz, $CDCl_3$): δ 7.74 (d, 1H), 6.77 (d, 1H), 3.96 (s, 3H), 2.75-2.71 (m, 1H), 1.32-1.28 (m, 2H), 1.08-1.06 (m, 2H).

Synthetic Scheme for Target-3:

Synthetic Scheme for Target-3

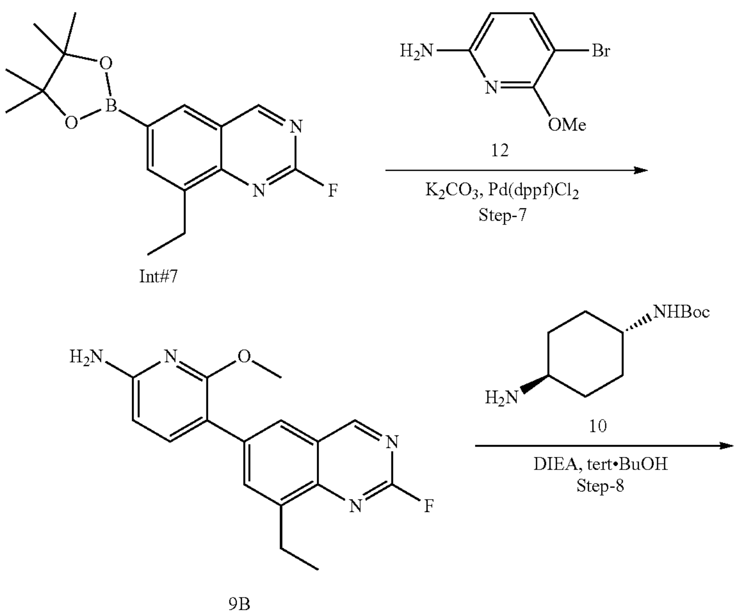

9B

-continued

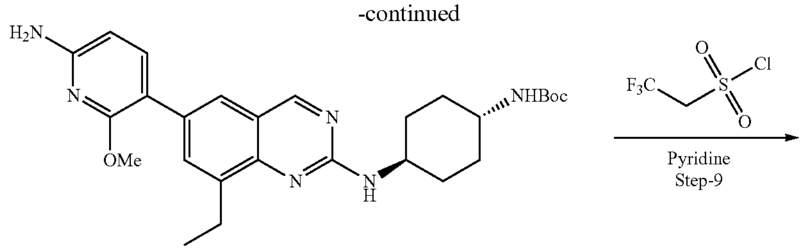

11B

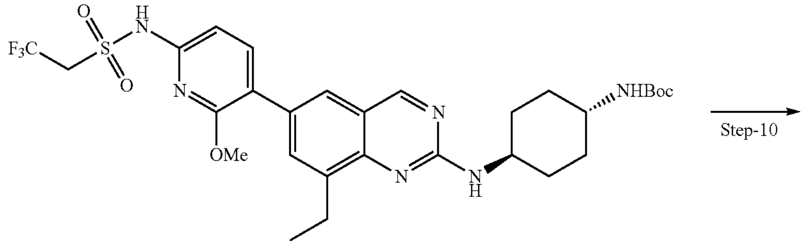

12B

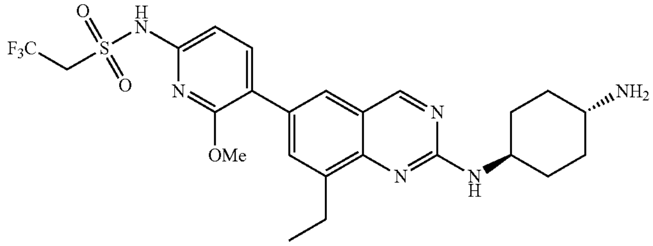

Target-3

Step-7: Synthesis of 5-(8-ethyl-2-fluoroquinazolin-6-yl)-6-methoxypyridin-2-amine (9B)

To a stirred solution of 8-ethyl-2-fluoro-6-(4,4,5,5-tetramethyl-1,3,2-dioxaborolan-2-yl) quinazoline (Int#7) (1 g, 0.0033 mol) in 1,4-dioxane (8 mL) were added 5-bromo-6-methoxypyridin-2-amine (470 mg, 0.00231 mol) and a 2M solution of $K_2CO_3$ (3.3 mL, 0.0066 mol) and Pd(dppf)$Cl_2$ (269 mg 0.00033 mol). The reaction mixture was evacuated and back filled with nitrogen, then heated to 90° C. for 18 h with stirring. The reaction mixture was then filtered through a pad of celite and washed with EtOAc. The filtrate was concentrated under reduced pressure and the crude material was purified by basic silica-gel column chromatography using ethyl acetate/hexane (20:80) as an eluent to obtain Compound-9B as a yellow solid. LC-MS purity: 93.36%; Mass (m/z): 299.0 $[M+H]^+$; Yield: 200 mg (20.2%); TLC system: EtOAc:Hexane [30:70]; $R_f$: 0.2. $^1H$ NMR (400 MHz, DMSO-d6): δ 9.60 (d, 1H), 8.13-8.08 (m, 2H), 7.60 (d, 1H), 6.20 (d, 1H), 6.17 (s, 2H), 3.84 (s, 3H), 3.07 (q, J=7.2 Hz, 14.8 Hz, 2H), 1.29 (t, J=7.6 Hz, 3H).

Step-8: Synthesis of tert-butyl ((1R,4R)-4-((6-(6-amino-2-methoxypyridin-3-yl)-8-ethylquinazolin-2-yl) amino) cyclohexyl) carbamate (11B)

To a stirred solution of Compound-(9B) (200 mg, 0.7 mmol), DIPEA (0.50 mL, 2.7 mmol) in n-butanol (4 mL) was added tert-butyl ((1r,4r)-4-aminocyclohexyl) carbamate (430 mg, 2.01 mmol). The reaction was heated to 100° C., stirred for 18 h, and concentrated to dryness. The crude residue was purified by basic silica-gel column chromatography using ethyl acetate/hexane (50:50) as an eluent to obtain Compound-11B as a yellow solid. LC-MS purity: 87.20%; Mass (m/z): 493.3 $[M+H]^+$; Yield: 220 mg (66.6%); TLC system: EtOAc:Hexane [30:70]; $R_f$: 0.1.

Step-9: Synthesis of tert-butyl ((1r,4r)-4-((8-ethyl-6-(2-methoxy-6-((2,2,2-trifluoroethyl) sulfonamido) pyridin-3-yl) quinazolin-2-yl) amino) cyclohexyl) carbamate (12B)

To a stirred solution of 5-bromo-6-methoxypyridin-2-amine (Compound-11B) (200 mg, 0.41 mmol) in pyridine (1 mL) was added, 2,2,2-trifluoroethane-1-sulfonyl chloride (96 mg, 0.53 mmol) slowly. The mixture was stirred at room temperature for 4 h and concentrated to dryness. The crude residue was directly used in the next step [Compound-12B, as a brown liquid). LC-MS purity: 67.1%; Mass (m/z): 639.4 $[M+H]^+$; Yield: 180 mg (69.4%); TLC system: EtOAc: Hexane 320:70]; $R_f$: 0.1.

Step-9: Synthesis of N-(5-(2-(((1r,4r)-4-aminocyclohexyl) amino)-8-ethylquinazolin-6-yl)-6-methoxypyridin-2-yl)-2,2,2-trifluoroethane-1-sulfonamide (Target-3)

To a stirred solution of tert-butyl ((1r,4r)-4-((8-ethyl-6-(2-methoxy-6-((2,2,2-trifluoroethyl) sulfonamido) pyridin-3-yl) quinazolin-2-yl) amino) cyclohexyl) carbamate (180 mg) in 1,4-dioxane (1 mL) was added 4M-HCl in dioxane (1.5 mL). The reaction mixture was stirred at room temperature for 2 h, concentrated and triturated with $Et_2O$. The crude material was purified by PREP HPLC. The collected fractions were lyophilized to obtain Target-3 as a yellow solid. LC-MS purity: 95.4%; Mass (m/z): 539.4 [M+H]$^+$; Yield: 30 mg (19.8%); TLC system: MeOH:DCM [20:80]; $R_f$: 0.2. $^1$H NMR (400 MHz, DMSO-d6): δ 11.38 (s, 1H), 9.10 (brs, 1H), 7.83-7.73 (m, 6H), 7.40 (brs, 1H), 6.63 (d, 1H), 4.93 (q, J=9.2 Hz, 19.2 Hz, 2H), 3.90 (s, 3H), 3.89-3.83 (m, 1H), 3.10-3.05 (m, 1H), 2.99 (q, J=8 Hz, 15.2 Hz, 2H), 2.20-2.10 (m, 2H), 2.10-1.99 (m, 2H), 1.48-1.35 (m, 4H), 1.30 (t, J=7.2 Hz, 3H).

Example 4: Methods

Expression and Purification of IRE1α* and dP-IRE1α*

A construct containing the cytosolic kinase and RNase domains of human IRE1α (residues 547-977, IRE1α*) was expressed in SF9 insect cells by using the Bac-to-Bac baculovirus expression system (Invitrogen) with a His6 tag at the N-terminus and purified with a nickel-nitriloacetic acid (Qiagen) column. To generate dP-IRE1α*, we removed basal phosphorylation sites by incubating IRE1α* with λ-PPase (New England Biolabs) at a molar ratio of 5:1 (IRE1α*: X-PPase) in 50 mM HEPES pH 7.5, 100 mM NaCl, 1 mM $MnCl_2$, 2 mM dithiothreitol (DTT) and 0.01% Brij 35 detergent (v/v) overnight at 4° C. Dephosphorylation was verified through western blotting using a universal phospho-protein detection agent (biotin-pIMAGO (Tymora Analytical Operations, Cat. No.: FL800) and imaged using a streptavidin-linked fluorophore.

Western Blotting and Antibodies

For protein analysis, cells were lysed into modified RIPA buffer (50 mM Tris, 150 mM NaCl, 10 mM NaF, 1% NP40 (v/v), 0.25% sodium deoxycholate (w/v), 5% glycerol (v/v), pH 7.8) containing protease inhibitor (Pierce Protease Inhibitor Tablets and 1 mM PMSF) and phosphatase inhibitor (Phosphatase inhibitor cocktail 2 and 3, Sigma Aldrich) prior to gel loading. Western blots were performed using Any kD™ Mini-PROTEAN© TGX™ Precast protein gels (BioRad). Gels were ran using Tris-Glycine running buffer (25 mM Tris pH 8.6, 192 mM glycine, 0.1% SDS (w/v)) at 180 V. Gels were transferred to nitrocellulose paper using the TransBlot Turbo System (BioRad) at 25 V, 2.5 A for 15 minutes. Nitrocellulose blots were blocked for 30 minutes at room temperature with Odyssey blocking buffer (Li-Cor). Primary antibodies were diluted into blocking buffer and incubated over night at 4° C. Blots were washed 2× with TBST (20 mM Tris pH 7.5, 150 mM NaCl, 0.1% Tween-20) and incubated with near-infrared-dye-conjugated secondary antibodies (Li-Cor) for 1 hour at room temperature. Blots were imaged using a Li-Cor Odyssey IR Imager and quantitated using ImageStudio. The following primary antibodies were used in this study: rabbit anti-IRE1α mAb #14C10 (Cell Signaling, no. 3294), mouse anti-FLAG (DYKDDDDK (SEQ ID NO:20)) mAb (Sigma Aldrich, no. F3165), rabbit anti-spliced XBP1 (Cell Signaling, no. 12782), rabbit anti-caspase 3 (Cell Signaling, no. 9662), rabbit anti-cleaved caspase 3 (Cell Signaling, no. 9661), mouse anti-proinsulin (Santa Cruz Biotechnology, no. sc-9168), and rabbit anti-GAPDH (Santa Cruz Biotechnology, no. sc-25778).

In Vitro Kinase Activity Assay

Inhibitors (initial concentration of 10 or 60 μM, three-fold serial dilutions) were incubated with IRE1α* in cleavage buffer (20 mM HEPES, 0.05% Triton X-100 (v/v), 50 mM KCl, 1 mM $MgCl_2$, 1 mM DTT, pH 7.5) for 30 min, followed by incubation with 10 μCi [$\gamma^{32}$P] ATP(3,000 Ci $mmol^{-1}$, PerkinElmer) at 23° C. for 3 hours. Samples were then spotted onto glass fiber paper (Easytab-C Glass Fiber Filter Paper, Perkin Elmer) and washed in twice with 0.5% phosphoric acid and autoradiographed using a GE Typhoon FLA 9000 Imager. Blots were quantitated using ImageQuant software. The percent inhibition was quantified by setting the background (no kinase well) as 0 and standardizing to IRE1α* without compound treatment (IRE1α*+DMSO). Dose-response curves were fit using "one-site fit logIC50" parameter using GraphPad Prism analysis software.

In Vitro RNase Activity Assay Inhibitor Titrations 50 nM IRE1α* was incubated with inhibitor (initial concentration of 10 or 60 μM, three-fold serial dilutions) or DMSO for 30 min in assay buffer (20 mM Tris, 50 mM NaCl, 1 mM $MgCl_2$, 2 mM DTT, 0.05% Triton X-100 (v/v), pH 7.5). Assays were initiated by adding 10 L of XBP1-mini substrate (5'-Alex647-CAUGUCCGCAGCGCAUG-IowaBlack-FQ-3'; IDT) to the wells at a final concentration of 200 nM and a final well volume of 30 μL. Fluorescence was detected on a Perkin Elmer Envision Microplate Reader at excitation and emission wavelengths of 650 nm and 665 nm. Dose-response curves were fit using "one-site fit logIC50" parameter using GraphPad Prism analysis software.

In Vitro $K_{dimer}$ Assay

IRE1α* or dPIRE1α* was titrated from either 2 μM or 4 μM in two-fold serial dilutions in assay buffer (20 mM Tris, 50 mM sodium chloride, 1 mM $MgCl_2$, 2 mM DTT, 0.05% Triton X-100 (v/v), pH 7.5) and incubated with 50 μM inhibitor for 30 minutes at room temperature. Assays were initiated by adding 10 μL of XBP1-mini substrate (5'-Alex647-CAUGUCCGCAGCGCAUG-IowaBlack-FQ-3' (SEQ ID NO:1); IDT) to the wells at a final concentration of 6 μM and a final well volume of 30 μL. Fluorescence was detected on a Perkin Elmer Envision Microplate Reader at excitation and emission wavelengths of 650 nm and 665 nm. Reaction process was monitored real time in 10-second intervals for at least 30 minutes. Initial rates of XBP1-cleavage were determined for each respective IRE1α* of dpIRE1α* concentration. Specific activity was then determined by dividing rate (RFU/s) by the respective IRE1α* of dpIRE1α* used (RFU/s*[IRE1α]). $K_{dimer}$ values were determined by fitting these values using the non-linear regression 'one-site total' binding parameter in GraphPad Prism analysis software.

Crystallization of IRE1α*+PAIR1

Protein Production and Crystallization

Expression of IRE1α was performed according to previously established protocols. A purification protocol was established and homogeneous protein was produced in preparative amounts. The protein was purified comprising affinity and gel filtration chromatography steps. This procedure yielded homogenous protein with a purity greater 95% as judged from Coomassie stained SDS-PAGE. The purified protein was used in crystallization trials employing both, a standard screen with approximately 1200 different conditions, as well as crystallization conditions identified using literature data. Conditions initially obtained have been optimized using standard strategies, systematically varying parameters critically influencing crystallization, such as temperature, protein concentration, drop ratio, and others. These conditions were also refined by systematically varying pH or precipitant concentrations.

Structural Modeling and Refinement

The phase information necessary to determine and analyze the structure is obtained by molecular replacement. A previously solved structure of IRE1α is used as a search model. Subsequent model building and refinement is performed according to standard protocols with the software packages CCP4 and COOT. For the calculation of the free R-factor, a measure to cross-validate the correctness of the final model, about 2.6% of measured reflections are excluded from the refinement procedure. TLS refinement (using REFMAC5, CCP4) is carried out, which results in lower R-factors and higher quality of the electron density map. Automatically generated local NCS restraints is applied (keyword "ncsr local" of newer REFMAC5 versions). The ligand parameterization and generation of the corresponding library files are carried out with CORINA. The water model is built with the "Find waters" algorithm of COOT by putting water molecules in peaks of the Fo-Fc map contoured at 3.0 followed by refinement with REFMAC5 and checking all waters with the validation tool of COOT. The criteria for the list of suspicious waters were: B-factor greater 80 Å$^2$, 2Fo-Fc map less than 1.2σ, distance to closest contact less than 2.3 Å or more than 3.5 Å. The suspicious water molecules and those in the ligand binding site (distance to ligand less than 10 Å) are checked manually.

Kinome Profiling and Selectivity

Kinobead Enrichment Protocol

HEK293 and HCT116 cells were plated on 15 cm plates until 90% confluent and lysed into 750 μL modified RIPA buffer (50 mM Tris, 150 mM NaCl, 10 mM NaF, 1% NP40, 0.25% sodium deoxycholate, 5% glycerol, pH 7.8) containing protease inhibitor (Pierce Protease Inhibitor Tablets and 1 mM PMSF) and phosphatase inhibitor (Phosphatase inhibitor cocktail 2 and 3, Sigma Aldrich). Protein content was determined via Bradford assay. HEK293 and HCT116 lysates were combined in a 1:1 ratio and exogenous IRE1α* was added to the lysate at a final concentration of 33.3 nM. Lysate (300 μg per sample) was incubated and rotated end over end with 10 μM inhibitor or DMSO (1% v/v) for 1 hour at 4° C. For kinase enrichment, 10 μL of 50% kinobead slurry (in 20% ethanol) was prepared by washing twice with 500 μL Mod. RIPA buffer. DMSO or inhibitor treated lysates were then added to the washed kinobeads and rotated end over end for 3 hours at 4° C. After enrichment, the supernatant was aspirated off and the beads were washed twice with 500 μL ice cold Mod. RIPA buffer and three times with 500 μL ice cold TBS (50 mM Tris, 150 mM NaCl, pH 7.8) to remove detergent. Beads were resuspended in 25 μL of denaturing buffer (6M guanidinium chloride, 50 mM Tris containing 5 mM TCEP and 10 mM CAM, pH 8.5). The bead slurries in denaturing buffer were then heated to 95° C. for 5 min. After, the bead slurries were diluted 2-fold (add 25 μL) with 100 mM TEAB (triethylammonium bicarbonate buffer, pH 8.5). Then 0.4 μg of LysC (Wako) were added to the beads and the pH adjusted to 8-9 with 1N NaOH. The mixture was agitated on a Thermomixer (Eppendorf) at 37° C. for 2 hr at 1400 rmp. After, the samples were diluted 2-fold (50 μL) with 100 mM TEAB and 0.4 μg of sequencing grade trypsin (Pierce) was added and the samples agitated for another 12 hr at 37° C. at 800 rpm in the Thermomixer. After the overnight trypsinization, samples were diluted 2-fold (100 μL) with Buffer A (5% ACN, 0.1% TFA) containing 1% formic acid and the pH adjusted to 2-3 with formic acid if necessary. Homemade StageTips were prepared by running 50 μL of Buffer B (80% ACN, 0.1% TFA, $H_2O$) through them followed by 50 μL of Buffer A (5% ACN, 0.1% TFA, $H_2O$).[92] Beads were spun down and supernatant was added directly to StageTips. Following sample loading, StageTips were washed with 50 μL of Buffer A and eluted with 50 μL Buffer B. Samples were speed vacuumed until dry and re-suspend in Buffer A for injection onto LC-MS.[79]

LC-MS and Data Analysis

Tryptic peptides were separated using a nanoAcquity UPLC instrument with 10 cm fused silica capillary columns made in house and packed with 5 μm 120 Å reverse-phase C18 beads (ReproSil-Pur®, Maisch). Liquid chromatography was performed over 120 minutes using and initial 20 minute isocratic trapping of 3% Buffer B and a flow rate of 700 nL/min followed by a 100 minute gradient of 35% Buffer B to 80% Buffer B gradient at 350 nL/min. LC Buffer A solvent is 0.1% acetic acid and LC Buffer B is 99.9% ACN, 0.1% acetic acid. MS data was analyzed using a Thermo Orbitrap Fusion Tribrid. Raw files were analyzed using MaxQuant (*Andromeda*) Version 1.6.0.16. Files were analyzed further using Perseus (Version 1.6.0.7) by filtering LFQ intensity values only identified by site, reverse, or potential contaminant. Missing LFQ intensity values were imputed in Perseus from a standard distribution downshifted by 1.8 and having a width of 0.4. To determine kinases that were significantly competed by treatment with 10 μM of inhibitor we applied a two-tailed two-sample t-test in Perseus with an FDR of 0.05. Kinases were reported as being non-competed by an inhibitor if it had a $Log_2$ LFQ ratio ($Log_2$ Difference)<1.0. Kinome tree visualization plots were created using CORAL and heat maps were made using GraphPad Prism V.8.

Phostag Acrylamide Gels

Treatment Conditions for Phostag Gels

INS-1 or IRE1α-overexpressing isogenic INS-1 cells were plated onto a 24-well Poly-D-Lysine coated tissue culture plate and grown for 48 hrs. Inhibitor or DMSO were added to the media and incubated for 1 hour at 37° C. with 5% $CO_2$ prior to addition of ER stress agents. After the 1 hour inhibitor incubation, cells were treated 200 μg/mL BFA (Sigma, Prod. No.: B6542) for 2 hours or 5 ng/mL doxycycline (Sigma) for 6 hours, with care to ensure the total DMSO concentration in the media did not exceed 1% (v/v). Cells were lysed directly into SDS loading buffer (50 mM Tris, 100 mM DTT, 2% SDS (w/v), 10% glycerol (v/v), and 0.1% bromophenol blue (w/v), pH 6.8) and boiled for five minutes prior to gel loading.

Phostag Acrylamide Gel Procedure

A phostag acrylamide gel recipe used to resolve phosphorylation of IRE1α has been previously established and this recipe was followed verbatim for this study.[91] Resolving gels were allowed to solidify (~1.5 hr) before adding the stacking gel and comb and allowed to solidify (~1 hr). Gels were run using Tris-Glycine-SDS running buffer (25 mM Tris, 192 mM glycine, 0.1% SDS, pH 8.3) at 100 V for 3-3.5 hours. After the gels have ran, they were transferred onto nitrocellulose paper via rapid transfer using a Transblot Turbo and premade transfer packs. Gels were transferred at 25 V, 2.5 A for 15 minutes. Once transferred onto nitrocellulose, proceed with western blotting procedure as normal.

Tissue Culture

INS-1s (rat insulinoma beta cells) were grown in RPMI, 10% FBS buffer (v/v), 1 mM sodium pyruvate, 10 mM HEPES, 2 mM glutamine and 50 μM β-mercaptoethanol on Poly-D-Lysine coated tissue culture flasks. IRE1α (murine) was cloned into a pcDNA5/FRT/TO. INS-1 FRT/TO cells were grown following the protocol above. INS-1 FRT/TO cells were transfected with 2 μg IRE1α-pcDNA5/FRT/TO and 2 μg pOG44 using Lipofectamine 2000 (Thermo Fisher). Cell media was exchanged the next day and cells were allowed grow for another day before passaging. Selection was performed using 50 μg/mL Hygromycin-B (Thermo Fisher) over about two weeks until all un-transfected cells have died and colonies have appeared in transfected cells. Stably integrated cells were maintained in RPMI, 10% FBS buffer (v/v), 1 mM sodium pyruvate, 10 mM HEPES, 2 mM glutamine and 50 μM β-mercaptoethanol, 25 g/mL Hygromycin-B. HEK293 cells were grown in DMEM High Glucose media (Gibco) supplemented with 10% FBS. HCT-116 cells were maintained in McCoy's 5A modified media (Gibco) supplemented with 10% FBS. All cells lines were maintained at 37° C. with 5% $CO_2$.

RNA Isolation, Quantitative Real-Time PCR, and Primers

INS-1 or isogenic IRE1α-overexpressing INS-1 cells were plated onto Poly-D-Lysine coated tissue culture plate and grown for 48 hrs. Inhibitors or DMSO were added to the media and incubated for 1 hour at 37° C. with 5% $CO_2$ prior to addition of ER stress agents or Dox as indicated. RNA was isolated from whole cells using either QIAGEN RNeasy Mini kits or Trizol (Invitrogen) and reverse transcribed as above to obtain total cDNA. Then, XBP-1 primers were used to amplify an XBP-1 amplicon spanning the 26 nt intron from the cDNA samples in a regular 3-step PCR. Thermal cycles were: 5 min at 95° C., 30 cycles of 30 s at 95° C., 30 s at 60° C., and 1 min at 72° C., followed by 72° C. for 15 min, and hold at 4° C. Primers used for XBP-1 mRNA splicing were as follows: sense primer XBP1.3S (5'-AAACAGAGTAGCACAGACTGC-3' (SEQ ID NO:2)) and antisense primer XBP1.2AS (5'-GGATCTCTAAGACTAGAGGCTTGGTG-3' (SEQ ID NO:3)). PCR fragments were then digested by PstI, resolved on 3% agarose gels, stained with EtBr and quantified by densitometry using ImageJ (NIH). For standard mRNA detection, generally 1 mg total RNA was reverse transcribed using the QuantiTect Reverse Transcription Kit (QIAGEN). For qPCR, we used SYBR green (QIAGEN) and StepOnePlus Real-Time PCR System (Applied Biosystems). Thermal cycles were: 5 min at 95° C., 40 cycles of 15 sec at 95° C., 30 sec at 60° C. Gene expression levels were normalized to Beta Actin. Primers used for qPCR of RIDD targets were as follows: Beta Actin Fwd: 5'-GCAAATGCTTCTAGGCGGAC-3' (SEQ ID NO:4), Beta Actin Rev: 5'-AAGAAAGGGTGTAAAACGCAGC-3' (SEQ ID NO:5), Insulin 1 Fwd: 5'-GTCCTCTGGGAGCCCAAG-3' (SEQ ID NO:6), Insulin 1 Rev: 5'-ACAGAGCCTCCACCAGG-3' (SEQ ID NO:7), Insulin 2 Fwd: 5'-ATCCTCTGGGAGCCCCGC-3' (SEQ ID NO:8), Insulin 2 Rev: 5'-AGAGAGCTTCCACCAAG-3' (SEQ ID NO:9), Blos1 Fwd: 5'-CAAGGAGCTGCAGGAGAAGA-3' (SEQ ID NO:10), and Blos1 Rev: 5'-GCCTGGTTGAAGTTCTCCAC-3' (SEQ ID NO: 11).

Annexin-V Staining

For assaying apoptosis by Annexin V staining, cells were plated in 12-well plates overnight. Cells were then treated with various reagents for indicated time periods. On the day of flow cytometry analysis, cells were trypsinized and washed in PBS and resuspended in Annexin V binding buffer with Annexin-V FITC (BD Pharmingen™). Flow cytometry was performed on a Becton Dickinson LSRII flow cytometer.

Ex Vivo Islet Studies and Glucose Stimulated Insulin Secretion

Non-diabetic human islets were obtained and cultured in supplemented Prodo Islet Medium (PIM(S) from Prodo Labs). Islets were pretreated with either DMSO, PAIR1, or KIRA9 for 2 hrs followed by treatment with 0.5 μg/mL tunicamycin for 16 hrs. Approximately 50 islets were cultured for each condition in triplicate. In the GSIS assay, islets were preincubated in HEPES-buffered Krebs-Ringer bicarbonate solution (KRBH) (10 mM HEPES, 129 mM NaCl, 4.7 mM KCl, 1.2 mM $KH_2PO_4$, 1.2 mM $MgSO_4$, 2 mM $CaCl_2$, 5 mM $NaHCO_3$, 0.1% BSA, pH 7.4) containing 2.5 mM glucose for 30 min at 37° C. Fifty islets per condition were incubated with either 2.5 mM or 16.7 mM glucose in KRBH at 37° C. for 30 min. Collected media were analyzed by anti-insulin ELISA (EMD Millipore) and insulin levels were normalized to total protein amount.

RNA Sequencing

RNA Isolation and Preparation

Isogenic IRE1α-overexpressing INS-1 cells were pretreated with inhibitors for 1 h followed by addition of Dox 5 ng/ml for 4 h and 24 h as indicated. All conditions for RNAseq analysis were performed in three biological replicates. RNA was isolated from whole cells using Qiagen RNeasy with gDNA eliminator kit. RNA purity was determined using a NanaPhotometer spectrometer (IMPLEN, CA, USA). RNA integrity and quantitation were assessed using the RNA Nano 6000 Assay Kit of the Bioanalyzer 2100 system (Agilent Technologies, CA, USA).

Library Preparation

Library preparation for RNAseq was performed by Novogene. A total amount of 1 μg RNA per sample was used as input material for the RNA sample preparations. Sequencing libraries were generated using NEBNext® Ultra™ RNA Library Prep Kit for Illumina® (NEB, USA) following manufacturer's recommendations and index codes were added to attribute sequences to each sample. Briefly, mRNA was purified from total RNA using poly-T oligo-attached magnetic beads. Fragmentation was carried out using divalent cations under elevated temperature in NEBNext First Strand Synthesis Reaction Buffer (5×). First strand cDNA was synthesized using random hexamer primer and MMuLV Reverse Transcriptase (RNase H). Second strand cDNA synthesis was subsequently performed using DNA Polymerase I and RNase H. Remaining overhangs were converted into blunt ends via exonuclease/polymerase activities. After adenylation of 3' ends of DNA fragments, NEBNext Adaptor with hairpin loop structure were ligated to prepare for hybridization. In order to select cDNA fragments of preferentially 150-200 bp in length, the library fragments were purified with AMPure XP system (Beckman Coulter, Beverly, USA). Then 3 μL USER Enzyme (NEB, USA) was used with size-selected, adaptor-ligated cDNA at 37° C. for 15 min followed by 5 min at 95° C. before PCR. Then PCR was performed with Phusion High-Fidelity DNA polymerase, Universal PCR primers and Index (X) Primer. At last, PCR products were purified (AMPure XP system) and library quality was assessed on the Agilent Bioanalyzer 2100 system.

Clustering and Sequencing

The clustering of the index-coded samples was performed on a cBot Cluster Generation System using PE Cluster Kit cBot-HS (Illumina) according to the manufacturer's instructions. After cluster generation, the library preparations were sequenced on an Illumina platform and 125 bp/150 bp paired-end reads were generated.

Quality Control and Genome Mapping

Raw data (raw reads) of fastq format were firstly processed using Novogene perl scripts. In this step, clean data (clean reads) were obtained by removing reads containing adapter, reads containing ploy-N and low quality reads from raw data. At the same time, Q20, Q30 and GC content the clean data were calculated. All the downstream analyses were based on the clean data with high quality. Reference genome and gene model annotation files were downloaded from genome website directly. Index of the reference genome was built using hisat2 2.1.0 and paired-end clean reads were aligned to the reference genome using HISAT2.

Quantification of Gene Expression Level

HTSeq v0.6.1 was used to count the reads numbers mapped to each gene. And then FPKM of each gene was calculated based on the length of the gene and reads count mapped to this gene. FPKM, expected number of Fragments Per Kilobase of transcript sequence per millions base pairs sequenced, considers the effect of sequencing depth and gene length for the reads count at the same time, and is currently the most commonly used method for estimating gene expression levels (Trapnell, C. et al. (2010). Transcript assembly and quantification by RNA-seq reveals unannotated transcripts and isoform switching during cell differentiation. Nat. Biotechnol).

Differential Expression Analysis

Differential expression analysis of two conditions/groups (three biological replicates per condition) was performed using the DESeq R package (1.18.0). DESeq provide statistical routines for determining differential expression in digital gene expression data using a model based on the negative binomial distribution. The resulting P-values were adjusted using the Benjamini and Hochberg's approach for controlling the false discovery rate. Genes with an adjusted P-value<0.05 found by DESeq were assigned as differentially expressed GO and KEGG Enrichment Analysis of Differentially Expressed Genes Gene Ontology (GO) enrichment analysis of differentially expressed genes was implemented by the GOseq R package, in which gene length bias was corrected. GO terms with corrected P-value less than 0.05 were considered significantly enriched by differential expressed genes. KEGG is a database resource for understanding high-level functions and utilities of the biological system, such as the cell, the organism and the ecosystem, from molecular-level information, especially large-scale molecular datasets generated by genome sequencing and other high-through put experimental technologies (http://www.genome.jp/kegg/). We used KOBAS software to test the statistical enrichment of differential expression genes in KEGG pathways.

Splenocyte Isolation and Differentiation

Splenocytes were isolated from a C57BL/6 mouse into single cell suspension in complete media: RPMI 1640, L-glutamine (Corning-Gibco), penicillin/streptomycin L-glutamine (Life Technologies), 10 mM HEPES buffer (Life Technologies), non-essential amino acids (Life Technologies), 1 mM sodium pyruvate (Life Technologies), 55 mM 2-mercaptoethanol (Gibco), and 10% heat inactivated fetal bovine serum (Omega Scientific). Red blood cells were lysed with ammonium chloride potassium buffer. Splenocytes were plated at $2.5\times10^5$ cells/well in a 96-well round bottom plate in complete media. The splenocytes were treated with or without 1 μg/ml LPS 026:b6 (Sigma). Two-fold serial dilutions of IRE1α inhibitors (20 μM-1.25 μM) were prepared in DMSO and added to the LPS treated cells at a final dilution of 1:1000. The splenocytes were incubated for three days in a 37° C., 5% $CO_2$ humidified chamber before collection and staining for flow cytometry.

Flow Cytometry

Cells from the plasma cell assay were collected in a 96-well plate and washed with PBS followed by staining with LIVE/DEAD Fixable Near-IR Dead Cell Stain kit (Invitrogen). Reagent was reconstituted as per manufacturer's instructions, diluted 1:1000 in PBS, and cells were stained in 100 μL on ice for 20 minutes. The cells were then washed with FACS buffer, PBS (Corning), 2 mM EDTA and 2% heat inactivated fetal bovine serum (Omega Scientific). The cells were then stained with 50 μL antibody cocktail consisting of anti-CD19 (BioLegend), anti-CD45R (BD Pharmingen), and anti-CD138 (BioLegend) in FACS buffer on ice for 15 minutes. Cells were resuspended in FACS buffer and combined with an equal volume of 4% paraformaldehyde with 5000 Countbright Absolute Counting Beads (Thermofisher). Stained cells were analyzed on a Fortessa (Becton Dickinson). Data analysis was performed using FlowJo (v10) software (Treestar Inc.).

ELISA for Secreted IgM

Media supernatants from the in vitro plasma cell differentiation assay were measured for secreted IgM by ELISA. 96-well plates (Costar, #3690) were coated with 1 μg/ml goat anti-IgM (Southern Biotech, #1020-01) in PBS. Wash buffer (PBS with 0.05% Tween-20 (v/v)) was used for all washing steps and blocked with PBS-BB (PBS without $Ca^{2+}/Mg^{2+}$, 1% BSA (w/v), 0.05% Tween-20(v/v)). Supernatants from LPS stimulated samples were diluted (1:100) and media only samples were diluted (1:10) in PBS-BB. IgM standard (Southern Biotech, #0101-01) was prepared in a 2-fold serial dilution in PBS-BB. IgM was detected with Goat anti-IgM-HRP (Southern Biotech, #1020-05) diluted (1:3000) in PBS-BB. ELISA plates were developed with TMB (Sigma) and stopped with 1N sulfuric acid. Absorbance was measured at 450 nm using spectrophotometer (Spectramax M5, Molecular Devices). Sample IgM concentration values were calculated with SoftMaxPro software.

XBP1 Splicing

RNA was extracted using Trizol (Invitrogen), DNaseI treated, and cDNA products encompassing the intron amplified by QuantiTect Reverse Transcription Kit (Qiagen). sense Primer rXBP Forward (5'-TGAAAAACAGAGTAGCAGCACAGA-3' (SEQ ID NO:12)) and antisense primer rXBP Reverse (5'-AAGGGAGGCTGGTAAGGAAC-3' (SEQ ID NO:13)) were used. PCR fragments were digested by PstI, resolved on 3% agarose gels, stained with EtBr, and quantified by densitometry.

Real-Time PCR

Real-Time PCR (Q-PCR) used SYBR green and Step OnePlus Real-Time PCR System (Applied Biosystems). Thermal cycles were: 5 min at 95° C., 40 cycles of 15 s at 95° C., 30 s at 60° C. Gene expression levels were normalized to GAPDH. Q-PCR Sense/antisense primers used: Rat GAPDH, 5'-AGTTCAACGGCACAGTCAAG-3' (SEQ ID NO:14) and 5'-TACTCAGCACCAGCATCACC-3' (SEQ ID NO:15); Rat Ins1, 5'-GTCCTCTGGGAGCCCAAG-3' (SEQ ID NO:6) and 5'-ACAGAGCCTCCACCAGG-3' (SEQ ID NO:7); Rat Pdia4, 5'—CGTCTCGCCCTGATTCGT-3' (SEQ ID NO:16) and 5'-GGAAGTTCAGCCCGGTGATT-3' (SEQ ID NO:17); Rat Blos1, 5'-TGGATTGGCATGGTGGAAAAC-3' (SEQ ID NO:18) and 5'-TGTCCAGTTCGATGCTCCG-3' (SEQ ID NO:19).

Compound Characterization ($IC_{50}$ IRE1α Kinase Inhibition)

| Name | Structure | FREE BASE Molecular weight (g/mol) | Salt | with SALT MW | $IC_{50}$ IRE1α |
|---|---|---|---|---|---|
| LBC-0000408 | 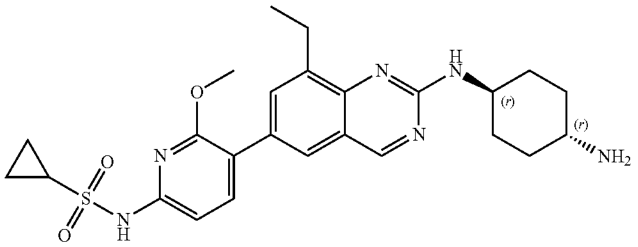 [SMILES: CCc1cc(-c2ccc(NS(=O)(=O)C3CC3)nc2OC)cc2cnc(N[C@H]3CC[C@H](N)CC3)nc12] | 496.63 | HCl | 533 | 5.1 nM |
| LBC-0000407 | 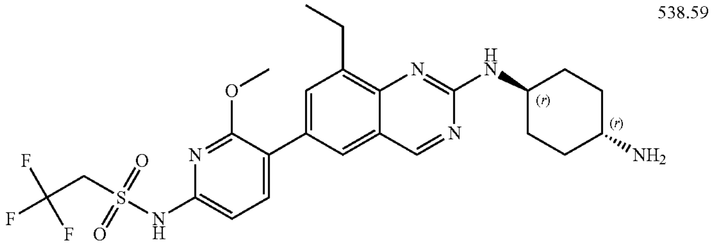 | 538.59 | TFA | 653 | 7.5 nM |
| LBC-0000406 | 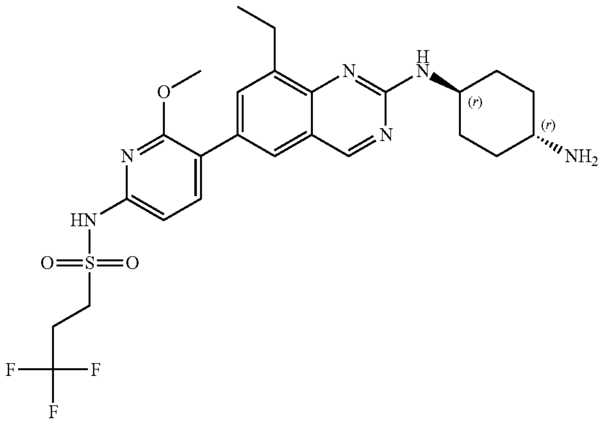 [SMILES: CCc1cc(-c2ccc(NS(=O)(=O)CCC(F)(F)F)nc2OC)cc2cnc(N[C@H]3CC[C@H](N)CC3)nc12] | 552.62 | HCl | 589 | 7.4 nM |
| LBC-0000405 (Compound 37) | 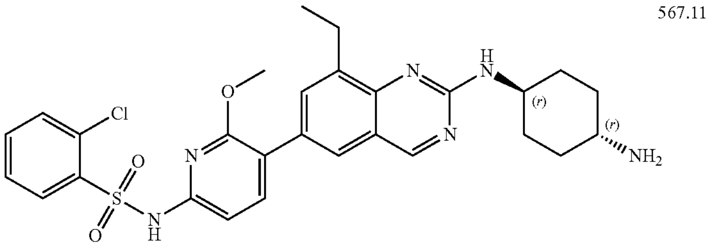 | 567.11 | HCl | 604 | 5.1 nM |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

(I)

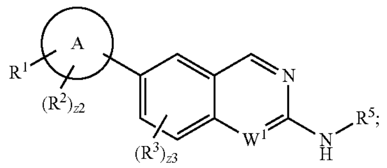

wherein

Ring A is 3-pyridinyl;

$R^1$ is $—NR^{1A}SO_2R^{1B}$;

$R^{1A}$ is hydrogen or substituted or unsubstituted alkyl;

$R^{1B}$ is hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, unsubstituted alkyl, substituted or unsubstituted heteroalkyl, substituted or unsubstituted cycloalkyl, or substituted or unsubstituted heterocycloalkyl;

$R^2$ is independently halogen, $—CX^2_3$, $—CHX^2_2$, $—CH_2X^2$, $—OCX^2_3$, $—OCH_2X^2$, $—OCHX^2_2$, $—OR^{2D}$, substituted or unsubstituted alkyl, or substituted or unsubstituted heteroalkyl;

$R^{2D}$ is independently hydrogen or substituted or unsubstituted alkyl;

z2 is an integer from 0 to 4;

$R^3$ is independently halogen, $—CX^3_3$, $—CHX^3_2$, $—CH_2X^3$, substituted or unsubstituted alkyl, or substituted or unsubstituted heteroalkyl;

z3 is an integer from 0 to 4;

$W^1$ is —N═;

$R^5$ is substituted or unsubstituted alkyl or substituted or unsubstituted cycloalkyl; and $X^2$ and $X^3$ are independently —F, —Cl, —Br, or —I;

or a salt thereof.

2. The compound of claim 1, wherein $R^5$ is substituted or unsubstituted $C_1$-$C_4$ alkyl or substituted or unsubstituted $C_3$-$C_8$ cycloalkyl.

3. The compound of claim 1, having the formula:

(Ia)

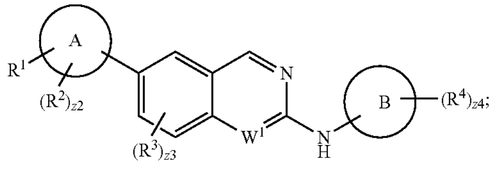

wherein

Ring B is cycloalkyl;

$R^4$ is independently oxo, halogen, $—CX^4_3$, $—CHX^4_2$, $—CH_2X^4$, $—OCX^4_3$, $—OCH_2X^4$, $—OCHX^4_2$, —CN, $—SO_{n4}R^{4D}$, $—SO_{v4}NR^{4A}R^{4B}$, $—NR^{4C}NR^{4A}R^{4B}$, $—ONR^{4A}R^{4B}$, $—NHC(O)NR^{4C}NR^{4A}R^{4B}$, $—NHC(O)NR^{4A}R^{4B}$, $—N(O)_{m4}$, $—NR^{4A}R^{4B}$, $—C(O)R^{4C}$, $—OC(O)R^{4C}$, $—C(O)—OR^{4C}$, $—OC(O)—OR^{4C}$, $—C(O)NR^{4A}R^{4B}$, $—OC(O)NR^{4A}R^{4B}$, $—OR^{4D}$, $—NR^{4A}SO_2R^{4D}$, $—NR^{4A}C(O)R^{4C}$, $—NR^{4A}C(O)OR^{4C}$, $—NR^{4A}OR^{4C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z4 is an integer from 0 to 5;

$R^{4A}$, $R^{4B}$, $R^{4C}$ and $R^{4D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

$X^4$ is independently —F, —Cl, —Br, or —I;

n4 is an integer from 0 to 4; and m4 and v4 are independently 1 or 2;

or a salt thereof.

4. The compound of claim 3, having the formula:

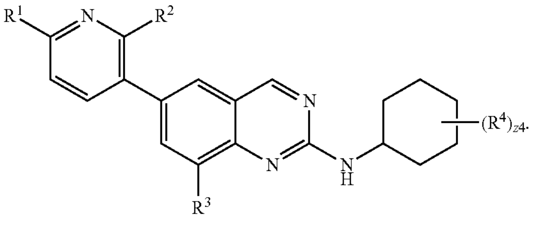

5. The compound of claim 1, wherein $R^1$ is $-NR^{1A}SO_2R^{1B}$;

$R^{1A}$ is hydrogen or unsubstituted $C_1$-$C_4$ alkyl; and $R^{1B}$ is hydrogen, unsubstituted $C_1$-$C_2$ alkyl, or halo-substituted or unsubstituted $C_3$-$C_4$ cycloalkyl.

6. The compound of claim 3, having the formula:

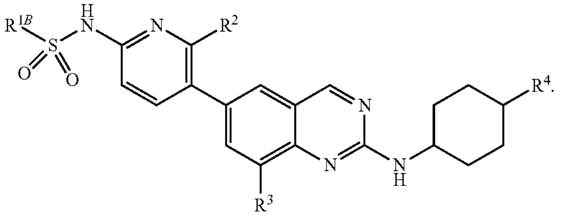

7. The compound of claim 1, wherein $R^2$ is independently $-OCX^2{}_3$, $-OCH_2X^2$, $-OCHX^2{}_2$, or $-OCH_3$.

8. The compound of claim 1, wherein $R^3$ is independently unsubstituted $C_1$-$C_3$ alkyl.

9. The compound of claim 3, wherein $R^4$ is independently $-NR^{4A}R^{4B}$; and $R^{4A}$ and $R^{4B}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, or unsubstituted $C_1$-$C_4$ alkyl.

10. The compound of claim 3, wherein $R^4$ is independently $-NH_2$.

11. A compound having the formula:

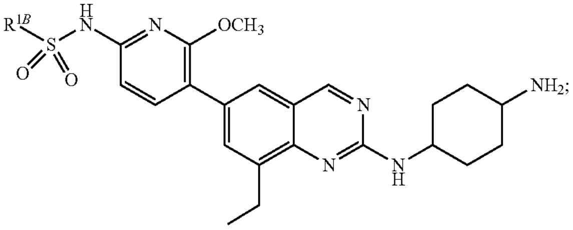

wherein $R^{1B}$ is hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, or substituted or unsubstituted heterocycloalkyl.

12. The compound of claim 1, wherein $R^{1B}$ is unsubstituted $C_3$-$C_4$ cycloalkyl.

13. The compound of claim 1, wherein $R^{1B}$ is unsubstituted cyclopropyl.

14. A pharmaceutical composition comprising the compound of claim 1 and a pharmaceutically acceptable excipient.

15. The compound of claim 11, wherein $R^{1B}$ is $-CH_2CF_3$.

16. The compound of claim 11, wherein $R^{1B}$ is unsubstituted cyclopropyl.

17. A pharmaceutical composition comprising the compound of claim 11 and a pharmaceutically acceptable excipient.

* * * * *

UNITED STATES PATENT AND TRADEMARK OFFICE

CERTIFICATE OF CORRECTION

PATENT NO. : 11,840,523 B2
APPLICATION NO. : 17/525764
DATED : December 12, 2023
INVENTOR(S) : Feroz R. Papa et al.

It is certified that error appears in the above-identified patent and that said Letters Patent is hereby corrected as shown below:

In the Specification

In Column 1, Lines 15-18, delete "This invention was made with government support under grant nos. U01 DK123609 and R01 DK100623 awarded by The National Institutes of Health. The government has certain rights in the invention." and insert -- This invention was made with government support under grant no. U01 DK123609 awarded by The National Institutes of Health. The government has certain rights in the invention. --, therefor.

Signed and Sealed this
Twenty-ninth Day of October, 2024

Katherine Kelly Vidal

Katherine Kelly Vidal
*Director of the United States Patent and Trademark Office*